US007388023B2

(12) United States Patent
Blazecka et al.

(10) Patent No.: US 7,388,023 B2
(45) Date of Patent: Jun. 17, 2008

(54) AMINO ACIDS WITH AFFINITY FOR THE α2δ-PROTEIN

(75) Inventors: Peter Garth Blazecka, Windsor (CA); Joseph Richard Bozelak, Munith, MI (US); Norman Lloyd Colbry, Gregory, MI (US); Timothy Thomas Curran, Whitmore Lake, MI (US); Annise Paige Goodman, Farmington Hills, MI (US); Kevin E. Henegar, Ann Arbor, MI (US); Garrett Hoge, Ann Arbor, MI (US); Paul D. Johnson, Kalamazoo, MI (US); Augustine Tobi Osuma, Canton, MI (US); Mark Stephen Plummer, Dexter, MI (US); Jacob Bradley Schwarz, Ann Arbor, MI (US); Derek Clinton Vrieze, Ann Arbor, MI (US); Ji Zhang, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 1 day.

(21) Appl. No.: 11/567,878

(22) Filed: Dec. 7, 2006

(65) Prior Publication Data

US 2007/0129550 A1 Jun. 7, 2007

Related U.S. Application Data

(62) Division of application No. 10/949,907, filed on Sep. 24, 2004, now Pat. No. 7,179,934.

(60) Provisional application No. 60/505,953, filed on Sep. 25, 2003, provisional application No. 60/507,443, filed on Sep. 30, 2003.

(51) Int. Cl.
*A61K 31/44* (2006.01)
*A61K 31/195* (2006.01)
*C07D 213/38* (2006.01)
*C07D 231/46* (2006.01)
*C07C 53/134* (2006.01)
*C07C 53/126* (2006.01)

(52) U.S. Cl. .................. 514/357; 514/784; 546/335; 562/400; 562/401

(58) Field of Classification Search ............... None
See application file for complete search history.

(56) References Cited

U.S. PATENT DOCUMENTS

2003/0195251 A1 10/2003 Barta et al.

OTHER PUBLICATIONS

Gedey, et al. "Preparation of highly enantiopure β-amino esters by Candida antarctica lipase A" (2001) pp. 105-110, Tetrahedron: Asymmetry, vol. 12(1).*

Arvanitis et al., Enantioselective synthesis of 2-substitured 3-amniopropanoic acid (Beta-alanine) derivatives which are Beta-analogues of aromatic amino acids, J. Chem. Soc., Perkin Trans. 1, (1998), pp. 521-528.
Bull S.D. et al, "Asymmetric Synthesis of Beta-amino Acid Scaffolds", J. Chem Soc., Perkin Trans. 1, (2001), pp. 2931-2938, vol. 22.
Davies, S.G. et al, "Asymmetric Synthesis of Beta-Phenylalanine, Alpha-Methyl-Beta-Phenylalanines and Derivatives", J. Chem. Soc., Chem. Commun., (1993), pp. 1153-1155.
Davies, S. G., et al, "A Succinct Asymmetric Synthesis of (2S,3R)-2-Methyl-3-aminopentanoic Acid Hydrochloride", Synlett, (1994), pp. 117-118.
Davis, F.A. et al., "Concise Asymmetric Synthesis of Alpha-Amino Acid Derivatives from N-Sulfinylimino Esters," J. Org. Chem., (1999), pp. 3396-3397, vol. 64.
Davis, F.A. et al., "Improved Synthesis of Enantiopure Sulfinimines (Thiooxime S-Oxides) from p-Toluenesulfinamide and Aldehydes and Ketones," J. Org. Chem. (1999), pp. 1403-1406, vol. 64.
Dixon, W. J., W., "Efficient Analysis of Experimental Observations", Ann. Rev. Pharmacol. Toxicol., (1980), pp. 441-462, vol. 20.
Evans, D. A. et al, "A General Method for the Synthesis of Enantiomerically Pure Beta-Substituted, Beta-Amino Acids through Alpha-Substituted Succinic Acid Derivatives", J. Org. Chem., (1999), pp. 6411-6417, vol. 64.
Gee, N. S. et al, "The Novel Anticonvulsant Drug, Gabapentin (Neurontin), Binds to the Alpha2Beta Subunit of a Calcium Channel", J. Biol. Chem., (1996), pp. 5768-5776, vol. 271(10).
Hargreaves, K. et al, "A New and Sensitive Method for Measuring Thermal Nociception in Cutaneous Hyperalgesia", Pain, (1998), pp. 77-88, vol. 32.
Hawkins J. et al., Asymmetric Michael Reactions of 3,5-Dihydro-4H-dinaphth[2,1-c:1',2'-e]azepine with Methyl Crotonate, J.Org. Chem., (1986), pp. 2820-2822, vol. 51.
Hintermann T. et al., "A Useful Modification of the Evans Auxilliary: 4-Isopropyl-5,5-diphenyloxazolidin-2-one," Helvetica Chimica Acta, (1998), pp. 2093-2126, vol. 81.
Ho, G.J. et al, "Lithium-Initiated Imide Formation. A Simple Method for N-Acylation of 2-Oxazolidinones and Bornane-2, 1--Sultam", J. Org. Chem., (1995), pp. 2271-2273, vol. 60.
Ishikawa et al, "Chiral Lewis Acid-Hydroxylamine Hybrid Reagent for Enantioselective Michael Addition Reaction Directed Towards Beta-Amino Acids Synthesis", Synlett, (1998), pp. 1291-1293, vol. 11.
Juaristi, E., "Enantioselective Synthesis of beta-Amino Acids", Tetrahedron: Asymmetry, (1996), pp. 2233-2246, vol. 7, No. 8.
Myers, A. G. et al., "Highly Practical Methodology for the Synthesis of D- and L-Alpha-Amino Acids, N-Protected Alpha-Amino Acids, and N-Methyl-Alpha-Amino Acids," J. Am. Chem. Soc., (1997), pp. 656-673, vol. 119.

(Continued)

*Primary Examiner*—Rebecca Anderson
*Assistant Examiner*—Michael P. Barker
(74) *Attorney, Agent, or Firm*—Matthew J. Russo; Lucy X. Yang

(57) ABSTRACT

Certain β-amino acids that bind to the alpha-2-delta (α2δ) subunit of a calcium channel are disclosed. These compounds and their pharmaceutically acceptable salts are useful in the treatment of a variety of psychiatric, pain and other disorders. Also disclosed are methods of making the β-amino acids.

16 Claims, No Drawings

OTHER PUBLICATIONS

Nagula, G. et al., "Synthesis of Alpha-Substituted Beta-Amino Acids Using Pseudoephedrine as a Chiral Auxiliary," Org. Letters, (2000), pp. 3527-3529, vol. 2.

Palomino E., "Delivery of Drugs Through Dihydropyridine Carriers", Drugs of the Future, (1990), pp. 361-368, vol. 15(4).

Randall L.O., et al, "A Method for Measurement of Analgesic Activitity On Inflamed Tissue", Arch. Int. Pharmacodyn., (1957), pp. 409-419, vol. 4.

Seebach, D. et al, "EPC_Synthesis of Beta-Amino Acid Derivatives through Lithiated Hydropyrimidines" Eur: J. Org. Chem., (1999), pp. 335-360.

Sibi, M.P. et al., "A New Methodology for the Synthesis of Beta-Amino Acids", J. Chem. Soc., Perkin Trans.1, (2000), pp. 1461-1466, vol. 9.

Sluka, K., et al, "Unilateral Intramuscular Injections of Acidic Saline Produce a Bilateral Long-Lasting Hyperalgesia", Muscle Nerve, (2001), pp. 37-46, vol. 24.

Tang, T. P. et al, "The tert-Butanesulfinyl Group: An Ideal Chiral Directing Group and Boc-Surrogate for the Asymmetric Synthesis and Applications of Beta-Amino Acids", J. Org. Chem., (1999), pp. 12-13, vol. 64.

Vogel, J.R. et al, "A Simple and Reliable Conflict Proceure for Testing Anti-Anxiety Agents", Psychopharmacologia, (1971), pp. 1-7, vol. 21.

Yuen P. W. et al, "Enantioselective Synthesis of PD144723: A Potent Stereospecific Anticonvulsant", Bioorganic & Med. Chem Lett., (1994), pp. 823-825, vol. 4(6).

* cited by examiner

AMINO ACIDS WITH AFFINITY FOR THE α2δ-PROTEIN

CROSS REFERENCE TO RELATED APPLICATIONS

This application is a division of copending and commonly assigned U.S. application Ser. No. 10/949,907, filed Sep. 24, 2004, which claims the benefit of U.S. Provisional Application No. 60/505,953, filed Sep. 25, 2003, and U.S. Provisional Application No. 60/507,443, filed Sep. 30, 2003, the complete disclosures of which are herein incorporated by reference.

BACKGROUND OF THE INVENTION

This invention relates to certain β-amino acids that bind to the alpha-2-delta (α2δ) subunit of a calcium channel. These compounds and their pharmaceutically acceptable salts are useful in the treatment of a variety of psychiatric, pain, and other disorders.

SUMMARY OF THE INVENTION

This invention provides compounds of formula I,

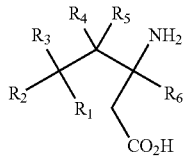

and their pharmaceutically acceptable salts, wherein $R_1$ is a hydrogen atom or $(C_1-C_6)$alkyl optionally substituted with from one to five fluorine atoms;

$R_2$ is a hydrogen atom or $(C_1-C_6)$alkyl optionally substituted with from one to five fluorine atoms; or $R_1$ and $R_2$, together with the carbon to which they are attached, form a three- to six-membered cycloalkyl ring;

$R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, preferably with from zero to three fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents, preferably with from zero to two substituents, independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms;

$R_4$ is a hydrogen atom or $(C_1-C_6)$alkyl optionally substituted with from one to five fluorine atoms;

$R_5$ is a hydrogen atom or $(C_1-C_6)$alkyl optionally substituted with from one to five fluorine atoms;

$R_4$ and $R_5$, together with the carbon to which they are attached, form a three- to six-membered cycloalkyl ring; and $R_6$ is a hydrogen atom or $(C_1-C_6)$alkyl;

with the proviso that $R_1$, $R_2$, $R_3$, $R_4$, $R_5$, and $R_6$ are not simultaneously hydrogen atoms.

Specific compounds of formula I include the following compounds and their pharmaceutically acceptable salts:
3-Amino-4,5-dimethyl-hexanoic acid;
3-Amino-4,5-dimethyl-heptanoic acid;
3-Amino-4,5-dimethyl-octanoic acid;
3-Amino-4,5-dimethyl-nonanoic acid;
3-Amino-4,5-dimethyl-decanoic acid;
3-Amino-4-ethyl-5-methyl-heptanoic acid;
3-Amino-4-ethyl-5-methyl-octanoic acid;
3-Amino-4-ethyl-5-methyl-nonanoic acid;
3-Amino-4-ethyl-5,6-dimethyl-heptanoic acid;
3-Amino-4-ethyl-5,7-dimethyl-octanoic acid;
3-Amino-4-ethyl-5,8-dimethyl-nonanoic acid;
3-Amino-5-ethyl-4-methyl-octanoic acid;
3-Amino-5-ethyl-4-methyl-nonanoic acid;
3-Amino-4,5-diethyl-heptanoic acid;
3-Amino-4,5-diethyl-octanoic acid;
3-Amino-4,5-diethyl-nonanoic acid;
3-Amino-5-ethyl-4,7-dimethyl-octanoic acid;
3-Amino-5-ethyl-4,8-dimethyl-nonanoic acid;
3-Amino-4,5-diethyl-6-methyl-heptanoic acid;
3-Amino-4,5-diethyl-7-methyl-octanoic acid;
3-Amino-4,5-diethyl-8-methyl-nonanoic acid;
3-Amino-4,5,6-trimethyl-heptanoic acid;
3-Amino-4,5,7-trimethyl-octanoic acid;
3-Amino-4,5,8-trimethyl-nonanoic acid;
3-Amino-4-ethyl-5-methyl-hexanoic acid;
3-Amino-5-ethyl-4-methyl-octanoic acid;
3-Amino-5-ethyl-4-methyl-heptanoic acid;
3-Amino-4-methyl-5-propyl-octanoic acid;
3-Amino-4-methyl-6-ethyl-octanoic acid;
3-Amino-4-methyl-6-ethyl-nonanoic acid;
3-Amino-4,6-diethyl-octanoic acid;
3-Amino-4,6-diethyl-nonanoic acid;
3-Amino-6-cyclopentyl-4,5-dimethyl-hexanoic acid;
3-Amino-7-cyclopentyl-4,5-dimethyl-heptanoic acid;
3-Amino-5-ethyl-4,6-dimethyl-heptanoic acid;
3-Amino-5-ethyl-4,7-dimethyl-octanoic acid;
3-Amino-5-ethyl-4,8-dimethyl-nonanoic acid;
(3R,4R)-3-Amino-4,5-dimethyl-hexanoic acid;
(3R,4R,5R)-3-Amino-4,5-dimethyl-heptanoic acid;
(3R,4R,5R)-3-Amino-4,5-dimethyl-octanoic acid;
(3R,4R,5R)-3-Amino-4,5-dimethyl-nonanoic acid;
(3R,4R,5R)-3-Amino-4,5-dimethyl-decanoic acid;
3-Amino-5-cyclopropyl-4-ethyl-hexanoic acid;
3-Amino-6-cyclopropyl-4-ethyl-5-methyl-hexanoic acid;
3-Amino-5-cyclobutyl-4-ethyl-hexanoic acid;
3-Amino-6-cyclobutyl-4-ethyl-5-methyl-hexanoic acid;
3-Amino-5-cyclopentyl-4-methyl-hexanoic acid;
3-Amino-6-cyclopentyl-4-ethyl-5-methyl-hexanoic acid;
3-Amino-5-cyclohexyl-4-ethyl-hexanoic acid;
3-Amino-6-cyclohexyl-4-ethyl-5-methyl-hexanoic acid;
3-Amino-5-cyclopropyl-4-methyl-hexanoic acid;
3-Amino-6-cyclopropyl-4,5-dimethyl-hexanoic acid;
3-Amino-5-cyclobutyl-4-methyl-hexanoic acid;
3-Amino-6-cyclobutyl-4,5-dimethyl-hexanoic acid;
3-Amino-5-cyclopentyl-4-methyl-hexanoic acid;
3-Amino-6-cyclopentyl-4,5-dimethyl-hexanoic acid;
3-Amino-5-cyclohexyl-4-methyl-hexanoic acid;
3-Amino-6-cyclohexyl-4,5-dimethyl-hexanoic acid;
3-Amino-8-cyclohexyl-4,5-dimethyl-octanoic acid;
3-Amino-8-cyclohexyl-4,5-dimethyl-octanoic acid;
3-Amino-4,6-dimethyl-heptanoic acid;
3-Amino-4,6-dimethyl-octanoic acid;
3-Amino-4,6-dimethyl-nonanoic acid;
3-Amino-4,6-dimethyl-decanoic acid;
3-Amino-4,6,7-trimethyl-octanoic acid;

3-Amino-4,6,8-trimethyl-nonanoic acid;
3-Amino-4,6,9-trimethyl-decanoic acid;
3-Amino-6-cyclopropyl-4-methyl-heptanoic acid;
3-Amino-6-cyclobutyl-4-methyl-heptanoic acid;
3-Amino-6-cyclopentyl-4-methyl-heptanoic acid;
3-Amino-6-cyclohexyl-4-methyl-heptanoic acid;
3-Amino-7-cyclopropyl-4,6-dimethyl-heptanoic acid;
3-Amino-7-cyclobutyl-4,6-dimethyl-heptanoic acid;
3-Amino-7-cyclopentyl-4,6-dimethyl-heptanoic acid;
3-Amino-7-cyclohexyl-4,6-dimethyl-heptanoic acid;
3-Amino-8-cyclopropyl-4,6-dimethyl-octanoic acid;
3-Amino-8-cyclobutyl-4,6-dimethyl-octanoic acid;
3-Amino-8-cyclopentyl-4,6-dimethyl-octanoic acid;
3-Amino-8-cyclohexyl-4,6-dimethyl-octanoic acid;
3-Amino-6-(3-chloro-phenyl)-4-methyl-heptanoic acid;
3-Amino-6-(3,4-dichloro-phenyl)-4-methyl-heptanoic acid;
3-Amino-4-methyl-6-(3-trifluoromethyl-phenyl)-heptanoic acid;
3-Amino-4-methyl-6-(4-trifluoromethyl-phenyl)-heptanoic acid;
3-Amino-7-(3-chloro-phenyl)-4,6-dimethyl-heptanoic acid;
3-Amino-7-(3,4-dichloro-phenyl)-4,6-dimethyl-heptanoic acid;
3-Amino-4,6-dimethyl-7-(3-trifluoromethyl-phenyl)-heptanoic acid;
3-Amino-4,6-dimethyl-7-(4-trifluoromethyl-phenyl)-heptanoic acid;
3-Amino-8-(3-chloro-phenyl)-4,6-dimethyl-octanoic acid;
3-Amino-8-(3,4-dichloro-phenyl)-4,6-dimethyl-octanoic acid;
3-Amino-4,6-dimethyl-8-(3-trifluoromethyl-phenyl)-octanoic acid;
3-Amino-4,6-dimethyl-8-(4-trifluoromethyl-phenyl)-octanoic acid;
3-Amino-4-ethyl-6-methyl-octanoic acid;
3-Amino-4-ethyl-6-methyl-nonanoic acid;
3-Amino-4-ethyl-6-methyl-decanoic acid;
3-Amino-4-ethyl-6,7-dimethyl-octanoic acid;
3-Amino-4-ethyl-6,8-dimethyl-nonanoic acid;
3-Amino-4-ethyl-6,9-dimethyl-decanoic acid;
3-Amino-6-cyclopropyl-4-ethyl-heptanoic acid;
3-Amino-6-cyclobutyl-4-ethyl-heptanoic acid;
3-Amino-6-cyclopentyl-4-ethyl-heptanoic acid;
3-Amino-6-cyclohexyl-4-ethyl-heptanoic acid;
3-Amino-7-cyclopropyl-4-ethyl-6-methyl-heptanoic acid;
3-Amino-7-cyclobutyl-4-ethyl-6-methyl-heptanoic acid;
3-Amino-7-cyclopentyl-4-ethyl-6-methyl-heptanoic acid;
3-Amino-7-cyclohexyl-4-ethyl-6-methyl-heptanoic acid;
3-Amino-8-cyclopropyl-4-ethyl-6-methyl-octanoic acid;
3-Amino-8-cyclobutyl-4-ethyl-6-methyl-octanoic acid;
3-Amino-8-cyclopentyl-4-ethyl-6-methyl-octanoic acid;
3-Amino-8-cyclohexyl-4-ethyl-6-methyl-octanoic acid;
3-Amino-6-(3-chloro-phenyl)-4-ethyl-heptanoic acid;
3-Amino-6-(3,4-dichloro-phenyl)-4-ethyl-heptanoic acid;
3-Amino-4-ethyl-6-(3-trifluoromethyl-phenyl)-heptanoic acid;
3-Amino-4-ethyl-6-(4-trifluoromethyl-phenyl)-heptanoic acid;
3-Amino-7-(3-chloro-phenyl)-4-ethyl-6-methyl-heptanoic acid;
3-Amino-7-(3,4-dichloro-phenyl)-4-ethyl-6-methyl-heptanoic acid;
3-Amino-4-ethyl-6-methyl-7-(3-trifluoromethyl-phenyl)-heptanoic acid;
3-Amino-4-ethyl-6-methyl-7-(4-trifluoromethyl-phenyl)-heptanoic acid;
3-Amino-8-(3-chloro-phenyl)-4-ethyl-6-methyl-octanoic acid;
3-Amino-8-(3,4-dichloro-phenyl)-4-ethyl-6-methyl-octanoic acid;
3-Amino-4-ethyl-6-methyl-8-(3-trifluoromethyl-phenyl)-octanoic acid;
3-Amino-4-ethyl-6-methyl-8-(4-trifluoromethyl-phenyl)-octanoic acid;
3-Amino-4-methyl-heptanoic acid;
3-Amino-4,6-dimethyl-heptanoic acid;
3-Amino-4,7-dimethyl-octanoic acid;
3-Amino-4,8-dimethyl-nonanoic acid;
3-Amino-4-methyl-hexanoic acid;
3-Amino-4-methyl-heptanoic acid;
3-Amino-4-methyl-octanoic acid;
3-Amino-4-methyl-nonanoic acid;
3-Amino-5-cyclopropyl-4-methyl-pentanoic acid;
3-Amino-6-cyclopropyl-4-methyl-hexanoic acid;
3-Amino-7-cyclopropyl-4-methyl-heptanoic acid;
3-Amino-5-cyclobutyl-4-methyl-pentanoic acid;
3-Amino-6-cyclobutyl-4-methyl-hexanoic acid;
3-Amino-7-cyclobutyl-4-methyl-heptanoic acid;
3-Amino-5-cyclopentyl-4-methyl-pentanoic acid;
3-Amino-6-cyclopentyl-4-methyl-hexanoic acid;
3-Amino-7-cyclopentyl-4-methyl-heptanoic acid;
3-Amino-5-cyclohexyl-4-methyl-pentanoic acid;
3-Amino-6-cyclohexyl-4-methyl-hexanoic acid;
3-Amino-7-cyclohexyl-4-methyl-heptanoic acid;
3-Amino-5-cyclopropyl-4-ethyl-pentanoic acid;
3-Amino-6-cyclopropyl-4-ethyl-hexanoic acid;
3-Amino-7-cyclopropyl-4-ethyl-heptanoic acid;
3-Amino-5-cyclobutyl-4-ethyl-pentanoic acid;
3-Amino-6-cyclobutyl-4-ethyl-hexanoic acid;
3-Amino-7-cyclobutyl-4-ethyl-heptanoic acid;
3-Amino-5-cyclopentyl-4-ethyl-pentanoic acid;
3-Amino-6-cyclopentyl-4-ethyl-hexanoic acid;
3-Amino-7-cyclopentyl-4-ethyl-heptanoic acid;
3-Amino-5-cyclohexyl-4-ethyl-pentanoic acid;
3-Amino-6-cyclohexyl-4-ethyl-hexanoic acid;
3-Amino-7-cyclohexyl-4-ethyl-heptanoic acid;
3-Amino-4,4,5-trimethyl-heptanoic acid;
3-Amino-4,4,5-trimethyl-octanoic acid;
3-Amino-4,4,5-trimethyl-hexanoic acid;
3-Amino-4,5,5-trimethyl-heptanoic acid;
3-Amino-4,5,5-trimethyl-octanoic acid; and
3-Amino-4,5,5-trimethyl-hexanoic acid.

Other compounds of formula I include the following compounds, and their pharmaceutically acceptable salts:
3-Amino-4-methyl-5-phenyl-pentanoic acid;
3-Amino-4-methyl-6-phenyl-hexanoic acid;
3-Amino-4-methyl-7-phenyl-heptanoic acid;
3-Amino-5-(2-chloro-phenyl)-4-methyl-pentanoic acid;
3-Amino-5-(3-chloro-phenyl)-4-methyl-pentanoic acid;
3-Amino-5-(4-chloro-phenyl)-4-methyl-pentanoic acid;
3-Amino-5-(2,4-dichloro-phenyl)-4-methyl-pentanoic acid;
3-Amino-5-(3,4-dichloro-phenyl)-4-methyl-pentanoic acid;
3-Amino-4-(2-chloro-benzyl)-hexanoic acid;
3-Amino-4-(3-chloro-benzyl)-hexanoic acid;
3-Amino-4-(4-chloro-benzyl)-hexanoic acid;
3-Amino-4-(2,4-dichloro-benzyl)-hexanoic acid;
3-Amino-4-(3,4-dichloro-benzyl)-hexanoic acid;
3-Amino-6-(2-chloro-phenyl)-4-methyl-hexanoic acid;
3-Amino-6-(3-chloro-phenyl)-4-methyl-hexanoic acid;
3-Amino-6-(4-chloro-phenyl)-4-methyl-hexanoic acid;
3-Amino-6-(2,4-dichloro-phenyl)-4-methyl-hexanoic acid;
3-Amino-6-(3,4-dichloro-phenyl)-4-methyl-hexanoic acid;
3-Amino-6-(2-chloro-phenyl)-4-ethyl-hexanoic acid;

3-Amino-6-(3-chloro-phenyl)-4-ethyl-hexanoic acid;
3-Amino-6-(4-chloro-phenyl)-4-ethyl-hexanoic acid;
3-Amino-6-(2,4-dichloro-phenyl)-4-ethyl-hexanoic acid;
3-Amino-6-(3,4-dichloro-phenyl)-4-ethyl-hexanoic acid;
3-Amino-7-(2-chloro-phenyl)-4-methyl-heptanoic acid;
3-Amino-7-(3-chloro-phenyl)-4-methyl-heptanoic acid;
3-Amino-7-(4-chloro-phenyl)-4-methyl-heptanoic acid;
3-Amino-7-(2,4-dichloro-phenyl)-4-methyl-heptanoic acid;
3-Amino-7-(3,4-dichloro-phenyl)-4-methyl-heptanoic acid;
3-Amino-7-(2-chloro-phenyl)-4-ethyl-heptanoic acid;
3-Amino-7-(3-chloro-phenyl)-4-ethyl-heptanoic acid;
3-Amino-7-(4-chloro-phenyl)-4-ethyl-heptanoic acid;
3-Amino-7-(2,4-dichloro-phenyl)-4-ethyl-heptanoic acid; and
3-Amino-7-(3,4-dichloro-phenyl)-4-ethyl-heptanoic acid.

This invention also provides compounds of formula II

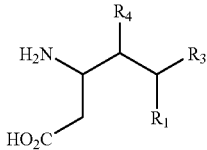

II and their pharmaceutically acceptable salts, wherein $R_1$, $R_3$, and $R_4$ are as defined above in formula I, with the proviso that $R_1$ is not a hydrogen atom.

Specific compounds of formula II include the following compounds and their pharmaceutically acceptable salts:
3-Amino-4,5-dimethyl-hexanoic acid;
3-Amino-4,5-dimethyl-heptanoic acid;
3-Amino-4,5-dimethyl-octanoic acid;
3-Amino-4,5-dimethyl-nonanoic acid;
3-Amino-4-ethyl-5-methyl-heptanoic acid;
3-Amino-4-ethyl-5-methyl-octanoic acid;
3-Amino-4-ethyl-5-methyl-nonanoic acid;
3-Amino-4-ethyl-5,6-dimethyl-heptanoic acid;
3-Amino-4-ethyl-5,7-dimethyl-octanoic acid;
3-Amino-4-ethyl-5,8-dimethyl-nonanoic acid;
3-Amino-5-ethyl-4-methyl-octanoic acid;
3-Amino-5-ethyl-4-methyl-nonanoic acid;
3-Amino-4,5-diethyl-heptanoic acid;
3-Amino-4,5-diethyl-octanoic acid;
3-Amino-4,5-diethyl-nonanoic acid;
3-Amino-5-ethyl-4,7-dimethyl-octanoic acid;
3-Amino-5-ethyl-4,8-dimethyl-nonanoic acid;
3-Amino-4,5-diethyl-6-methyl-heptanoic acid;
3-Amino-4,5-diethyl-7-methyl-octanoic acid;
3-Amino-4,5-diethyl-8-methyl-nonanoic acid;
3-Amino-4,5,6-trimethyl-heptanoic acid;
3-Amino-4,5,7-trimethyl-octanoic acid;
3-Amino-4,5,8-trimethyl-nonanoic acid;
3-Amino-4-ethyl-5-methyl-hexanoic acid;
3-Amino-5-ethyl-4-methyl-octanoic acid;
3-Amino-5-ethyl-4-methyl-heptanoic acid;
3-Amino-4-methyl-5-propyl-octanoic acid;
3-Amino-6-cyclopentyl-4,5-dimethyl-hexanoic acid;
3-Amino-7-cyclopentyl-4,5-dimethyl-heptanoic acid;
3-Amino-5-ethyl-4,6-dimethyl-heptanoic acid;
3-Amino-5-ethyl-4,7-dimethyl-octanoic acid;
3-Amino-5-ethyl-4,8-dimethyl-nonanoic acid;
(3R,4R)-3-Amino-4,5-dimethyl-hexanoic acid;
(3R,4R,5R)-3-Amino-4,5-dimethyl-heptanoic acid;
(3R,4R,5R)-3-Amino-4,5-dimethyl-octanoic acid;
(3R,4R,5R)-3-Amino-4,5-dimethyl-nonanoic acid;
(3R,4R,5R)-3-Amino-4,5-decanoic acid;
3-Amino-5-cyclopropyl-4-ethyl-hexanoic acid;
3-Amino-6-cyclopropyl-4-ethyl-5-methyl-hexanoic acid;
3-Amino-5-cyclobutyl-4-ethyl-hexanoic acid;
3-Amino-6-cyclobutyl-4-ethyl-5-methyl-hexanoic acid;
3-Amino-5-cyclopentyl-4-methyl-hexanoic acid;
3-Amino-6-cyclopentyl-4-ethyl-5-methyl-hexanoic acid;
3-Amino-5-cyclohexyl-4-ethyl-hexanoic acid;
3-Amino-6-cyclohexyl-4-ethyl-5-methyl-hexanoic acid;
3-Amino-5-cyclopropyl-4-methyl-hexanoic acid;
3-Amino-6-cyclopropyl-4,5-dimethyl-hexanoic acid;
3-Amino-5-cyclobutyl-4-methyl-hexanoic acid;
3-Amino-6-cyclobutyl-4,5-dimethyl-hexanoic acid;
3-Amino-5-cyclopentyl-4-methyl-hexanoic acid;
3-Amino-6-cyclopentyl-4,5-dimethyl-hexanoic acid;
3-Amino-5-cyclohexyl-4-methyl-hexanoic acid;
3-Amino-6-cyclohexyl-4,5-dimethyl-hexanoic acid;
3-Amino-8-cyclohexyl-4,5-dimethyl-octanoic acid and
3-Amino-8-cyclohexyl-4,5-dimethyl-octanoic acid.

This invention also provides compounds of formula III

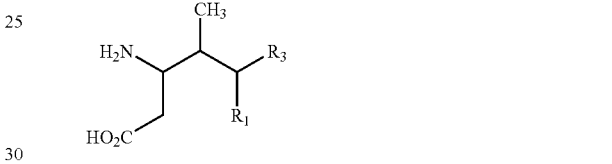

III and their pharmaceutically acceptable salts, wherein $R_1$ and $R_3$ are as defined above in formula I, with the proviso that $R_1$ and $R_3$ are not hydrogen atoms.

Specific compounds of formula III include the following compounds and their pharmaceutically acceptable salts:
3-Amino-4,5-dimethyl-hexanoic acid;
3-Amino-4,5-dimethyl-heptanoic acid;
3-Amino-4,5-dimethyl-octanoic acid;
3-Amino-4,5-dimethyl-nonanoic acid;
3-Amino-4,5,6-trimethyl-heptanoic acid;
3-Amino-4,5,7-trimethyl-octanoic acid;
3-Amino-4,5,8-trimethyl-nonanoic acid;
3-Amino-4-methyl-5-propyl-octanoic acid;
3-Amino-6-cyclopentyl-4,5-dimethyl-hexanoic acid;
3-Amino-7-cyclopentyl-4,5-dimethyl-heptanoic acid;
3-Amino-5-ethyl-4,6-dimethyl-heptanoic acid;
3-Amino-5-ethyl-4,7-dimethyl-octanoic acid;
3-Amino-5-ethyl-4,8-dimethyl-nonanoic acid;
(3R,4R)-3-Amino-4,5-dimethyl-hexanoic acid;
(3R,4R,5R)-3-Amino-4,5-dimethyl-heptanoic acid;
(3R,4R,5R)-3-Amino-4,5-dimethyl-octanoic acid;
(3R,4R,5R)-3-Amino-4,5-dimethyl-nonanoic acid;
(3R,4R,5R)-3-Amino-4,5-dimethyl-decanoic acid;
3-Amino-5-cyclopentyl-4-methyl-hexanoic acid;
3-Amino-5-cyclopropyl-4-methyl-hexanoic acid;
3-Amino-6-cyclopropyl-4,5-dimethyl-hexanoic acid;
3-Amino-5-cyclobutyl-4-methyl-hexanoic acid;
3-Amino-6-cyclobutyl-4,5-dimethyl-hexanoic acid;
3-Amino-5-cyclopentyl-4-methyl-hexanoic acid;
3-Amino-6-cyclopentyl-4,5-dimethyl-hexanoic acid;
3-Amino-5-cyclohexyl-4-methyl-hexanoic acid;
3-Amino-6-cyclohexyl-4,5-dimethyl-hexanoic acid;
3-Amino-8-cyclohexyl-4,5-dimethyl-octanoic acid and
3-Amino-8-cyclohexyl-4,5-dimethyl-octanoic acid.

This invention also provides compounds of formula IV

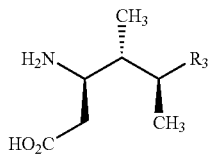

and their pharmaceutically acceptable salts, wherein $R_3$ is as defined above in formula I, with the proviso that $R_3$ is not a hydrogen atom.

Specific compounds of formula IV include the following compounds and their pharmaceutically acceptable salts:
(3R,4R)-3-Amino-4,5-dimethyl-hexanoic acid;
(3R,4R,5R)-3-Amino-4,5-dimethyl-heptanoic acid;
(3R,4R,5R)-3-Amino-4,5-dimethyl-octanoic acid;
(3R,4R,5R)-3-Amino-4,5-dimethyl-nonanoic acid and
(3R,4R,5R)-3-Amino-4,5-dimethyl-decanoic acid.

This invention also relates to compounds of formula V

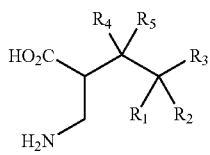

and their pharmaceutically acceptable salts, wherein $R_1$, $R_2$, $R_3$, $R_4$, and $R_5$ are as defined above in formula I, with the proviso that $R_1$, $R_2$, $R_3$, $R_4$, and $R_5$ are not simultaneously hydrogen atoms.

Specific compounds of formula V include the following compounds and their pharmaceutically acceptable salts:
2-Aminomethyl-4-(2-fluoro-phenyl)-pentanoic acid;
2-Aminomethyl-4-(3-fluoro-phenyl)-pentanoic acid;
2-Aminomethyl-4-(4-fluoro-phenyl)-pentanoic acid;
2-Aminomethyl-4-(2,3-difluoro-phenyl)-pentanoic acid;
2-Aminomethyl-4-(2,4-difluoro-phenyl)-pentanoic acid;
2-Aminomethyl-4-(2,5-difluoro-phenyl)-pentanoic acid;
2-Aminomethyl-4-(2,6-difluoro-phenyl)-pentanoic acid;
2-Aminomethyl-4-(3,4-difluoro-phenyl)-pentanoic acid;
2-Aminomethyl-4-(3,5-difluoro-phenyl)-pentanoic acid;
2-Aminomethyl-4-(2,3,4-trifluoro-phenyl)-pentanoic acid;
2-Aminomethyl-4-(2,3,5-trifluoro-phenyl)-pentanoic acid;
2-Aminomethyl-4-(2,3,6-trifluoro-phenyl)-pentanoic acid;
2-Aminomethyl-4-(2,4,6-trifluoro-phenyl)-pentanoic acid;
2-Aminomethyl-4-(2,3,4,5-tetrafluoro-phenyl)-pentanoic acid;
2-Aminomethyl-4-(2,3,4,6-tetrafluoro-phenyl)-pentanoic acid;
2-Aminomethyl-4-(2,3,5,6-tetrafluoro-phenyl)-pentanoic acid;
2-Aminomethyl-4-pentafluorophenyl-pentanoic acid;
2-Aminomethyl-4-(2-fluoro-phenyl)-hexanoic acid;
2-Aminomethyl-4-(3-fluoro-phenyl)-hexanoic acid;
2-Aminomethyl-4-(4-fluoro-phenyl)-hexanoic acid;
2-Aminomethyl-4-(2,3-difluoro-phenyl)-hexanoic acid;
2-Aminomethyl-4-(2,4-difluoro-phenyl)-hexanoic acid;
2-Aminomethyl-4-(2,5-difluoro-phenyl)-hexanoic acid;
2-Aminomethyl-4-(2,6-difluoro-phenyl)-hexanoic acid;
2-Aminomethyl-4-(3,4-difluoro-phenyl)-hexanoic acid;
2-Aminomethyl-4-(3,5-difluoro-phenyl)-hexanoic acid;
2-Aminomethyl-4-(2,3,4-trifluoro-phenyl)-hexanoic acid;
2-Aminomethyl-4-(2,3,5-trifluoro-phenyl)-hexanoic acid;
2-Aminomethyl-4-(2,3,6-trifluoro-phenyl)-hexanoic acid;
2-Aminomethyl-4-(2,4,6-trifluoro-phenyl)-hexanoic acid;
2-Aminomethyl-4-(2,3,4,5-tetrafluoro-phenyl)-hexanoic acid;
2-Aminomethyl-4-(2,3,4,6-tetrafluoro-phenyl)-hexanoic acid;
2-Aminomethyl-4-(2,3,5,6-tetrafluoro-phenyl)-hexanoic acid;
2-Aminomethyl-4-pentafluorophenyl-hexanoic acid;
2-Aminomethyl-5-(2-fluoro-phenyl)-4-methyl-pentanoic acid;
2-Aminomethyl-5-(3-fluoro-phenyl)-4-methyl-pentanoic acid;
2-Aminomethyl-5-(4-fluoro-phenyl)-4-methyl-pentanoic acid;
2-Aminomethyl-5-(2,3-difluoro-phenyl)-4-methyl-pentanoic acid;
2-Aminomethyl-5-(2,4-difluoro-phenyl)-4-methyl-pentanoic acid;
2-Aminomethyl-5-(2,5-difluoro-phenyl)-4-methyl-pentanoic acid;
2-Aminomethyl-5-(2,6-difluoro-phenyl)-4-methyl-pentanoic acid;
2-Aminomethyl-5-(3,4-difluoro-phenyl)-4-methyl-pentanoic acid;
2-Aminomethyl-5-(3,5-difluoro-phenyl)-4-methyl-pentanoic acid;
2-Aminomethyl-4-methyl-5-(2,3,4-trifluoro-phenyl)-pentanoic acid;
2-Aminomethyl-4-methyl-5-(2,3,5-trifluoro-phenyl)-pentanoic acid;
2-Aminomethyl-4-methyl-5-(2,3,6-trifluoro-phenyl)-pentanoic acid;
2-Aminomethyl-4-methyl-5-(2,4,6-trifluoro-phenyl)-pentanoic acid;
2-Aminomethyl-4-methyl-5-(2,3,4,5-tetrafluoro-phenyl)-pentanoic acid;
2-Aminomethyl-4-methyl-5-(2,3,4,6-tetrafluoro-phenyl)-pentanoic acid;
2-Aminomethyl-4-methyl-5-(2,3,5,6-tetrafluoro-phenyl)-pentanoic acid;
2-Aminomethyl-4-methyl-5-pentafluorophenyl-pentanoic acid;
2-Aminomethyl-5-(2-fluoro-phenyl)-4-methyl-hexanoic acid;
2-Aminomethyl-5-(3-fluoro-phenyl)-4-methyl-hexanoic acid;
2-Aminomethyl-5-(4-fluoro-phenyl)-4-methyl-hexanoic acid;
2-Aminomethyl-5-(2,3-difluoro-phenyl)-4-methyl-hexanoic acid;
2-Aminomethyl-5-(2,4-difluoro-phenyl)-4-methyl-hexanoic acid;
2-Aminomethyl-5-(2,5-difluoro-phenyl)-4-methyl-hexanoic acid;
2-Aminomethyl-5-(2,6-difluoro-phenyl)-4-methyl-hexanoic acid;
2-Aminomethyl-5-(3,4-difluoro-phenyl)-4-methyl-hexanoic acid;
2-Aminomethyl-5-(3,5-difluoro-phenyl)-4-methyl-hexanoic acid;
2-Aminomethyl-4-methyl-5-(2,3,4-trifluoro-phenyl)-hexanoic acid;

2-Aminomethyl-4-methyl-5-(2,3,5-trifluoro-phenyl)-hexanoic acid;
2-Aminomethyl-4-methyl-5-(2,3,6-trifluoro-phenyl)-hexanoic acid;
2-Aminomethyl-4-methyl-5-(2,4,6-trifluoro-phenyl)-hexanoic acid;
2-Aminomethyl-4-methyl-5-(2,3,4,5-tetrafluoro-phenyl)-hexanoic acid;
2-Aminomethyl-4-methyl-5-(2,3,4,6-tetrafluoro-phenyl)-hexanoic acid;
2-Aminomethyl-4-methyl-5-(2,3,5,6-tetrafluoro-phenyl)-hexanoic acid;
2-Aminomethyl-4-methyl-5-pentafluorophenyl-hexanoic acid;
2-Aminomethyl-6-(2-fluoro-phenyl)-4-methyl-hexanoic acid;
2-Aminomethyl-6-(3-fluoro-phenyl)-4-methyl-hexanoic acid;
2-Aminomethyl-6-(4-fluoro-phenyl)-4-methyl-hexanoic acid;
2-Aminomethyl-6-(2,3-difluoro-phenyl)-4-methyl-hexanoic acid;
2-Aminomethyl-6-(2,4-difluoro-phenyl)-4-methyl-hexanoic acid;
2-Aminomethyl-6-(2,5-difluoro-phenyl)-4-methyl-hexanoic acid;
2-Aminomethyl-6-(2,6-difluoro-phenyl)-4-methyl-hexanoic acid;
2-Aminomethyl-6-(3,4-difluoro-phenyl)-4-methyl-hexanoic acid;
2-Aminomethyl-6-(3,5-difluoro-phenyl)-4-methyl-hexanoic acid;
2-Aminomethyl-4-methyl-6-(2,3,4-trifluoro-phenyl)-hexanoic acid;
2-Aminomethyl-4-methyl-6-(2,3,5-trifluoro-phenyl)-hexanoic acid;
2-Aminomethyl-4-methyl-6-(2,3,6-trifluoro-phenyl)-hexanoic acid;
2-Aminomethyl-4-methyl-6-(2,4,6-trifluoro-phenyl)-hexanoic acid;
2-Aminomethyl-4-methyl-6-(2,3,4,5-tetrafluoro-phenyl)-hexanoic acid;
2-Aminomethyl-4-methyl-6-(2,3,4,6-tetrafluoro-phenyl)-hexanoic acid;
2-Aminomethyl-4-methyl-6-(2,3,5,6-tetrafluoro-phenyl)-hexanoic acid;
2-Aminomethyl-4-methyl-6-pentafluorophenyl-hexanoic acid;
2-Aminomethyl-5-(2-fluoro-phenyl)-4-ethyl-pentanoic acid;
2-Aminomethyl-5-(3-fluoro-phenyl)-4-ethyl-pentanoic acid;
2-Aminomethyl-5-(4-fluoro-phenyl)-4-ethyl-pentanoic acid;
2-Aminomethyl-5-(2,3-difluoro-phenyl)-4-ethyl-pentanoic acid;
2-Aminomethyl-5-(2,4-difluoro-phenyl)-4-ethyl-pentanoic acid;
2-Aminomethyl-5-(2,5-difluoro-phenyl)-4-ethyl-pentanoic acid;
2-Aminomethyl-5-(2,6-difluoro-phenyl)-4-ethyl-pentanoic acid;
2-Aminomethyl-5-(3,4-difluoro-phenyl)-4-ethyl-pentanoic acid;
2-Aminomethyl-5-(3,5-difluoro-phenyl)-4-ethyl-pentanoic acid;
2-Aminomethyl-4-ethyl-5-(2,3,4-trifluoro-phenyl)-pentanoic acid;
2-Aminomethyl-4-ethyl-5-(2,3,5-trifluoro-phenyl)-pentanoic acid;
2-Aminomethyl-4-ethyl-5-(2,3,6-trifluoro-phenyl)-pentanoic acid;
2-Aminomethyl-4-ethyl-5-(2,4,6-trifluoro-phenyl)-pentanoic acid;
2-Aminomethyl-4-ethyl-5-(2,3,4,5-tetrafluoro-phenyl)-pentanoic acid;
2-Aminomethyl-4-ethyl-5-(2,3,4,6-tetrafluoro-phenyl)-pentanoic acid;
2-Aminomethyl-4-ethyl-5-(2,3,5,6-tetrafluoro-phenyl)-pentanoic acid;
2-Aminomethyl-4-ethyl-5-pentafluorophenyl-pentanoic acid;
2-Aminomethyl-6-(2-fluoro-phenyl)-4-ethyl-hexanoic acid;
2-Aminomethyl-6-(3-fluoro-phenyl)-4-ethyl-hexanoic acid;
2-Aminomethyl-6-(4-fluoro-phenyl)-4-ethyl-hexanoic acid;
2-Aminomethyl-6-(2,3-difluoro-phenyl)-4-ethyl-hexanoic acid;
2-Aminomethyl-6-(2,4-difluoro-phenyl)-4-ethyl-hexanoic acid;
2-Aminomethyl-6-(2,5-difluoro-phenyl)-4-ethyl-hexanoic acid;
2-Aminomethyl-6-(2,6-difluoro-phenyl)-4-ethyl-hexanoic acid;
2-Aminomethyl-6-(3,4-difluoro-phenyl)-4-ethyl-hexanoic acid;
2-Aminomethyl-6-(3,5-difluoro-phenyl)-4-ethyl-hexanoic acid;
2-Aminomethyl-4-ethyl-6-(2,3,4-trifluoro-phenyl)-hexanoic acid;
2-Aminomethyl-4-ethyl-6-(2,3,5-trifluoro-phenyl)-hexanoic acid;
2-Aminomethyl-4-ethyl-6-(2,3,6-trifluoro-phenyl)-hexanoic acid;
2-Aminomethyl-4-ethyl-6-(2,4,6-trifluoro-phenyl)-hexanoic acid;
2-Aminomethyl-4-ethyl-6-(2,3,4,5-tetrafluoro-phenyl)-hexanoic acid;
2-Aminomethyl-4-ethyl-6-(2,3,4,6-tetrafluoro-phenyl)-hexanoic acid;
2-Aminomethyl-4-ethyl-6-(2,3,5,6-tetrafluoro-phenyl)-hexanoic acid;
2-Aminomethyl-4-ethyl-6-pentafluorophenyl-hexanoic acid;
2-Aminomethyl-7-(2-fluoro-phenyl)-4-methyl-heptanoic acid;
2-Aminomethyl-7-(3-fluoro-phenyl)-4-methyl-heptanoic acid;
2-Aminomethyl-7-(4-fluoro-phenyl)-4-methyl-heptanoic acid;
2-Aminomethyl-7-(2,3-difluoro-phenyl)-4-methyl-heptanoic acid;
2-Aminomethyl-7-(2,4-difluoro-phenyl)-4-methyl-heptanoic acid;
2-Aminomethyl-7-(2,5-difluoro-phenyl)-4-methyl-heptanoic acid;
2-Aminomethyl-7-(2,6-difluoro-phenyl)-4-methyl-heptanoic acid;
2-Aminomethyl-7-(3,4-difluoro-phenyl)-4-methyl-heptanoic acid;
2-Aminomethyl-7-(3,5-difluoro-phenyl)-4-methyl-heptanoic acid;
2-Aminomethyl-4-methyl-7-(2,3,4-trifluoro-phenyl)-heptanoic acid;

2-Aminomethyl-4-methyl-7-(2,3,5-trifluoro-phenyl)-heptanoic acid;
2-Aminomethyl-4-methyl-7-(2,3,6-trifluoro-phenyl)-heptanoic acid;
2-Aminomethyl-4-methyl-7-(2,4,6-trifluoro-phenyl)-heptanoic acid;
2-Aminomethyl-4-methyl-7-(2,3,4,5-tetrafluoro-phenyl)-heptanoic acid;
2-Aminomethyl-4-methyl-7-(2,3,4,6-tetrafluoro-phenyl)-heptanoic acid;
2-Aminomethyl-4-methyl-7-(2,3,5,6-tetrafluoro-phenyl)-heptanoic acid;
2-Aminomethyl-4-methyl-7-pentafluorophenyl-heptanoic acid;
2-Aminomethyl-7-(2-fluoro-phenyl)-4-ethyl-heptanoic acid;
2-Aminomethyl-7-(3-fluoro-phenyl)-4-ethyl-heptanoic acid;
2-Aminomethyl-7-(4-fluoro-phenyl)-4-ethyl-heptanoic acid;
2-Aminomethyl-7-(2,3-difluoro-phenyl)-4-ethyl-heptanoic acid;
2-Aminomethyl-7-(2,4-difluoro-phenyl)-4-ethyl-heptanoic acid;
2-Aminomethyl-7-(2,5-difluoro-phenyl)-4-ethyl-heptanoic acid;
2-Aminomethyl-7-(2,6-difluoro-phenyl)-4-ethyl-heptanoic acid;
2-Aminomethyl-7-(3,4-difluoro-phenyl)-4-ethyl-heptanoic acid;
2-Aminomethyl-7-(3,5-difluoro-phenyl)-4-ethyl-heptanoic acid;
2-Aminomethyl-4-ethyl-7-(2,3,4-trifluoro-phenyl)-heptanoic acid;
2-Aminomethyl-4-ethyl-7-(2,3,5-trifluoro-phenyl)-heptanoic acid;
2-Aminomethyl-4-ethyl-7-(2,3,6-trifluoro-phenyl)-heptanoic acid;
2-Aminomethyl-4-ethyl-7-(2,4,6-trifluoro-phenyl)-heptanoic acid;
2-Aminomethyl-4-ethyl-7-(2,3,4,5-tetrafluoro-phenyl)-heptanoic acid;
2-Aminomethyl-4-ethyl-7-(2,3,4,6-tetrafluoro-phenyl)-heptanoic acid;
2-Aminomethyl-4-ethyl-7-(2,3,5,6-tetrafluoro-phenyl)-heptanoic acid;
2-Aminomethyl-4-ethyl-7-pentafluorophenyl-heptanoic acid;
2-Aminomethyl-4-(2-chloro-phenyl)-pentanoic acid;
2-Aminomethyl-4-(3-chloro-phenyl)-pentanoic acid;
2-Aminomethyl-4-(4-chloro-phenyl)-pentanoic acid;
2-Aminomethyl-4-(2,3-dichloro-phenyl)-pentanoic acid;
2-Aminomethyl-4-(2,4-dichloro-phenyl)-pentanoic acid;
2-Aminomethyl-4-(2,5-dichloro-phenyl)-pentanoic acid;
2-Aminomethyl-4-(2,6-dichloro-phenyl)-pentanoic acid;
2-Aminomethyl-4-(3,4-dichloro-phenyl)-pentanoic acid;
2-Aminomethyl-4-(3,5-dichloro-phenyl)-pentanoic acid;
2-Aminomethyl-4-(2,3,4-trichloro-phenyl)-pentanoic acid;
2-Aminomethyl-4-(2,3,5-trichloro-phenyl)-pentanoic acid;
2-Aminomethyl-4-(2,3,6-trichloro-phenyl)-pentanoic acid;
2-Aminomethyl-4-(2,4,6-trichloro-phenyl)-pentanoic acid;
2-Aminomethyl-4-(2,3,4,5-tetrachloro-phenyl)-pentanoic acid;
2-Aminomethyl-4-(2,3,4,6-tetrachloro-phenyl)-pentanoic acid;
2-Aminomethyl-4-(2,3,5,6-tetrachloro-phenyl)-pentanoic acid;
2-Aminomethyl-4-pentachlorophenyl-pentanoic acid;
2-Aminomethyl-4-(2-chloro-phenyl)-hexanoic acid;
2-Aminomethyl-4-(3-chloro-phenyl)-hexanoic acid;
2-Aminomethyl-4-(4-chloro-phenyl)-hexanoic acid;
2-Aminomethyl-4-(2,3-dichloro-phenyl)-hexanoic acid;
2-Aminomethyl-4-(2,4-dichloro-phenyl)-hexanoic acid;
2-Aminomethyl-4-(2,5-dichloro-phenyl)-hexanoic acid;
2-Aminomethyl-4-(2,6-dichloro-phenyl)-hexanoic acid;
2-Aminomethyl-4-(3,4-dichloro-phenyl)-hexanoic acid;
2-Aminomethyl-4-(3,5-dichloro-phenyl)-hexanoic acid;
2-Aminomethyl-4-(2,3,4-trichloro-phenyl)-hexanoic acid;
2-Aminomethyl-4-(2,3,5-trichloro-phenyl)-hexanoic acid;
2-Aminomethyl-4-(2,3,6-trichloro-phenyl)-hexanoic acid;
2-Aminomethyl-4-(2,4,6-trichloro-phenyl)-hexanoic acid;
2-Aminomethyl-4-(2,3,4,5-tetrachloro-phenyl)-hexanoic acid;
2-Aminomethyl-4-(2,3,4,6-tetrachloro-phenyl)-hexanoic acid;
2-Aminomethyl-4-(2,3,5,6-tetrachloro-phenyl)-hexanoic acid;
2-Aminomethyl-4-pentachlorophenyl-hexanoic acid;
2-Aminomethyl-5-(2-chloro-phenyl)-4-methyl-pentanoic acid;
2-Aminomethyl-5-(3-chloro-phenyl)-4-methyl-pentanoic acid;
2-Aminomethyl-5-(4-chloro-phenyl)-4-methyl-pentanoic acid;
2-Aminomethyl-5-(2,3-dichloro-phenyl)-4-methyl-pentanoic acid;
2-Aminomethyl-5-(2,4-dichloro-phenyl)-4-methyl-pentanoic acid;
2-Aminomethyl-5-(2,5-dichloro-phenyl)-4-methyl-pentanoic acid;
2-Aminomethyl-5-(2,6-dichloro-phenyl)-4-methyl-pentanoic acid;
2-Aminomethyl-5-(3,4-dichloro-phenyl)-4-methyl-pentanoic acid;
2-Aminomethyl-5-(3,5-dichloro-phenyl)-4-methyl-pentanoic acid;
2-Aminomethyl-4-methyl-5-(2,3,4-trichloro-phenyl)-pentanoic acid;
2-Aminomethyl-4-methyl-5-(2,3,5-trichloro-phenyl)-pentanoic acid;
2-Aminomethyl-4-methyl-5-(2,3,6-trichloro-phenyl)-pentanoic acid;
2-Aminomethyl-4-methyl-5-(2,4,6-trichloro-phenyl)-pentanoic acid;
2-Aminomethyl-4-methyl-5-(2,3,4,5-tetrachloro-phenyl)-pentanoic acid;
2-Aminomethyl-4-methyl-5-(2,3,4,6-tetrachloro-phenyl)-pentanoic acid;
2-Aminomethyl-4-methyl-5-(2,3,5,6-tetrachloro-phenyl)-pentanoic acid;
2-Aminomethyl-4-methyl-5-pentachlorophenyl-pentanoic acid;
2-Aminomethyl-5-(2-chloro-phenyl)-4-methyl-hexanoic acid;
2-Aminomethyl-5-(3-chloro-phenyl)-4-methyl-hexanoic acid;
2-Aminomethyl-5-(4-chloro-phenyl)-4-methyl-hexanoic acid;
2-Aminomethyl-5-(2,3-dichloro-phenyl)-4-methyl-hexanoic acid;
2-Aminomethyl-5-(2,4-dichloro-phenyl)-4-methyl-hexanoic acid;
2-Aminomethyl-5-(2,5-dichloro-phenyl)-4-methyl-hexanoic acid;

2-Aminomethyl-5-(2,6-dichloro-phenyl)-4-methyl-hexanoic acid;
2-Aminomethyl-5-(3,4-dichloro-phenyl)-4-methyl-hexanoic acid;
2-Aminomethyl-5-(3,5-dichloro-phenyl)-4-methyl-hexanoic acid;
2-Aminomethyl-4-methyl-5-(2,3,4-trichloro-phenyl)-hexanoic acid;
2-Aminomethyl-4-methyl-5-(2,3,5-trichloro-phenyl)-hexanoic acid;
2-Aminomethyl-4-methyl-5-(2,3,6-trichloro-phenyl)-hexanoic acid;
2-Aminomethyl-4-methyl-5-(2,4,6-trichloro-phenyl)-hexanoic acid;
2-Aminomethyl-4-methyl-5-(2,3,4,5-tetrachloro-phenyl)-hexanoic acid;
2-Aminomethyl-4-methyl-5-(2,3,4,6-tetrachloro-phenyl)-hexanoic acid;
2-Aminomethyl-4-methyl-5-(2,3,5,6-tetrachloro-phenyl)-hexanoic acid;
2-Aminomethyl-4-methyl-5-pentachlorophenyl-hexanoic acid;
2-Aminomethyl-5-(2-chloro-phenyl)-4-methyl-hexanoic acid;
2-Aminomethyl-5-(3-chloro-phenyl)-4-methyl-hexanoic acid;
2-Aminomethyl-5-(4-chloro-phenyl)-4-methyl-hexanoic acid;
2-Aminomethyl-5-(2,3-dichloro-phenyl)-4-methyl-hexanoic acid;
2-Aminomethyl-5-(2,4-dichloro-phenyl)-4-methyl-hexanoic acid;
2-Aminomethyl-5-(2,5-dichloro-phenyl)-4-methyl-hexanoic acid;
2-Aminomethyl-5-(2,6-dichloro-phenyl)-4-methyl-hexanoic acid;
2-Aminomethyl-5-(3,4-dichloro-phenyl)-4-methyl-hexanoic acid;
2-Aminomethyl-5-(3,5-dichloro-phenyl)-4-methyl-hexanoic acid;
2-Aminomethyl-4-methyl-5-(2,3,4-trichloro-phenyl)-hexanoic acid;
2-Aminomethyl-4-methyl-5-(2,3,5-trichloro-phenyl)-hexanoic acid;
2-Aminomethyl-4-methyl-5-(2,3,6-trichloro-phenyl)-hexanoic acid;
2-Aminomethyl-4-methyl-5-(2,4,6-trichloro-phenyl)-hexanoic acid;
2-Aminomethyl-4-methyl-5-(2,3,4,5-tetrachloro-phenyl)-hexanoic acid;
2-Aminomethyl-4-methyl-5-(2,3,4,6-tetrachloro-phenyl)-hexanoic acid;
2-Aminomethyl-4-methyl-5-(2,3,5,6-tetrachloro-phenyl)-hexanoic acid;
2-Aminomethyl-4-methyl-5-pentachlorophenyl-hexanoic acid;
2-Aminomethyl-5-(2-chloro-phenyl)-4-ethyl-pentanoic acid;
2-Aminomethyl-5-(3-chloro-phenyl)-4-ethyl-pentanoic acid;
2-Aminomethyl-5-(4-chloro-phenyl)-4-ethyl-pentanoic acid;
2-Aminomethyl-5-(2,3-dichloro-phenyl)-4-ethyl-pentanoic acid;
2-Aminomethyl-5-(2,4-dichloro-phenyl)-4-ethyl-pentanoic acid;
2-Aminomethyl-5-(2,5-dichloro-phenyl)-4-ethyl-pentanoic acid;
2-Aminomethyl-5-(2,6-dichloro-phenyl)-4-ethyl-pentanoic acid;
2-Aminomethyl-5-(3,4-dichloro-phenyl)-4-ethyl-pentanoic acid;
2-Aminomethyl-5-(3,5-dichloro-phenyl)-4-ethyl-pentanoic acid;
2-Aminomethyl-4-ethyl-5-(2,3,4-trichloro-phenyl)-pentanoic acid;
2-Aminomethyl-4-ethyl-5-(2,3,5-trichloro-phenyl)-pentanoic acid;
2-Aminomethyl-4-ethyl-5-(2,3,6-trichloro-phenyl)-pentanoic acid;
2-Aminomethyl-4-ethyl-5-(2,4,6-trichloro-phenyl)-pentanoic acid;
2-Aminomethyl-4-ethyl-5-(2,3,4,5-tetrachloro-phenyl)-pentanoic acid;
2-Aminomethyl-4-ethyl-5-(2,3,4,6-tetrachloro-phenyl)-pentanoic acid;
2-Aminomethyl-4-ethyl-5-(2,3,5,6-tetrachloro-phenyl)-pentanoic acid;
2-Aminomethyl-4-ethyl-5-pentachlorophenyl-pentanoic acid;
2-Aminomethyl-6-(2-chloro-phenyl)-4-ethyl-hexanoic acid;
2-Aminomethyl-6-(3-chloro-phenyl)-4-ethyl-hexanoic acid;
2-Aminomethyl-6-(4-chloro-phenyl)-4-ethyl-hexanoic acid;
2-Aminomethyl-6-(2,3-dichloro-phenyl)-4-ethyl-hexanoic acid;
2-Aminomethyl-6-(2,4-dichloro-phenyl)-4-ethyl-hexanoic acid;
2-Aminomethyl-6-(2,5-dichloro-phenyl)-4-ethyl-hexanoic acid;
2-Aminomethyl-6-(2,6-dichloro-phenyl)-4-ethyl-hexanoic acid;
2-Aminomethyl-6-(3,4-dichloro-phenyl)-4-ethyl-hexanoic acid;
2-Aminomethyl-6-(3,5-dichloro-phenyl)-4-ethyl-hexanoic acid;
2-Aminomethyl-4-ethyl-6-(2,3,4-trichloro-phenyl)-hexanoic acid;
2-Aminomethyl-4-ethyl-6-(2,3,5-trichloro-phenyl)-hexanoic acid;
2-Aminomethyl-4-ethyl-6-(2,3,6-trichloro-phenyl)-hexanoic acid;
2-Aminomethyl-4-ethyl-6-(2,4,6-trichloro-phenyl)-hexanoic acid;
2-Aminomethyl-4-ethyl-6-(2,3,4,5-tetrachloro-phenyl)-hexanoic acid;
2-Aminomethyl-4-ethyl-6-(2,3,4,6-tetrachloro-phenyl)-hexanoic acid;
2-Aminomethyl-4-ethyl-6-(2,3,5,6-tetrachloro-phenyl)-hexanoic acid;
2-Aminomethyl-4-ethyl-6-pentachlorophenyl-hexanoic acid;
2-Aminomethyl-7-(2-chloro-phenyl)-4-methyl-heptanoic acid;
2-Aminomethyl-7-(3-chloro-phenyl)-4-methyl-heptanoic acid;
2-Aminomethyl-7-(4-chloro-phenyl)-4-methyl-heptanoic acid;
2-Aminomethyl-7-(2,3-dichloro-phenyl)-4-methyl-heptanoic acid;
2-Aminomethyl-7-(2,4-dichloro-phenyl)-4-methyl-heptanoic acid;
2-Aminomethyl-7-(2,5-dichloro-phenyl)-4-methyl-heptanoic acid;

2-Aminomethyl-7-(2,6-dichloro-phenyl)-4-methyl-heptanoic acid;
2-Aminomethyl-7-(3,4-dichloro-phenyl)-4-methyl-heptanoic acid;
2-Aminomethyl-7-(3,5-dichloro-phenyl)-4-methyl-heptanoic acid;
2-Aminomethyl-4-methyl-7-(2,3,4-trichloro-phenyl)-heptanoic acid;
2-Aminomethyl-4-methyl-7-(2,3,5-trichloro-phenyl)-heptanoic acid;
2-Aminomethyl-4-methyl-7-(2,3,6-trichloro-phenyl)-heptanoic acid;
2-Aminomethyl-4-methyl-7-(2,4,6-trichloro-phenyl)-heptanoic acid;
2-Aminomethyl-4-methyl-7-(2,3,4,5-tetrachloro-phenyl)-heptanoic acid;
2-Aminomethyl-4-methyl-7-(2,3,4,6-tetrachloro-phenyl)-heptanoic acid;
2-Aminomethyl-4-methyl-7-(2,3,5,6-tetrachloro-phenyl)-heptanoic acid;
2-Aminomethyl-4-methyl-7-pentachlorophenyl-heptanoic acid;
2-Aminomethyl-7-(2-chloro-phenyl)-4-ethyl-heptanoic acid;
2-Aminomethyl-7-(3-chloro-phenyl)-4-ethyl-heptanoic acid;
2-Aminomethyl-7-(4-chloro-phenyl)-4-ethyl-heptanoic acid;
2-Aminomethyl-7-(2,3-dichloro-phenyl)-4-ethyl-heptanoic acid;
2-Aminomethyl-7-(2,4-dichloro-phenyl)-4-ethyl-heptanoic acid;
2-Aminomethyl-7-(2,5-dichloro-phenyl)-4-ethyl-heptanoic acid;
2-Aminomethyl-7-(2,6-dichloro-phenyl)-4-ethyl-heptanoic acid;
2-Aminomethyl-7-(3,4-dichloro-phenyl)-4-ethyl-heptanoic acid;
2-Aminomethyl-7-(3,5-dichloro-phenyl)-4-ethyl-heptanoic acid;
2-Aminomethyl-4-ethyl-7-(2,3,4-trichloro-phenyl)-heptanoic acid;
2-Aminomethyl-4-ethyl-7-(2,3,5-trichloro-phenyl)-heptanoic acid;
2-Aminomethyl-4-ethyl-7-(2,3,6-trichloro-phenyl)-heptanoic acid;
2-Aminomethyl-4-ethyl-7-(2,4,6-trichloro-phenyl)-heptanoic acid;
2-Aminomethyl-4-ethyl-7-(2,3,4,5-tetrachloro-phenyl)-heptanoic acid;
2-Aminomethyl-4-ethyl-7-(2,3,4,6-tetrachloro-phenyl)-heptanoic acid;
2-Aminomethyl-4-ethyl-7-(2,3,5,6-tetrachloro-phenyl)-heptanoic acid;
2-Aminomethyl-4-ethyl-7-pentachlorophenyl-heptanoic acid;
2-Aminomethyl-4-(2-methoxy-phenyl)-pentanoic acid;
2-Aminomethyl-4-(3-methoxy-phenyl)-pentanoic acid;
2-Aminomethyl-4-(4-methoxy-phenyl)-pentanoic acid;
2-Aminomethyl-4-(2,3-dimethoxy-phenyl)-pentanoic acid;
2-Aminomethyl-4-(2,4-dimethoxy-phenyl)-pentanoic acid;
2-Aminomethyl-4-(2,5-dimethoxy-phenyl)-pentanoic acid;
2-Aminomethyl-4-(2,6-dimethoxy-phenyl)-pentanoic acid;
2-Aminomethyl-4-(3,4-dimethoxy-phenyl)-pentanoic acid;
2-Aminomethyl-4-(3,5-dimethoxy-phenyl)-pentanoic acid;
2-Aminomethyl-4-(2,3,4-trimethoxy-phenyl)-pentanoic acid;
2-Aminomethyl-4-(2,3,5-trimethoxy-phenyl)-pentanoic acid;
2-Aminomethyl-4-(2,3,6-trimethoxy-phenyl)-pentanoic acid;
2-Aminomethyl-4-(2,4,6-trimethoxy-phenyl)-pentanoic acid;
2-Aminomethyl-4-(2-methoxy-phenyl)-hexanoic acid;
2-Aminomethyl-4-(3-methoxy-phenyl)-hexanoic acid;
2-Aminomethyl-4-(4-methoxy-phenyl)-hexanoic acid;
2-Aminomethyl-4-(2,3-dimethoxy-phenyl)-hexanoic acid;
2-Aminomethyl-4-(2,4-dimethoxy-phenyl)-hexanoic acid;
2-Aminomethyl-4-(2,5-dimethoxy-phenyl)-hexanoic acid;
2-Aminomethyl-4-(2,6-dimethoxy-phenyl)-hexanoic acid;
2-Aminomethyl-4-(3,4-dimethoxy-phenyl)-hexanoic acid;
2-Aminomethyl-4-(3,5-dimethoxy-phenyl)-hexanoic acid;
2-Aminomethyl-4-(2,3,4-trimethoxy-phenyl)-hexanoic acid;
2-Aminomethyl-4-(2,3,5-trimethoxy-phenyl)-hexanoic acid;
2-Aminomethyl-4-(2,3,6-trimethoxy-phenyl)-hexanoic acid;
2-Aminomethyl-4-(2,4,6-trimethoxy-phenyl)-hexanoic acid;
2-Aminomethyl-5-(2-methoxy-phenyl)-4-methyl-pentanoic acid;
2-Aminomethyl-5-(3-methoxy-phenyl)-4-methyl-pentanoic acid;
2-Aminomethyl-5-(4-methoxy-phenyl)-4-methyl-pentanoic acid;
2-Aminomethyl-5-(2,3-dimethoxy-phenyl)-4-methyl-pentanoic acid;
2-Aminomethyl-5-(2,4-dimethoxy-phenyl)-4-methyl-pentanoic acid;
2-Aminomethyl-5-(2,5-dimethoxy-phenyl)-4-methyl-pentanoic acid;
2-Aminomethyl-5-(2,6-dimethoxy-phenyl)-4-methyl-pentanoic acid;
2-Aminomethyl-5-(3,4-dimethoxy-phenyl)-4-methyl-pentanoic acid;
2-Aminomethyl-5-(3,5-dimethoxy-phenyl)-4-methyl-pentanoic acid;
2-Aminomethyl-4-methyl-5-(2,3,4-trimethoxy-phenyl)-pentanoic acid;
2-Aminomethyl-4-methyl-5-(2,3,5-trimethoxy-phenyl)-pentanoic acid;
2-Aminomethyl-4-methyl-5-(2,3,6-trimethoxy-phenyl)-pentanoic acid;
2-Aminomethyl-4-methyl-5-(2,4,6-trimethoxy-phenyl)-pentanoic acid;
2-Aminomethyl-5-(2-methoxy-phenyl)-4-methyl-hexanoic acid;
2-Aminomethyl-5-(3-methoxy-phenyl)-4-methyl-hexanoic acid;
2-Aminomethyl-5-(4-methoxy-phenyl)-4-methyl-hexanoic acid;
2-Aminomethyl-5-(2,3-dimethoxy-phenyl)-4-methyl-hexanoic acid;
2-Aminomethyl-5-(2,4-dimethoxy-phenyl)-4-methyl-hexanoic acid;
2-Aminomethyl-5-(2,5-dimethoxy-phenyl)-4-methyl-hexanoic acid;
2-Aminomethyl-5-(2,6-dimethoxy-phenyl)-4-methyl-hexanoic acid;
2-Aminomethyl-5-(3,4-dimethoxy-phenyl)-4-methyl-hexanoic acid;
2-Aminomethyl-5-(3,5-dimethoxy-phenyl)-4-methyl-hexanoic acid;

2-Aminomethyl-4-methyl-5-(2,3,4-trimethoxy-phenyl)-hexanoic acid;
2-Aminomethyl-4-methyl-5-(2,3,5-trimethoxy-phenyl)-hexanoic acid;
2-Aminomethyl-4-methyl-5-(2,3,6-trimethoxy-phenyl)-hexanoic acid;
2-Aminomethyl-4-methyl-5-(2,4,6-trimethoxy-phenyl)-hexanoic acid;
2-Aminomethyl-6-(2-methoxy-phenyl)-4-methyl-hexanoic acid;
2-Aminomethyl-6-(3-methoxy-phenyl)-4-methyl-hexanoic acid;
2-Aminomethyl-6-(4-methoxy-phenyl)-4-methyl-hexanoic acid;
2-Aminomethyl-6-(2,3-dimethoxy-phenyl)-4-methyl-hexanoic acid;
2-Aminomethyl-6-(2,4-dimethoxy-phenyl)-4-methyl-hexanoic acid;
2-Aminomethyl-6-(2,5-dimethoxy-phenyl)-4-methyl-hexanoic acid;
2-Aminomethyl-6-(2,6-dimethoxy-phenyl)-4-methyl-hexanoic acid;
2-Aminomethyl-6-(3,4-dimethoxy-phenyl)-4-methyl-hexanoic acid;
2-Aminomethyl-6-(3,5-dimethoxy-phenyl)-4-methyl-hexanoic acid;
2-Aminomethyl-4-methyl-6-(2,3,4-trimethoxy-phenyl)-hexanoic acid;
2-Aminomethyl-4-methyl-6-(2,3,5-trimethoxy-phenyl)-hexanoic acid;
2-Aminomethyl-4-methyl-6-(2,3,6-trimethoxy-phenyl)-hexanoic acid;
2-Aminomethyl-4-methyl-6-(2,4,6-trimethoxy-phenyl)-hexanoic acid;
2-Aminomethyl-5-(2-methoxy-phenyl)-4-ethyl-pentanoic acid;
2-Aminomethyl-5-(3-methoxy-phenyl)-4-ethyl-pentanoic acid;
2-Aminomethyl-5-(4-methoxy-phenyl)-4-ethyl-pentanoic acid;
2-Aminomethyl-5-(2,3-dimethoxy-phenyl)-4-ethyl-pentanoic acid;
2-Aminomethyl-5-(2,4-dimethoxy-phenyl)-4-ethyl-pentanoic acid;
2-Aminomethyl-5-(2,5-dimethoxy-phenyl)-4-ethyl-pentanoic acid;
2-Aminomethyl-5-(2,6-dimethoxy-phenyl)-4-ethyl-pentanoic acid;
2-Aminomethyl-5-(3,4-dimethoxy-phenyl)-4-ethyl-pentanoic acid;
2-Aminomethyl-5-(3,5-dimethoxy-phenyl)-4-ethyl-pentanoic acid;
2-Aminomethyl-4-ethyl-5-(2,3,4-trimethoxy-phenyl)-pentanoic acid;
2-Aminomethyl-4-ethyl-5-(2,3,5-trimethoxy-phenyl)-pentanoic acid;
2-Aminomethyl-4-ethyl-5-(2,3,6-trimethoxy-phenyl)-pentanoic acid;
2-Aminomethyl-4-ethyl-5-(2,4,6-trimethoxy-phenyl)-pentanoic acid;
2-Aminomethyl-4-ethyl-5-(2,3,4,5-tetramethoxy-phenyl)-pentanoic acid;
2-Aminomethyl-4-ethyl-5-(2,3,4,6-tetramethoxy-phenyl)-pentanoic acid;
2-Aminomethyl-4-ethyl-5-(2,3,5,6-tetramethoxy-phenyl)-pentanoic acid;
2-Aminomethyl-4-ethyl-5-pentamethoxyphenyl-pentanoic acid;
2-Aminomethyl-6-(2-methoxy-phenyl)-4-ethyl-hexanoic acid;
2-Aminomethyl-6-(3-methoxy-phenyl)-4-ethyl-hexanoic acid;
2-Aminomethyl-6-(4-methoxy-phenyl)-4-ethyl-hexanoic acid;
2-Aminomethyl-6-(2,3-dimethoxy-phenyl)-4-ethyl-hexanoic acid;
2-Aminomethyl-6-(2,4-dimethoxy-phenyl)-4-ethyl-hexanoic acid;
2-Aminomethyl-6-(2,5-dimethoxy-phenyl)-4-ethyl-hexanoic acid;
2-Aminomethyl-6-(2,6-dimethoxy-phenyl)-4-ethyl-hexanoic acid;
2-Aminomethyl-6-(3,4-dimethoxy-phenyl)-4-ethyl-hexanoic acid;
2-Aminomethyl-6-(3,5-dimethoxy-phenyl)-4-ethyl-hexanoic acid;
2-Aminomethyl-4-ethyl-6-(2,3,4-trimethoxy-phenyl)-hexanoic acid;
2-Aminomethyl-4-ethyl-6-(2,3,5-trimethoxy-phenyl)-hexanoic acid;
2-Aminomethyl-4-ethyl-6-(2,3,6-trimethoxy-phenyl)-hexanoic acid;
2-Aminomethyl-4-ethyl-6-(2,4,6-trimethoxy-phenyl)-hexanoic acid;
2-Aminomethyl-7-(2-methoxy-phenyl)-4-methyl-heptanoic acid;
2-Aminomethyl-7-(3-methoxy-phenyl)-4-methyl-heptanoic acid;
2-Aminomethyl-7-(4-methoxy-phenyl)-4-methyl-heptanoic acid;
2-Aminomethyl-7-(2,3-dimethoxy-phenyl)-4-methyl-heptanoic acid;
2-Aminomethyl-7-(2,4-dimethoxy-phenyl)-4-methyl-heptanoic acid;
2-Aminomethyl-7-(2,5-dimethoxy-phenyl)-4-methyl-heptanoic acid;
2-Aminomethyl-7-(2,6-dimethoxy-phenyl)-4-methyl-heptanoic acid;
2-Aminomethyl-7-(3,4-dimethoxy-phenyl)-4-methyl-heptanoic acid;
2-Aminomethyl-7-(3,5-dimethoxy-phenyl)-4-methyl-heptanoic acid;
2-Aminomethyl-4-methyl-7-(2,3,4-trimethoxy-phenyl)-heptanoic acid;
2-Aminomethyl-4-methyl-7-(2,3,5-trimethoxy-phenyl)-heptanoic acid;
2-Aminomethyl-4-methyl-7-(2,3,6-trimethoxy-phenyl)-heptanoic acid;
2-Aminomethyl-4-methyl-7-(2,4,6-trimethoxy-phenyl)-heptanoic acid;
2-Aminomethyl-7-(2-methoxy-phenyl)-4-ethyl-heptanoic acid;
2-Aminomethyl-7-(3-methoxy-phenyl)-4-ethyl-heptanoic acid;
2-Aminomethyl-7-(4-methoxy-phenyl)-4-ethyl-heptanoic acid;
2-Aminomethyl-7-(2,3-dimethoxy-phenyl)-4-ethyl-heptanoic acid;
2-Aminomethyl-7-(2,4-dimethoxy-phenyl)-4-ethyl-heptanoic acid;
2-Aminomethyl-7-(2,5-dimethoxy-phenyl)-4-ethyl-heptanoic acid;

2-Aminomethyl-7-(2,6-dimethoxy-phenyl)-4-ethyl-heptanoic acid;
2-Aminomethyl-7-(3,4-dimethoxy-phenyl)-4-ethyl-heptanoic acid;
2-Aminomethyl-7-(3,5-dimethoxy-phenyl)-4-ethyl-heptanoic acid;
2-Aminomethyl-4-ethyl-7-(2,3,4-trimethoxy-phenyl)-heptanoic acid;
2-Aminomethyl-4-ethyl-7-(2,3,5-trimethoxy-phenyl)-heptanoic acid;
2-Aminomethyl-4-ethyl-7-(2,3,6-trimethoxy-phenyl)-heptanoic acid;
2-Aminomethyl-4-ethyl-7-(2,4,6-trimethoxy-phenyl)-heptanoic acid;
2-Aminomethyl-4-(2-trifluoromethyl-phenyl)-pentanoic acid;
2-Aminomethyl-4-(3-trifluoromethyl-phenyl)-pentanoic acid;
2-Aminomethyl-4-(4-trifluoromethyl-phenyl)-pentanoic acid;
2-Aminomethyl-4-(2,3-di-trifluoromethyl-phenyl)-pentanoic acid;
2-Aminomethyl-4-(2,4-di-trifluoromethyl-phenyl)-pentanoic acid;
2-Aminomethyl-4-(2,5-di-trifluoromethyl-phenyl)-pentanoic acid;
2-Aminomethyl-4-(2,6-di-trifluoromethyl-phenyl)-pentanoic acid;
2-Aminomethyl-4-(3,4-di-trifluoromethyl-phenyl)-pentanoic acid;
2-Aminomethyl-4-(3,5-di-trifluoromethyl-phenyl)-pentanoic acid;
2-Aminomethyl-4-(2,3,4-tri-trifluoromethyl-phenyl)-pentanoic acid;
2-Aminomethyl-4-(2,3,5-tri-trifluoromethyl-phenyl)-pentanoic acid;
2-Aminomethyl-4-(2,3,6-tri-trifluoromethyl-phenyl)-pentanoic acid;
2-Aminomethyl-4-(2,4,6-tri-trifluoromethyl-phenyl)-pentanoic acid;
2-Aminomethyl-4-(2-trifluoromethyl-phenyl)-hexanoic acid;
2-Aminomethyl-4-(3-trifluoromethyl-phenyl)-hexanoic acid;
2-Aminomethyl-4-(4-trifluoromethyl-phenyl)-hexanoic acid;
2-Aminomethyl-4-(2,3-di-trifluoromethyl-phenyl)-hexanoic acid;
2-Aminomethyl-4-(2,4-di-trifluoromethyl-phenyl)-hexanoic acid;
2-Aminomethyl-4-(2,5-di-trifluoromethyl-phenyl)-hexanoic acid;
2-Aminomethyl-4-(2,6-di-trifluoromethyl-phenyl)-hexanoic acid;
2-Aminomethyl-4-(3,4-di-trifluoromethyl-phenyl)-hexanoic acid;
2-Aminomethyl-4-(3,5-di-trifluoromethyl-phenyl)-hexanoic acid;
2-Aminomethyl-4-(2,3,4-tri-trifluoromethyl-phenyl)-hexanoic acid;
2-Aminomethyl-4-(2,3,5-tri-trifluoromethyl-phenyl)-hexanoic acid;
2-Aminomethyl-4-(2,3,6-tri-trifluoromethyl-phenyl)-hexanoic acid;
2-Aminomethyl-4-(2,4,6-tri-trifluoromethyl-phenyl)-hexanoic acid;
2-Aminomethyl-5-(2-trifluoromethyl-phenyl)-4-methyl-pentanoic acid;
2-Aminomethyl-5-(3-trifluoromethyl-phenyl)-4-methyl-pentanoic acid;
2-Aminomethyl-5-(4-trifluoromethyl-phenyl)-4-methyl-pentanoic acid;
2-Aminomethyl-5-(2,3-di-trifluoromethyl-phenyl)-4-methyl-pentanoic acid;
2-Aminomethyl-5-(2,4-di-trifluoromethyl-phenyl)-4-methyl-pentanoic acid;
2-Aminomethyl-5-(2,5-di-trifluoromethyl-phenyl)-4-methyl-pentanoic acid;
2-Aminomethyl-5-(2,6-di-trifluoromethyl-phenyl)-4-methyl-pentanoic acid;
2-Aminomethyl-5-(3,4-di-trifluoromethyl-phenyl)-4-methyl-pentanoic acid;
2-Aminomethyl-5-(3,5-di-trifluoromethyl-phenyl)-4-methyl-pentanoic acid;
2-Aminomethyl-4-methyl-5-(2,3,4-tri-trifluoromethyl-phenyl)-pentanoic acid;
2-Aminomethyl-4-methyl-5-(2,3,5-tri-trifluoromethyl-phenyl)-pentanoic acid;
2-Aminomethyl-4-methyl-5-(2,3,6-tri-trifluoromethyl-phenyl)-pentanoic acid;
2-Aminomethyl-4-methyl-5-(2,4,6-tri-trifluoromethyl-phenyl)-pentanoic acid;
2-Aminomethyl-5-(2-trifluoromethyl-phenyl)-4-methyl-hexanoic acid;
2-Aminomethyl-5-(3-trifluoromethyl-phenyl)-4-methyl-hexanoic acid;
2-Aminomethyl-5-(4-trifluoromethyl-phenyl)-4-methyl-hexanoic acid;
2-Aminomethyl-5-(2,3-di-trifluoromethyl-phenyl)-4-methyl-hexanoic acid;
2-Aminomethyl-5-(2,4-di-trifluoromethyl-phenyl)-4-methyl-hexanoic acid;
2-Aminomethyl-5-(2,5-di-trifluoromethyl-phenyl)-4-methyl-hexanoic acid;
2-Aminomethyl-5-(2,6-di-trifluoromethyl-phenyl)-4-methyl-hexanoic acid;
2-Aminomethyl-5-(3,4-di-trifluoromethyl-phenyl)-4-methyl-hexanoic acid;
2-Aminomethyl-5-(3,5-di-trifluoromethyl-phenyl)-4-methyl-hexanoic acid;
2-Aminomethyl-4-methyl-5-(2,3,4-tri-trifluoromethyl-phenyl)-hexanoic acid;
2-Aminomethyl-4-methyl-5-(2,3,5-tri-trifluoromethyl-phenyl)-hexanoic acid;
2-Aminomethyl-4-methyl-5-(2,3,6-tri-trifluoromethyl-phenyl)-hexanoic acid;
2-Aminomethyl-4-methyl-5-(2,4,6-tri-trifluoromethyl-phenyl)-hexanoic acid;
2-Aminomethyl-6-(2-trifluoromethyl-phenyl)-4-methyl-hexanoic acid;
2-Aminomethyl-6-(3-trifluoromethyl-phenyl)-4-methyl-hexanoic acid;
2-Aminomethyl-6-(4-trifluoromethyl-phenyl)-4-methyl-hexanoic acid;
2-Aminomethyl-6-(2,3-di-trifluoromethyl-phenyl)-4-methyl-hexanoic acid;
2-Aminomethyl-6-(2,4-di-trifluoromethyl-phenyl)-4-methyl-hexanoic acid;
2-Aminomethyl-6-(2,5-di-trifluoromethyl-phenyl)-4-methyl-hexanoic acid;
2-Aminomethyl-6-(2,6-di-trifluoromethyl-phenyl)-4-methyl-hexanoic acid;

2-Aminomethyl-6-(3,4-di-trifluoromethyl-phenyl)-4-methyl-hexanoic acid;
2-Aminomethyl-6-(3,5-di-trifluoromethyl-phenyl)-4-methyl-hexanoic acid;
2-Aminomethyl-4-methyl-6-(2,3,4-tri-trifluoromethyl-phenyl)-hexanoic acid;
2-Aminomethyl-4-methyl-6-(2,3,5-tri-trifluoromethyl-phenyl)-hexanoic acid;
2-Aminomethyl-4-methyl-6-(2,3,6-tri-trifluoromethyl-phenyl)-hexanoic acid;
2-Aminomethyl-4-methyl-6-(2,4,6-tri-trifluoromethyl-phenyl)-hexanoic acid;
2-Aminomethyl-5-(2-trifluoromethyl-phenyl)-4-ethyl-pentanoic acid;
2-Aminomethyl-5-(3-trifluoromethyl-phenyl)-4-ethyl-pentanoic acid;
2-Aminomethyl-5-(4-trifluoromethyl-phenyl)-4-ethyl-pentanoic acid;
2-Aminomethyl-5-(2,3-di-trifluoromethyl-phenyl)-4-ethyl-pentanoic acid;
2-Aminomethyl-5-(2,4-di-trifluoromethyl-phenyl)-4-ethyl-pentanoic acid;
2-Aminomethyl-5-(2,5-di-trifluoromethyl-phenyl)-4-ethyl-pentanoic acid;
2-Aminomethyl-5-(2,6-di-trifluoromethyl-phenyl)-4-ethyl-pentanoic acid;
2-Aminomethyl-5-(3,4-di-trifluoromethyl-phenyl)-4-ethyl-pentanoic acid;
2-Aminomethyl-5-(3,5-di-trifluoromethyl-phenyl)-4-ethyl-pentanoic acid;
2-Aminomethyl-4-ethyl-5-(2,3,4-tri-trifluoromethyl-phenyl)-pentanoic acid;
2-Aminomethyl-4-ethyl-5-(2,3,5-tri-trifluoromethyl-phenyl)-pentanoic acid;
2-Aminomethyl-4-ethyl-5-(2,3,6-tri-trifluoromethyl-phenyl)-pentanoic acid;
2-Aminomethyl-4-ethyl-5-(2,4,6-tri-trifluoromethyl-phenyl)-pentanoic acid;
2-Aminomethyl-4-ethyl-5-(2,3,4,5-tetra-trifluoromethyl-phenyl)-pentanoic acid;
2-Aminomethyl-4-ethyl-5-(2,3,4,6-tetra-trifluoromethyl-phenyl)-pentanoic acid;
2-Aminomethyl-4-ethyl-5-(2,3,5,6-tetra-trifluoromethyl-phenyl)-pentanoic acid;
2-Aminomethyl-4-ethyl-5-penta-trifluoromethylphenyl-pentanoic acid;
2-Aminomethyl-6-(2-trifluoromethyl-phenyl)-4-ethyl-hexanoic acid;
2-Aminomethyl-6-(3-trifluoromethyl-phenyl)-4-ethyl-hexanoic acid;
2-Aminomethyl-6-(4-trifluoromethyl-phenyl)-4-ethyl-hexanoic acid;
2-Aminomethyl-6-(2,3-di-trifluoromethyl-phenyl)-4-ethyl-hexanoic acid;
2-Aminomethyl-6-(2,4-di-trifluoromethyl-phenyl)-4-ethyl-hexanoic acid;
2-Aminomethyl-6-(2,5-di-trifluoromethyl-phenyl)-4-ethyl-hexanoic acid;
2-Aminomethyl-6-(2,6-di-trifluoromethyl-phenyl)-4-ethyl-hexanoic acid;
2-Aminomethyl-6-(3,4-di-trifluoromethyl-phenyl)-4-ethyl-hexanoic acid;
2-Aminomethyl-6-(3,5-di-trifluoromethyl-phenyl)-4-ethyl-hexanoic acid;
2-Aminomethyl-4-ethyl-6-(2,3,4-tri-trifluoromethyl-phenyl)-hexanoic acid;
2-Aminomethyl-4-ethyl-6-(2,3,5-tri-trifluoromethyl-phenyl)-hexanoic acid;
2-Aminomethyl-4-ethyl-6-(2,3,6-tri-trifluoromethyl-phenyl)-hexanoic acid;
2-Aminomethyl-4-ethyl-6-(2,4,6-tri-trifluoromethyl-phenyl)-hexanoic acid;
2-Aminomethyl-7-(2-trifluoromethyl-phenyl)-4-methyl-heptanoic acid;
2-Aminomethyl-7-(3-trifluoromethyl-phenyl)-4-methyl-heptanoic acid;
2-Aminomethyl-7-(4-trifluoromethyl-phenyl)-4-methyl-heptanoic acid;
2-Aminomethyl-7-(2,3-di-trifluoromethyl-phenyl)-4-methyl-heptanoic acid;
2-Aminomethyl-7-(2,4-di-trifluoromethyl-phenyl)-4-methyl-heptanoic acid;
2-Aminomethyl-7-(2,5-di-trifluoromethyl-phenyl)-4-methyl-heptanoic acid;
2-Aminomethyl-7-(2,6-di-trifluoromethyl-phenyl)-4-methyl-heptanoic acid;
2-Aminomethyl-7-(3,4-di-trifluoromethyl-phenyl)-4-methyl-heptanoic acid;
2-Aminomethyl-7-(3,5-di-trifluoromethyl-phenyl)-4-methyl-heptanoic acid;
2-Aminomethyl-4-methyl-7-(2,3,4-tri-trifluoromethyl-phenyl)-heptanoic acid;
2-Aminomethyl-4-methyl-7-(2,3,5-tri-trifluoromethyl-phenyl)-heptanoic acid;
2-Aminomethyl-4-methyl-7-(2,3,6-tri-trifluoromethyl-phenyl)-heptanoic acid;
2-Aminomethyl-4-methyl-7-(2,4,6-tri-trifluoromethyl-phenyl)-heptanoic acid;
2-Aminomethyl-7-(2-trifluoromethyl-phenyl)-4-ethyl-heptanoic acid;
2-Aminomethyl-7-(3-trifluoromethyl-phenyl)-4-ethyl-heptanoic acid;
2-Aminomethyl-7-(4-trifluoromethyl-phenyl)-4-ethyl-heptanoic acid;
2-Aminomethyl-7-(2,3-di-trifluoromethyl-phenyl)-4-ethyl-heptanoic acid;
2-Aminomethyl-7-(2,4-di-trifluoromethyl-phenyl)-4-ethyl-heptanoic acid;
2-Aminomethyl-7-(2,5-di-trifluoromethyl-phenyl)-4-ethyl-heptanoic acid;
2-Aminomethyl-7-(2,6-di-trifluoromethyl-phenyl)-4-ethyl-heptanoic acid;
2-Aminomethyl-7-(3,4-di-trifluoromethyl-phenyl)-4-ethyl-heptanoic acid;
2-Aminomethyl-7-(3,5-di-trifluoromethyl-phenyl)-4-ethyl-heptanoic acid;
2-Aminomethyl-4-ethyl-7-(2,3,4-tri-trifluoromethyl-phenyl)-heptanoic acid;
2-Aminomethyl-4-ethyl-7-(2,3,5-tri-trifluoromethyl-phenyl)-heptanoic acid;
2-Aminomethyl-4-ethyl-7-(2,3,6-tri-trifluoromethyl-phenyl)-heptanoic acid;
2-Aminomethyl-4-ethyl-7-(2,4,6-tri-trifluoromethyl-phenyl)-heptanoic acid;
2-Aminomethyl-4-(2-trifluoromethoxy-phenyl)-pentanoic acid;
2-Aminomethyl-4-(3-trifluoromethoxy-phenyl)-pentanoic acid;
2-Aminomethyl-4-(4-trifluoromethoxy-phenyl)-pentanoic acid;
2-Aminomethyl-4-(2,3-di-trifluoromethoxy-phenyl)-pentanoic acid;

2-Aminomethyl-4-(2,4-di-trifluoromethoxy-phenyl)-pentanoic acid;
2-Aminomethyl-4-(2,5-di-trifluoromethoxy-phenyl)-pentanoic acid;
2-Aminomethyl-4-(2,6-di-trifluoromethoxy-phenyl)-pentanoic acid;
2-Aminomethyl-4-(3,4-di-trifluoromethoxy-phenyl)-pentanoic acid;
2-Aminomethyl-4-(3,5-di-trifluoromethoxy-phenyl)-pentanoic acid;
2-Aminomethyl-4-(2,3,4-tri-trifluoromethoxy-phenyl)-pentanoic acid;
2-Aminomethyl-4-(2,3,5-tri-trifluoromethoxy-phenyl)-pentanoic acid;
2-Aminomethyl-4-(2,3,6-tri-trifluoromethoxy-phenyl)-pentanoic acid;
2-Aminomethyl-4-(2,4,6-tri-trifluoromethoxy-phenyl)-pentanoic acid;
2-Aminomethyl-4-(2-trifluoromethoxy-phenyl)-hexanoic acid;
2-Aminomethyl-4-(3-trifluoromethoxy-phenyl)-hexanoic acid;
2-Aminomethyl-4-(4-trifluoromethoxy-phenyl)-hexanoic acid;
2-Aminomethyl-4-(2,3-di-trifluoromethoxy-phenyl)-hexanoic acid;
2-Aminomethyl-4-(2,4-di-trifluoromethoxy-phenyl)-hexanoic acid;
2-Aminomethyl-4-(2,5-di-trifluoromethoxy-phenyl)-hexanoic acid;
2-Aminomethyl-4-(2,6-di-trifluoromethoxy-phenyl)-hexanoic acid;
2-Aminomethyl-4-(3,4-di-trifluoromethoxy-phenyl)-hexanoic acid;
2-Aminomethyl-4-(3,5-di-trifluoromethoxy-phenyl)-hexanoic acid;
2-Aminomethyl-4-(2,3,4-tri-trifluoromethoxy-phenyl)-hexanoic acid;
2-Aminomethyl-4-(2,3,5-tri-trifluoromethoxy-phenyl)-hexanoic acid;
2-Aminomethyl-4-(2,3,6-tri-trifluoromethoxy-phenyl)-hexanoic acid;
2-Aminomethyl-4-(2,4,6-tri-trifluoromethoxy-phenyl)-hexanoic acid;
2-Aminomethyl-5-(2-trifluoromethoxy-phenyl)-4-methyl-pentanoic acid;
2-Aminomethyl-5-(3-trifluoromethoxy-phenyl)-4-methyl-pentanoic acid;
2-Aminomethyl-5-(4-trifluoromethoxy-phenyl)-4-methyl-pentanoic acid;
2-Aminomethyl-5-(2,3-di-trifluoromethoxy-phenyl)-4-methyl-pentanoic acid;
2-Aminomethyl-5-(2,4-di-trifluoromethoxy-phenyl)-4-methyl-pentanoic acid;
2-Aminomethyl-5-(2,5-di-trifluoromethoxy-phenyl)-4-methyl-pentanoic acid;
2-Aminomethyl-5-(2,6-di-trifluoromethoxy-phenyl)-4-methyl-pentanoic acid;
2-Aminomethyl-5-(3,4-di-trifluoromethoxy-phenyl)-4-methyl-pentanoic acid;
2-Aminomethyl-5-(3,5-di-trifluoromethoxy-phenyl)-4-methyl-pentanoic acid;
2-Aminomethyl-4-methyl-5-(2,3,4-tri-trifluoromethoxy-phenyl)-pentanoic acid;
2-Aminomethyl-4-methyl-5-(2,3,5-tri-trifluoromethoxy-phenyl)-pentanoic acid;
2-Aminomethyl-4-methyl-5-(2,3,6-tri-trifluoromethoxy-phenyl)-pentanoic acid;
2-Aminomethyl-4-methyl-5-(2,4,6-tri-trifluoromethoxy-phenyl)-pentanoic acid;
2-Aminomethyl-5-(2-trifluoromethoxy-phenyl)-4-ethyl-pentanoic acid;
2-Aminomethyl-5-(3-trifluoromethoxy-phenyl)-4-ethyl-pentanoic acid;
2-Aminomethyl-5-(4-trifluoromethoxy-phenyl)-4-ethyl-pentanoic acid;
2-Aminomethyl-5-(2,3-di-trifluoromethoxy-phenyl)-4-ethyl-pentanoic acid;
2-Aminomethyl-5-(2,4-di-trifluoromethoxy-phenyl)-4-ethyl-pentanoic acid;
2-Aminomethyl-5-(2,5-di-trifluoromethoxy-phenyl)-4-ethyl-pentanoic acid;
2-Aminomethyl-5-(2,6-di-trifluoromethoxy-phenyl)-4-ethyl-pentanoic acid;
2-Aminomethyl-5-(3,4-di-trifluoromethoxy-phenyl)-4-ethyl-pentanoic acid;
2-Aminomethyl-5-(3,5-di-trifluoromethoxy-phenyl)-4-ethyl-pentanoic acid;
2-Aminomethyl-4-ethyl-5-(2,3,4-tri-trifluoromethoxy-phenyl)-pentanoic acid;
2-Aminomethyl-4-ethyl-5-(2,3,5-tri-trifluoromethoxy-phenyl)-pentanoic acid;
2-Aminomethyl-4-ethyl-5-(2,3,6-tri-trifluoromethoxy-phenyl)-pentanoic acid;
2-Aminomethyl-4-ethyl-5-(2,4,6-tri-trifluoromethoxy-phenyl)-pentanoic acid;
2-Aminomethyl-4-ethyl-5-(2,3,4,5-tetra-trifluoromethoxy-phenyl)-pentanoic acid;
2-Aminomethyl-4-ethyl-5-(2,3,4,6-tetra-trifluoromethoxy-phenyl)-pentanoic acid;
2-Aminomethyl-4-ethyl-5-(2,3,5,6-tetra-trifluoromethoxy-phenyl)-pentanoic acid;
2-Aminomethyl-4-ethyl-5-penta-trifluoromethoxyphenyl-pentanoic acid;
2-Aminomethyl-5-(2-trifluoromethoxy-phenyl)-4-methyl-hexanoic acid;
2-Aminomethyl-5-(3-trifluoromethoxy-phenyl)-4-methyl-hexanoic acid;
2-Aminomethyl-5-(4-trifluoromethoxy-phenyl)-4-methyl-hexanoic acid;
2-Aminomethyl-5-(2,3-di-trifluoromethoxy-phenyl)-4-methyl-hexanoic acid;
2-Aminomethyl-5-(2,4-di-trifluoromethoxy-phenyl)-4-methyl-hexanoic acid;
2-Aminomethyl-5-(2,5-di-trifluoromethoxy-phenyl)-4-methyl-hexanoic acid;
2-Aminomethyl-5-(2,6-di-trifluoromethoxy-phenyl)-4-methyl-hexanoic acid;
2-Aminomethyl-5-(3,4-di-trifluoromethoxy-phenyl)-4-methyl-hexanoic acid;
2-Aminomethyl-5-(3,5-di-trifluoromethoxy-phenyl)-4-methyl-hexanoic acid;
2-Aminomethyl-4-methyl-5-(2,3,4-tri-trifluoromethoxy-phenyl)-hexanoic acid;
2-Aminomethyl-4-methyl-5-(2,3,5-tri-trifluoromethoxy-phenyl)-hexanoic acid;
2-Aminomethyl-4-methyl-5-(2,3,6-tri-trifluoromethoxy-phenyl)-hexanoic acid;
2-Aminomethyl-4-methyl-5-(2,4,6-tri-trifluoromethoxy-phenyl)-hexanoic acid;
2-Aminomethyl-6-(2-trifluoromethoxy-phenyl)-4-methyl-hexanoic acid;

2-Aminomethyl-6-(3-trifluoromethoxy-phenyl)-4-methyl-hexanoic acid;
2-Aminomethyl-6-(4-trifluoromethoxy-phenyl)-4-methyl-hexanoic acid;
2-Aminomethyl-6-(2,3-di-trifluoromethoxy-phenyl)-4-methyl-hexanoic acid;
2-Aminomethyl-6-(2,4-di-trifluoromethoxy-phenyl)-4-methyl-hexanoic acid;
2-Aminomethyl-6-(2,5-di-trifluoromethoxy-phenyl)-4-methyl-hexanoic acid;
2-Aminomethyl-6-(2,6-di-trifluoromethoxy-phenyl)-4-methyl-hexanoic acid;
2-Aminomethyl-6-(3,4-di-trifluoromethoxy-phenyl)-4-methyl-hexanoic acid;
2-Aminomethyl-6-(3,5-di-trifluoromethoxy-phenyl)-4-methyl-hexanoic acid;
2-Aminomethyl-4-methyl-6-(2,3,4-tri-trifluoromethoxy-phenyl)-hexanoic acid;
2-Aminomethyl-4-methyl-6-(2,3,5-tri-trifluoromethoxy-phenyl)-hexanoic acid;
2-Aminomethyl-4-methyl-6-(2,3,6-tri-trifluoromethoxy-phenyl)-hexanoic acid;
2-Aminomethyl-4-methyl-6-(2,4,6-tri-trifluoromethoxy-phenyl)-hexanoic acid;
2-Aminomethyl-6-(2-trifluoromethoxy-phenyl)-4-ethyl-hexanoic acid;
2-Aminomethyl-6-(3-trifluoromethoxy-phenyl)-4-ethyl-hexanoic acid;
2-Aminomethyl-6-(4-trifluoromethoxy-phenyl)-4-ethyl-hexanoic acid;
2-Aminomethyl-6-(2,3-di-trifluoromethoxy-phenyl)-4-ethyl-hexanoic acid;
2-Aminomethyl-6-(2,4-di-trifluoromethoxy-phenyl)-4-ethyl-hexanoic acid;
2-Aminomethyl-6-(2,5-di-trifluoromethoxy-phenyl)-4-ethyl-hexanoic acid;
2-Aminomethyl-6-(2,6-di-trifluoromethoxy-phenyl)-4-ethyl-hexanoic acid;
2-Aminomethyl-6-(3,4-di-trifluoromethoxy-phenyl)-4-ethyl-hexanoic acid;
2-Aminomethyl-6-(3,5-di-trifluoromethoxy-phenyl)-4-ethyl-hexanoic acid;
2-Aminomethyl-4-ethyl-6-(2,3,4-tri-trifluoromethoxy-phenyl)-hexanoic acid;
2-Aminomethyl-4-ethyl-6-(2,3,5-tri-trifluoromethoxy-phenyl)-hexanoic acid;
2-Aminomethyl-4-ethyl-6-(2,3,6-tri-trifluoromethoxy-phenyl)-hexanoic acid;
2-Aminomethyl-4-ethyl-6-(2,4,6-tri-trifluoromethoxy-phenyl)-hexanoic acid;
2-Aminomethyl-7-(2-trifluoromethoxy-phenyl)-4-methyl-heptanoic acid;
2-Aminomethyl-7-(3-trifluoromethoxy-phenyl)-4-methyl-heptanoic acid;
2-Aminomethyl-7-(4-trifluoromethoxy-phenyl)-4-methyl-heptanoic acid;
2-Aminomethyl-7-(2,3-di-trifluoromethoxy-phenyl)-4-methyl-heptanoic acid;
2-Aminomethyl-7-(2,4-di-trifluoromethoxy-phenyl)-4-methyl-heptanoic acid;
2-Aminomethyl-7-(2,5-di-trifluoromethoxy-phenyl)-4-methyl-heptanoic acid;
2-Aminomethyl-7-(2,6-di-trifluoromethoxy-phenyl)-4-methyl-heptanoic acid;
2-Aminomethyl-7-(3,4-di-trifluoromethoxy-phenyl)-4-methyl-heptanoic acid;
2-Aminomethyl-7-(3,5-di-trifluoromethoxy-phenyl)-4-methyl-heptanoic acid;
2-Aminomethyl-4-methyl-7-(2,3,4-tri-trifluoromethoxy-phenyl)-heptanoic acid;
2-Aminomethyl-4-methyl-7-(2,3,5-tri-trifluoromethoxy-phenyl)-heptanoic acid;
2-Aminomethyl-4-methyl-7-(2,3,6-tri-trifluoromethoxy-phenyl)-heptanoic acid;
2-Aminomethyl-4-methyl-7-(2,4,6-tri-trifluoromethoxy-phenyl)-heptanoic acid;
2-Aminomethyl-7-(2-trifluoromethoxy-phenyl)-4-ethyl-heptanoic acid;
2-Aminomethyl-7-(3-trifluoromethoxy-phenyl)-4-ethyl-heptanoic acid;
2-Aminomethyl-7-(4-trifluoromethoxy-phenyl)-4-ethyl-heptanoic acid;
2-Aminomethyl-7-(2,3-di-trifluoromethoxy-phenyl)-4-ethyl-heptanoic acid;
2-Aminomethyl-7-(2,4-di-trifluoromethoxy-phenyl)-4-ethyl-heptanoic acid;
2-Aminomethyl-7-(2,5-di-trifluoromethoxy-phenyl)-4-ethyl-heptanoic acid;
2-Aminomethyl-7-(2,6-di-trifluoromethoxy-phenyl)-4-ethyl-heptanoic acid;
2-Aminomethyl-7-(3,4-di-trifluoromethoxy-phenyl)-4-ethyl-heptanoic acid;
2-Aminomethyl-7-(3,5-di-trifluoromethoxy-phenyl)-4-ethyl-heptanoic acid;
2-Aminomethyl-4-ethyl-7-(2,3,4-tri-trifluoromethoxy-phenyl)-heptanoic acid;
2-Aminomethyl-4-ethyl-7-(2,3,5-tri-trifluoromethoxy-phenyl)-heptanoic acid;
2-Aminomethyl-4-ethyl-7-(2,3,6-tri-trifluoromethoxy-phenyl)-heptanoic acid;
2-Aminomethyl-4-ethyl-7-(2,4,6-tri-trifluoromethoxy-phenyl)-heptanoic acid;
2-Aminomethyl-4-(2-ethoxy-phenyl)-pentanoic acid;
2-Aminomethyl-4-(3-ethoxy-phenyl)-pentanoic acid;
2-Aminomethyl-4-(4-ethoxy-phenyl)-pentanoic acid;
2-Aminomethyl-4-(2,3-diethoxy-phenyl)-pentanoic acid;
2-Aminomethyl-4-(2,4-diethoxy-phenyl)-pentanoic acid;
2-Aminomethyl-4-(2,5-diethoxy-phenyl)-pentanoic acid;
2-Aminomethyl-4-(2,6-diethoxy-phenyl)-pentanoic acid;
2-Aminomethyl-4-(3,4-diethoxy-phenyl)-pentanoic acid;
2-Aminomethyl-4-(3,5-diethoxy-phenyl)-pentanoic acid;
2-Aminomethyl-4-(2,3,4-triethoxy-phenyl)-pentanoic acid;
2-Aminomethyl-4-(2,3,5-triethoxy-phenyl)-pentanoic acid;
2-Aminomethyl-4-(2,3,6-triethoxy-phenyl)-pentanoic acid;
2-Aminomethyl-4-(2,4,6-triethoxy-phenyl)-pentanoic acid;
2-Aminomethyl-4-(2-ethoxy-phenyl)-hexanoic acid;
2-Aminomethyl-4-(3-ethoxy-phenyl)-hexanoic acid;
2-Aminomethyl-4-(4-ethoxy-phenyl)-hexanoic acid;
2-Aminomethyl-4-(2,3-diethoxy-phenyl)-hexanoic acid;
2-Aminomethyl-4-(2,4-diethoxy-phenyl)-hexanoic acid;
2-Aminomethyl-4-(2,5-diethoxy-phenyl)-hexanoic acid;
2-Aminomethyl-4-(2,6-diethoxy-phenyl)-hexanoic acid;
2-Aminomethyl-4-(3,4-diethoxy-phenyl)-hexanoic acid;
2-Aminomethyl-4-(3,5-diethoxy-phenyl)-hexanoic acid;
2-Aminomethyl-4-(2,3,4-triethoxy-phenyl)-hexanoic acid;
2-Aminomethyl-4-(2,3,5-triethoxy-phenyl)-hexanoic acid;
2-Aminomethyl-4-(2,3,6-triethoxy-phenyl)-hexanoic acid;
2-Aminomethyl-4-(2,4,6-triethoxy-phenyl)-hexanoic acid;
2-Aminomethyl-5-(2-ethoxy-phenyl)-4-methyl-pentanoic acid;
2-Aminomethyl-5-(3-ethoxy-phenyl)-4-methyl-pentanoic acid;

2-Aminomethyl-5-(4-ethoxy-phenyl)-4-methyl-pentanoic acid;
2-Aminomethyl-5-(2,3-diethoxy-phenyl)-4-methyl-pentanoic acid;
2-Aminomethyl-5-(2,4-diethoxy-phenyl)-4-methyl-pentanoic acid;
2-Aminomethyl-5-(2,5-diethoxy-phenyl)-4-methyl-pentanoic acid;
2-Aminomethyl-5-(2,6-diethoxy-phenyl)-4-methyl-pentanoic acid;
2-Aminomethyl-5-(3,4-diethoxy-phenyl)-4-methyl-pentanoic acid;
2-Aminomethyl-5-(3,5-diethoxy-phenyl)-4-methyl-pentanoic acid;
2-Aminomethyl-4-methyl-5-(2,3,4-triethoxy-phenyl)-pentanoic acid;
2-Aminomethyl-4-methyl-5-(2,3,5-triethoxy-phenyl)-pentanoic acid;
2-Aminomethyl-4-methyl-5-(2,3,6-triethoxy-phenyl)-pentanoic acid;
2-Aminomethyl-4-methyl-5-(2,4,6-triethoxy-phenyl)-pentanoic acid;
2-Aminomethyl-5-(2-ethoxy-phenyl)-4-ethyl-pentanoic acid;
2-Aminomethyl-5-(3-ethoxy-phenyl)-4-ethyl-pentanoic acid;
2-Aminomethyl-5-(4-ethoxy-phenyl)-4-ethyl-pentanoic acid;
2-Aminomethyl-5-(2,3-diethoxy-phenyl)-4-ethyl-pentanoic acid;
2-Aminomethyl-5-(2,4-diethoxy-phenyl)-4-ethyl-pentanoic acid;
2-Aminomethyl-5-(2,5-diethoxy-phenyl)-4-ethyl-pentanoic acid;
2-Aminomethyl-5-(2,6-diethoxy-phenyl)-4-ethyl-pentanoic acid;
2-Aminomethyl-5-(3,4-diethoxy-phenyl)-4-ethyl-pentanoic acid;
2-Aminomethyl-5-(3,5-diethoxy-phenyl)-4-ethyl-pentanoic acid;
2-Aminomethyl-4-ethyl-5-(2,3,4-triethoxy-phenyl)-pentanoic acid;
2-Aminomethyl-4-ethyl-5-(2,3,5-triethoxy-phenyl)-pentanoic acid;
2-Aminomethyl-4-ethyl-5-(2,3,6-triethoxy-phenyl)-pentanoic acid;
2-Aminomethyl-4-ethyl-5-(2,4,6-triethoxy-phenyl)-pentanoic acid;
2-Aminomethyl-4-ethyl-5-(2,3,4,5-tetraethoxy-phenyl)-pentanoic acid;
2-Aminomethyl-4-ethyl-5-(2,3,4,6-tetraethoxy-phenyl)-pentanoic acid;
2-Aminomethyl-4-ethyl-5-(2,3,5,6-tetraethoxy-phenyl)-pentanoic acid;
2-Aminomethyl-4-ethyl-5-pentaethoxyphenyl-pentanoic acid;
2-Aminomethyl-5-(2-ethoxy-phenyl)-4-methyl-hexanoic acid;
2-Aminomethyl-5-(3-ethoxy-phenyl)-4-methyl-hexanoic acid;
2-Aminomethyl-5-(4-ethoxy-phenyl)-4-methyl-hexanoic acid;
2-Aminomethyl-5-(2,3-diethoxy-phenyl)-4-methyl-hexanoic acid;
2-Aminomethyl-5-(2,4-diethoxy-phenyl)-4-methyl-hexanoic acid;
2-Aminomethyl-5-(2,5-diethoxy-phenyl)-4-methyl-hexanoic acid;
2-Aminomethyl-5-(2,6-diethoxy-phenyl)-4-methyl-hexanoic acid;
2-Aminomethyl-5-(3,4-diethoxy-phenyl)-4-methyl-hexanoic acid;
2-Aminomethyl-5-(3,5-diethoxy-phenyl)-4-methyl-hexanoic acid;
2-Aminomethyl-4-methyl-5-(2,3,4-triethoxy-phenyl)-hexanoic acid;
2-Aminomethyl-4-methyl-5-(2,3,5-triethoxy-phenyl)-hexanoic acid;
2-Aminomethyl-4-methyl-5-(2,3,6-triethoxy-phenyl)-hexanoic acid;
2-Aminomethyl-4-methyl-5-(2,4,6-triethoxy-phenyl)-hexanoic acid;
2-Aminomethyl-6-(2-ethoxy-phenyl)-4-methyl-hexanoic acid;
2-Aminomethyl-6-(3-ethoxy-phenyl)-4-methyl-hexanoic acid;
2-Aminomethyl-6-(4-ethoxy-phenyl)-4-methyl-hexanoic acid;
2-Aminomethyl-6-(2,3-diethoxy-phenyl)-4-methyl-hexanoic acid;
2-Aminomethyl-6-(2,4-diethoxy-phenyl)-4-methyl-hexanoic acid;
2-Aminomethyl-6-(2,5-diethoxy-phenyl)-4-methyl-hexanoic acid;
2-Aminomethyl-6-(2,6-diethoxy-phenyl)-4-methyl-hexanoic acid;
2-Aminomethyl-6-(3,4-diethoxy-phenyl)-4-methyl-hexanoic acid;
2-Aminomethyl-6-(3,5-diethoxy-phenyl)-4-methyl-hexanoic acid;
2-Aminomethyl-4-methyl-6-(2,3,4-triethoxy-phenyl)-hexanoic acid;
2-Aminomethyl-4-methyl-6-(2,3,5-triethoxy-phenyl)-hexanoic acid;
2-Aminomethyl-4-methyl-6-(2,3,6-triethoxy-phenyl)-hexanoic acid;
2-Aminomethyl-4-methyl-6-(2,4,6-triethoxy-phenyl)-hexanoic acid;
2-Aminomethyl-6-(2-ethoxy-phenyl)-4-ethyl-hexanoic acid;
2-Aminomethyl-6-(3-ethoxy-phenyl)-4-ethyl-hexanoic acid;
2-Aminomethyl-6-(4-ethoxy-phenyl)-4-ethyl-hexanoic acid;
2-Aminomethyl-6-(2,3-diethoxy-phenyl)-4-ethyl-hexanoic acid;
2-Aminomethyl-6-(2,4-diethoxy-phenyl)-4-ethyl-hexanoic acid;
2-Aminomethyl-6-(2,5-diethoxy-phenyl)-4-ethyl-hexanoic acid;
2-Aminomethyl-6-(2,6-diethoxy-phenyl)-4-ethyl-hexanoic acid;
2-Aminomethyl-6-(3,4-diethoxy-phenyl)-4-ethyl-hexanoic acid;
2-Aminomethyl-6-(3,5-diethoxy-phenyl)-4-ethyl-hexanoic acid;
2-Aminomethyl-4-ethyl-6-(2,3,4-triethoxy-phenyl)-hexanoic acid;
2-Aminomethyl-4-ethyl-6-(2,3,5-triethoxy-phenyl)-hexanoic acid;
2-Aminomethyl-4-ethyl-6-(2,3,6-triethoxy-phenyl)-hexanoic acid;

2-Aminomethyl-4-ethyl-6-(2,4,6-triethoxy-phenyl)-hexanoic acid;
2-Aminomethyl-7-(2-ethoxy-phenyl)-4-methyl-heptanoic acid;
2-Aminomethyl-7-(3-ethoxy-phenyl)-4-methyl-heptanoic acid;
2-Aminomethyl-7-(4-ethoxy-phenyl)-4-methyl-heptanoic acid;
2-Aminomethyl-7-(2,3-diethoxy-phenyl)-4-methyl-heptanoic acid;
2-Aminomethyl-7-(2,4-diethoxy-phenyl)-4-methyl-heptanoic acid;
2-Aminomethyl-7-(2,5-diethoxy-phenyl)-4-methyl-heptanoic acid;
2-Aminomethyl-7-(2,6-diethoxy-phenyl)-4-methyl-heptanoic acid;
2-Aminomethyl-7-(3,4-diethoxy-phenyl)-4-methyl-heptanoic acid;
2-Aminomethyl-7-(3,5-diethoxy-phenyl)-4-methyl-heptanoic acid;
2-Aminomethyl-4-methyl-7-(2,3,4-triethoxy-phenyl)-heptanoic acid;
2-Aminomethyl-4-methyl-7-(2,3,5-triethoxy-phenyl)-heptanoic acid;
2-Aminomethyl-4-methyl-7-(2,3,6-triethoxy-phenyl)-heptanoic acid;
2-Aminomethyl-4-methyl-7-(2,4,6-triethoxy-phenyl)-heptanoic acid;
2-Aminomethyl-7-(2-ethoxy-phenyl)-4-ethyl-heptanoic acid;
2-Aminomethyl-7-(3-ethoxy-phenyl)-4-ethyl-heptanoic acid;
2-Aminomethyl-7-(4-ethoxy-phenyl)-4-ethyl-heptanoic acid;
2-Aminomethyl-7-(2,3-diethoxy-phenyl)-4-ethyl-heptanoic acid;
2-Aminomethyl-7-(2,4-diethoxy-phenyl)-4-ethyl-heptanoic acid;
2-Aminomethyl-7-(2,5-diethoxy-phenyl)-4-ethyl-heptanoic acid;
2-Aminomethyl-7-(2,6-diethoxy-phenyl)-4-ethyl-heptanoic acid;
2-Aminomethyl-7-(3,4-diethoxy-phenyl)-4-ethyl-heptanoic acid;
2-Aminomethyl-7-(3,5-diethoxy-phenyl)-4-ethyl-heptanoic acid;
2-Aminomethyl-4-ethyl-7-(2,3,4-triethoxy-phenyl)-heptanoic acid;
2-Aminomethyl-4-ethyl-7-(2,3,5-triethoxy-phenyl)-heptanoic acid;
2-Aminomethyl-4-ethyl-7-(2,3,6-triethoxy-phenyl)-heptanoic acid;
2-Aminomethyl-4-ethyl-7-(2,4,6-triethoxy-phenyl)-heptanoic acid;
2-Aminomethyl-4-(2-methyl-phenyl)-pentanoic acid;
2-Aminomethyl-4-(3-methyl-phenyl)-pentanoic acid;
2-Aminomethyl-4-(4-methyl-phenyl)-pentanoic acid;
2-Aminomethyl-4-(2,3-dimethyl-phenyl)-pentanoic acid;
2-Aminomethyl-4-(2,4-dimethyl-phenyl)-pentanoic acid;
2-Aminomethyl-4-(2,5-dimethyl-phenyl)-pentanoic acid;
2-Aminomethyl-4-(2,6-dimethyl-phenyl)-pentanoic acid;
2-Aminomethyl-4-(3,4-dimethyl-phenyl)-pentanoic acid;
2-Aminomethyl-4-(3,5-dimethyl-phenyl)-pentanoic acid;
2-Aminomethyl-4-(2,3,4-trimethyl-phenyl)-pentanoic acid;
2-Aminomethyl-4-(2,3,5-trimethyl-phenyl)-pentanoic acid;
2-Aminomethyl-4-(2,3,6-trimethyl-phenyl)-pentanoic acid;
2-Aminomethyl-4-(2,4,6-trimethyl-phenyl)-pentanoic acid;
2-Aminomethyl-4-(2-methyl-phenyl)-hexanoic acid;
2-Aminomethyl-4-(3-methyl-phenyl)-hexanoic acid;
2-Aminomethyl-4-(4-methyl-phenyl)-hexanoic acid;
2-Aminomethyl-4-(2,3-dimethyl-phenyl)-hexanoic acid;
2-Aminomethyl-4-(2,4-dimethyl-phenyl)-hexanoic acid;
2-Aminomethyl-4-(2,5-dimethyl-phenyl)-hexanoic acid;
2-Aminomethyl-4-(2,6-dimethyl-phenyl)-hexanoic acid;
2-Aminomethyl-4-(3,4-dimethyl-phenyl)-hexanoic acid;
2-Aminomethyl-4-(3,5-dimethyl-phenyl)-hexanoic acid;
2-Aminomethyl-4-(2,3,4-trimethyl-phenyl)-hexanoic acid;
2-Aminomethyl-4-(2,3,5-trimethyl-phenyl)-hexanoic acid;
2-Aminomethyl-4-(2,3,6-trimethyl-phenyl)-hexanoic acid;
2-Aminomethyl-4-(2,4,6-trimethyl-phenyl)-hexanoic acid;
2-Aminomethyl-5-(2-methyl-phenyl)-4-methyl-pentanoic acid;
2-Aminomethyl-5-(3-methyl-phenyl)-4-methyl-pentanoic acid;
2-Aminomethyl-5-(4-methyl-phenyl)-4-methyl-pentanoic acid;
2-Aminomethyl-5-(2,3-dimethyl-phenyl)-4-methyl-pentanoic acid;
2-Aminomethyl-5-(2,4-dimethyl-phenyl)-4-methyl-pentanoic acid;
2-Aminomethyl-5-(2,5-dimethyl-phenyl)-4-methyl-pentanoic acid;
2-Aminomethyl-5-(2,6-dimethyl-phenyl)-4-methyl-pentanoic acid;
2-Aminomethyl-5-(3,4-dimethyl-phenyl)-4-methyl-pentanoic acid;
2-Aminomethyl-5-(3,5-dimethyl-phenyl)-4-methyl-pentanoic acid;
2-Aminomethyl-4-methyl-5-(2,3,4-trimethyl-phenyl)-pentanoic acid;
2-Aminomethyl-4-methyl-5-(2,3,5-trimethyl-phenyl)-pentanoic acid;
2-Aminomethyl-4-methyl-5-(2,3,6-trimethyl-phenyl)-pentanoic acid;
2-Aminomethyl-4-methyl-5-(2,4,6-trimethyl-phenyl)-pentanoic acid;
2-Aminomethyl-5-(2-methyl-phenyl)-4-ethyl-pentanoic acid;
2-Aminomethyl-5-(3-methyl-phenyl)-4-ethyl-pentanoic acid;
2-Aminomethyl-5-(4-methyl-phenyl)-4-ethyl-pentanoic acid;
2-Aminomethyl-5-(2,3-dimethyl-phenyl)-4-ethyl-pentanoic acid;
2-Aminomethyl-5-(2,4-dimethyl-phenyl)-4-ethyl-pentanoic acid;
2-Aminomethyl-5-(2,5-dimethyl-phenyl)-4-ethyl-pentanoic acid;
2-Aminomethyl-5-(2,6-dimethyl-phenyl)-4-ethyl-pentanoic acid;
2-Aminomethyl-5-(3,4-dimethyl-phenyl)-4-ethyl-pentanoic acid;
2-Aminomethyl-5-(3,5-dimethyl-phenyl)-4-ethyl-pentanoic acid;
2-Aminomethyl-4-ethyl-5-(2,3,4-trimethyl-phenyl)-pentanoic acid;
2-Aminomethyl-4-ethyl-5-(2,3,5-trimethyl-phenyl)-pentanoic acid;
2-Aminomethyl-4-ethyl-5-(2,3,6-trimethyl-phenyl)-pentanoic acid;
2-Aminomethyl-4-ethyl-5-(2,4,6-trimethyl-phenyl)-pentanoic acid;
2-Aminomethyl-4-ethyl-5-(2,3,4,5-tetramethyl-phenyl)-pentanoic acid;

2-Aminomethyl-4-ethyl-5-(2,3,4,6-tetramethyl-phenyl)-pentanoic acid;
2-Aminomethyl-4-ethyl-5-(2,3,5,6-tetramethyl-phenyl)-pentanoic acid;
2-Aminomethyl-4-ethyl-5-pentamethylphenyl-pentanoic acid;
2-Aminomethyl-5-(2-methyl-phenyl)-4-methyl-hexanoic acid;
2-Aminomethyl-5-(3-methyl-phenyl)-4-methyl-hexanoic acid;
2-Aminomethyl-5-(4-methyl-phenyl)-4-methyl-hexanoic acid;
2-Aminomethyl-5-(2,3-dimethyl-phenyl)-4-methyl-hexanoic acid;
2-Aminomethyl-5-(2,4-dimethyl-phenyl)-4-methyl-hexanoic acid;
2-Aminomethyl-5-(2,5-dimethyl-phenyl)-4-methyl-hexanoic acid;
2-Aminomethyl-5-(2,6-dimethyl-phenyl)-4-methyl-hexanoic acid;
2-Aminomethyl-5-(3,4-dimethyl-phenyl)-4-methyl-hexanoic acid;
2-Aminomethyl-5-(3,5-dimethyl-phenyl)-4-methyl-hexanoic acid;
2-Aminomethyl-4-methyl-5-(2,3,4-trimethyl-phenyl)-hexanoic acid;
2-Aminomethyl-4-methyl-5-(2,3,5-trimethyl-phenyl)-hexanoic acid;
2-Aminomethyl-4-methyl-5-(2,3,6-trimethyl-phenyl)-hexanoic acid;
2-Aminomethyl-4-methyl-5-(2,4,6-trimethyl-phenyl)-hexanoic acid;
2-Aminomethyl-6-(2-methyl-phenyl)-4-methyl-hexanoic acid;
2-Aminomethyl-6-(3-methyl-phenyl)-4-methyl-hexanoic acid;
2-Aminomethyl-6-(4-methyl-phenyl)-4-methyl-hexanoic acid;
2-Aminomethyl-6-(2,3-dimethyl-phenyl)-4-methyl-hexanoic acid;
2-Aminomethyl-6-(2,4-dimethyl-phenyl)-4-methyl-hexanoic acid;
2-Aminomethyl-6-(2,5-dimethyl-phenyl)-4-methyl-hexanoic acid;
2-Aminomethyl-6-(2,6-dimethyl-phenyl)-4-methyl-hexanoic acid;
2-Aminomethyl-6-(3,4-dimethyl-phenyl)-4-methyl-hexanoic acid;
2-Aminomethyl-6-(3,5-dimethyl-phenyl)-4-methyl-hexanoic acid;
2-Aminomethyl-4-methyl-6-(2,3,4-trimethyl-phenyl)-hexanoic acid;
2-Aminomethyl-4-methyl-6-(2,3,5-trimethyl-phenyl)-hexanoic acid;
2-Aminomethyl-4-methyl-6-(2,3,6-trimethyl-phenyl)-hexanoic acid;
2-Aminomethyl-4-methyl-6-(2,4,6-trimethyl-phenyl)-hexanoic acid;
2-Aminomethyl-6-(2-methyl-phenyl)-4-ethyl-hexanoic acid;
2-Aminomethyl-6-(3-methyl-phenyl)-4-ethyl-hexanoic acid;
2-Aminomethyl-6-(4-methyl-phenyl)-4-ethyl-hexanoic acid;
2-Aminomethyl-6-(2,3-dimethyl-phenyl)-4-ethyl-hexanoic acid;
2-Aminomethyl-6-(2,4-dimethyl-phenyl)-4-ethyl-hexanoic acid;
2-Aminomethyl-6-(2,5-dimethyl-phenyl)-4-ethyl-hexanoic acid;
2-Aminomethyl-6-(2,6-dimethyl-phenyl)-4-ethyl-hexanoic acid;
2-Aminomethyl-6-(3,4-dimethyl-phenyl)-4-ethyl-hexanoic acid,
2-Aminomethyl-6-(3,5-dimethyl-phenyl)-4-ethyl-hexanoic acid;
2-Aminomethyl-4-ethyl-6-(2,3,4-trimethyl-phenyl)-hexanoic acid;
2-Aminomethyl-4-ethyl-6-(2,3,5-trimethyl-phenyl)-hexanoic acid;
2-Aminomethyl-4-ethyl-6-(2,3,6-trimethyl-phenyl)-hexanoic acid;
2-Aminomethyl-4-ethyl-6-(2,4,6-trimethyl-phenyl)-hexanoic acid;
2-Aminomethyl-7-(2-methyl-phenyl)-4-methyl-heptanoic acid;
2-Aminomethyl-7-(3-methyl-phenyl)-4-methyl-heptanoic acid;
2-Aminomethyl-7-(4-methyl-phenyl)-4-methyl-heptanoic acid;
2-Aminomethyl-7-(2,3-dimethyl-phenyl)-4-methyl-heptanoic acid;
2-Aminomethyl-7-(2,4-dimethyl-phenyl)-4-methyl-heptanoic acid;
2-Aminomethyl-7-(2,5-dimethyl-phenyl)-4-methyl-heptanoic acid;
2-Aminomethyl-7-(2,6-dimethyl-phenyl)-4-methyl-heptanoic acid;
2-Aminomethyl-7-(3,4-dimethyl-phenyl)-4-methyl-heptanoic acid;
2-Aminomethyl-7-(3,5-dimethyl-phenyl)-4-methyl-heptanoic acid;
2-Aminomethyl-4-methyl-7-(2,3,4-trimethyl-phenyl)-heptanoic acid;
2-Aminomethyl-4-methyl-7-(2,3,5-trimethyl-phenyl)-heptanoic acid;
2-Aminomethyl-4-methyl-7-(2,3,6-trimethyl-phenyl)-heptanoic acid;
2-Aminomethyl-4-methyl-7-(2,4,6-trimethyl-phenyl)-heptanoic acid;
2-Aminomethyl-7-(2-methyl-phenyl)-4-ethyl-heptanoic acid;
2-Aminomethyl-7-(3-methyl-phenyl)-4-ethyl-heptanoic acid;
2-Aminomethyl-7-(4-methyl-phenyl)-4-ethyl-heptanoic acid;
2-Aminomethyl-7-(2,3-dimethyl-phenyl)-4-ethyl-heptanoic acid;
2-Aminomethyl-7-(2,4-dimethyl-phenyl)-4-ethyl-heptanoic acid;
2-Aminomethyl-7-(2,5-dimethyl-phenyl)-4-ethyl-heptanoic acid;
2-Aminomethyl-7-(2,6-dimethyl-phenyl)-4-ethyl-heptanoic acid;
2-Aminomethyl-7-(3,4-dimethyl-phenyl)-4-ethyl-heptanoic acid;
2-Aminomethyl-7-(3,5-dimethyl-phenyl)-4-ethyl-heptanoic acid;
2-Aminomethyl-4-ethyl-7-(2,3,4-trimethyl-phenyl)-heptanoic acid;
2-Aminomethyl-4-ethyl-7-(2,3,5-trimethyl-phenyl)-heptanoic acid;

2-Aminomethyl-4-ethyl-7-(2,3,6-trimethyl-phenyl)-heptanoic acid;
2-Aminomethyl-4-ethyl-7-(2,4,6-trimethyl-phenyl)-heptanoic acid;
2-Aminomethyl-4-(2-hydroxy-phenyl)-pentanoic acid;
2-Aminomethyl-4-(3-hydroxy-phenyl)-pentanoic acid;
2-Aminomethyl-4-(4-hydroxy-phenyl)-pentanoic acid;
2-Aminomethyl-4-(2,3-dihydroxy-phenyl)-pentanoic acid;
2-Aminomethyl-4-(2,4-dihydroxy-phenyl)-pentanoic acid;
2-Aminomethyl-4-(2,5-dihydroxy-phenyl)-pentanoic acid;
2-Aminomethyl-4-(2,6-dihydroxy-phenyl)-pentanoic acid;
2-Aminomethyl-4-(3,4-dihydroxy-phenyl)-pentanoic acid;
2-Aminomethyl-4-(3,5-dihydroxy-phenyl)-pentanoic acid;
2-Aminomethyl-4-(2,3,4-trihydroxy-phenyl)-pentanoic acid;
2-Aminomethyl-4-(2,3,5-trihydroxy-phenyl)-pentanoic acid;
2-Aminomethyl-4-(2,3,6-trihydroxy-phenyl)-pentanoic acid;
2-Aminomethyl-4-(2,4,6-trihydroxy-phenyl)-pentanoic acid;
2-Aminomethyl-4-(2-hydroxy-phenyl)-hexanoic acid;
2-Aminomethyl-4-(3-hydroxy-phenyl)-hexanoic acid;
2-Aminomethyl-4-(4-hydroxy-phenyl)-hexanoic acid;
2-Aminomethyl-4-(2,3-dihydroxy-phenyl)-hexanoic acid;
2-Aminomethyl-4-(2,4-dihydroxy-phenyl)-hexanoic acid;
2-Aminomethyl-4-(2,5-dihydroxy-phenyl)-hexanoic acid;
2-Aminomethyl-4-(2,6-dihydroxy-phenyl)-hexanoic acid;
2-Aminomethyl-4-(3,4-dihydroxy-phenyl)-hexanoic acid;
2-Aminomethyl-4-(3,5-dihydroxy-phenyl)-hexanoic acid;
2-Aminomethyl-4-(2,3,4-trihydroxy-phenyl)-hexanoic acid;
2-Aminomethyl-4-(2,3,5-trihydroxy-phenyl)-hexanoic acid;
2-Aminomethyl-4-(2,3,6-trihydroxy-phenyl)-hexanoic acid;
2-Aminomethyl-4-(2,4,6-trihydroxy-phenyl)-hexanoic acid;
2-Aminomethyl-5-(2-hydroxy-phenyl)-4-methyl-pentanoic acid;
2-Aminomethyl-5-(3-hydroxy-phenyl)-4-methyl-pentanoic acid;
2-Aminomethyl-5-(4-hydroxy-phenyl)-4-methyl-pentanoic acid;
2-Aminomethyl-5-(2,3-dihydroxy-phenyl)-4-methyl-pentanoic acid;
2-Aminomethyl-5-(2,4-dihydroxy-phenyl)-4-methyl-pentanoic acid;
2-Aminomethyl-5-(2,5-dihydroxy-phenyl)-4-methyl-pentanoic acid;
2-Aminomethyl-5-(2,6-dihydroxy-phenyl)-4-methyl-pentanoic acid;
2-Aminomethyl-5-(3,4-dihydroxy-phenyl)-4-methyl-pentanoic acid;
2-Aminomethyl-5-(3,5-dihydroxy-phenyl)-4-methyl-pentanoic acid;
2-Aminomethyl-4-methyl-5-(2,3,4-trihydroxy-phenyl)-pentanoic acid;
2-Aminomethyl-4-methyl-5-(2,3,5-trihydroxy-phenyl)-pentanoic acid;
2-Aminomethyl-4-methyl-5-(2,3,6-trihydroxy-phenyl)-pentanoic acid;
2-Aminomethyl-4-methyl-5-(2,4,6-trihydroxy-phenyl)-pentanoic acid;
2-Aminomethyl-5-(2-hydroxy-phenyl)-4-methyl-hexanoic acid;
2-Aminomethyl-5-(3-hydroxy-phenyl)-4-methyl-hexanoic acid;
2-Aminomethyl-5-(4-hydroxy-phenyl)-4-methyl-hexanoic acid;
2-Aminomethyl-5-(2,3-dihydroxy-phenyl)-4-methyl-hexanoic acid;
2-Aminomethyl-5-(2,4-dihydroxy-phenyl)-4-methyl-hexanoic acid;
2-Aminomethyl-5-(2,5-dihydroxy-phenyl)-4-methyl-hexanoic acid;
2-Aminomethyl-5-(2,6-dihydroxy-phenyl)-4-methyl-hexanoic acid;
2-Aminomethyl-5-(3,4-dihydroxy-phenyl)-4-methyl-hexanoic acid;
2-Aminomethyl-5-(3,5-dihydroxy-phenyl)-4-methyl-hexanoic acid;
2-Aminomethyl-4-methyl-5-(2,3,4-trihydroxy-phenyl)-hexanoic acid;
2-Aminomethyl-4-methyl-5-(2,3,5-trihydroxy-phenyl)-hexanoic acid;
2-Aminomethyl-4-methyl-5-(2,3,6-trihydroxy-phenyl)-hexanoic acid;
2-Aminomethyl-4-methyl-5-(2,4,6-trihydroxy-phenyl)-hexanoic acid;
2-Aminomethyl-6-(2-hydroxy-phenyl)-4-methyl-hexanoic acid;
2-Aminomethyl-6-(3-hydroxy-phenyl)-4-methyl-hexanoic acid;
2-Aminomethyl-6-(4-hydroxy-phenyl)-4-methyl-hexanoic acid;
2-Aminomethyl-6-(2,3-dihydroxy-phenyl)-4-methyl-hexanoic acid;
2-Aminomethyl-6-(2,4-dihydroxy-phenyl)-4-methyl-hexanoic acid;
2-Aminomethyl-6-(2,5-dihydroxy-phenyl)-4-methyl-hexanoic acid;
2-Aminomethyl-6-(2,6-dihydroxy-phenyl)-4-methyl-hexanoic acid;
2-Aminomethyl-6-(3,4-dihydroxy-phenyl)-4-methyl-hexanoic acid;
2-Aminomethyl-6-(3,5-dihydroxy-phenyl)-4-methyl-hexanoic acid;
2-Aminomethyl-4-methyl-6-(2,3,4-trihydroxy-phenyl)-hexanoic acid;
2-Aminomethyl-4-methyl-6-(2,3,5-trihydroxy-phenyl)-hexanoic acid;
2-Aminomethyl-4-methyl-6-(2,3,6-trihydroxy-phenyl)-hexanoic acid;
2-Aminomethyl-4-methyl-6-(2,4,6-trihydroxy-phenyl)-hexanoic acid;
2-Aminomethyl-5-(2-hydroxy-phenyl)-4-ethyl-pentanoic acid;
2-Aminomethyl-5-(3-hydroxy-phenyl)-4-ethyl-pentanoic acid;
2-Aminomethyl-5-(4-hydroxy-phenyl)-4-ethyl-pentanoic acid;
2-Aminomethyl-5-(2,3-dihydroxy-phenyl)-4-ethyl-pentanoic acid;
2-Aminomethyl-5-(2,4-dihydroxy-phenyl)-4-ethyl-pentanoic acid;
2-Aminomethyl-5-(2,5-dihydroxy-phenyl)-4-ethyl-pentanoic acid;
2-Aminomethyl-5-(2,6-dihydroxy-phenyl)-4-ethyl-pentanoic acid;
2-Aminomethyl-5-(3,4-dihydroxy-phenyl)-4-ethyl-pentanoic acid;
2-Aminomethyl-5-(3,5-dihydroxy-phenyl)-4-ethyl-pentanoic acid;
2-Aminomethyl-4-ethyl-5-(2,3,4-trihydroxy-phenyl)-pentanoic acid;

2-Aminomethyl-4-ethyl-5-(2,3,5-trihydroxy-phenyl)-pentanoic acid;
2-Aminomethyl-4-ethyl-5-(2,3,6-trihydroxy-phenyl)-pentanoic acid;
2-Aminomethyl-4-ethyl-5-(2,4,6-trihydroxy-phenyl)-pentanoic acid;
2-Aminomethyl-4-ethyl-5-(2,3,4,5-tetrahydroxy-phenyl)-pentanoic acid;
2-Aminomethyl-4-ethyl-5-(2,3,4,6-tetrahydroxy-phenyl)-pentanoic acid;
2-Aminomethyl-4-ethyl-5-(2,3,5,6-tetrahydroxy-phenyl)-pentanoic acid;
2-Aminomethyl-4-ethyl-5-pentahydroxyphenyl-pentanoic acid;
2-Aminomethyl-6-(2-hydroxy-phenyl)-4-ethyl-hexanoic acid;
2-Aminomethyl-6-(3-hydroxy-phenyl)-4-ethyl-hexanoic acid;
2-Aminomethyl-6-(4-hydroxy-phenyl)-4-ethyl-hexanoic acid;
2-Aminomethyl-6-(2,3-dihydroxy-phenyl)-4-ethyl-hexanoic acid;
2-Aminomethyl-6-(2,4-dihydroxy-phenyl)-4-ethyl-hexanoic acid;
2-Aminomethyl-6-(2,5-dihydroxy-phenyl)-4-ethyl-hexanoic acid;
2-Aminomethyl-6-(2,6-dihydroxy-phenyl)-4-ethyl-hexanoic acid;
2-Aminomethyl-6-(3,4-dihydroxy-phenyl)-4-ethyl-hexanoic acid;
2-Aminomethyl-6-(3,5-dihydroxy-phenyl)-4-ethyl-hexanoic acid;
2-Aminomethyl-4-ethyl-6-(2,3,4-trihydroxy-phenyl)-hexanoic acid;
2-Aminomethyl-4-ethyl-6-(2,3,5-trihydroxy-phenyl)-hexanoic acid;
2-Aminomethyl-4-ethyl-6-(2,3,6-trihydroxy-phenyl)-hexanoic acid;
2-Aminomethyl-4-ethyl-6-(2,4,6-trihydroxy-phenyl)-hexanoic acid;
2-Aminomethyl-7-(2-hydroxy-phenyl)-4-methyl-heptanoic acid;
2-Aminomethyl-7-(3-hydroxy-phenyl)-4-methyl-heptanoic acid;
2-Aminomethyl-7-(4-hydroxy-phenyl)-4-methyl-heptanoic acid;
2-Aminomethyl-7-(2,3-dihydroxy-phenyl)-4-methyl-heptanoic acid;
2-Aminomethyl-7-(2,4-dihydroxy-phenyl)-4-methyl-heptanoic acid;
2-Aminomethyl-7-(2,5-dihydroxy-phenyl)-4-methyl-heptanoic acid;
2-Aminomethyl-7-(2,6-dihydroxy-phenyl)-4-methyl-heptanoic acid;
2-Aminomethyl-7-(3,4-dihydroxy-phenyl)-4-methyl-heptanoic acid;
2-Aminomethyl-7-(3,5-dihydroxy-phenyl)-4-methyl-heptanoic acid;
2-Aminomethyl-4-methyl-7-(2,3,4-trihydroxy-phenyl)-heptanoic acid;
2-Aminomethyl-4-methyl-7-(2,3,5-trihydroxy-phenyl)-heptanoic acid;
2-Aminomethyl-4-methyl-7-(2,3,6-trihydroxy-phenyl)-heptanoic acid;
2-Aminomethyl-4-methyl-7-(2,4,6-trihydroxy-phenyl)-heptanoic acid;
2-Aminomethyl-7-(2-hydroxy-phenyl)-4-ethyl-heptanoic acid;
2-Aminomethyl-7-(3-hydroxy-phenyl)-4-ethyl-heptanoic acid;
2-Aminomethyl-7-(4-hydroxy-phenyl)-4-ethyl-heptanoic acid;
2-Aminomethyl-7-(2,3-dihydroxy-phenyl)-4-ethyl-heptanoic acid;
2-Aminomethyl-7-(2,4-dihydroxy-phenyl)-4-ethyl-heptanoic acid;
2-Aminomethyl-7-(2,5-dihydroxy-phenyl)-4-ethyl-heptanoic acid;
2-Aminomethyl-7-(2,6-dihydroxy-phenyl)-4-ethyl-heptanoic acid;
2-Aminomethyl-7-(3,4-dihydroxy-phenyl)-4-ethyl-heptanoic acid;
2-Aminomethyl-7-(3,5-dihydroxy-phenyl)-4-ethyl-heptanoic acid;
2-Aminomethyl-4-ethyl-7-(2,3,4-trihydroxy-phenyl)-heptanoic acid;
2-Aminomethyl-4-ethyl-7-(2,3,5-trihydroxy-phenyl)-heptanoic acid;
2-Aminomethyl-4-ethyl-7-(2,3,6-trihydroxy-phenyl)-heptanoic acid;
2-Aminomethyl-4-ethyl-7-(2,4,6-trihydroxy-phenyl)-heptanoic acid;
2-Aminomethyl-4-ethyl-7-(2,3,4,5-tetrahydroxy-phenyl)-heptanoic acid;
2-Aminomethyl-4-ethyl-7-(2,3,4,6-tetrahydroxy-phenyl)-heptanoic acid;
2-Aminomethyl-4-ethyl-7-(2,3,5,6-tetrahydroxy-phenyl)-heptanoic acid;
2-Aminomethyl-4-ethyl-7-pentahydroxyphenyl-heptanoic acid;
(2R,4R)-2-Aminomethyl-4-(2,4-difluoro-benzyl)-hexanoic acid;
(2S,4R)-2-Aminomethyl-4-(2,4-difluoro-benzyl)-hexanoic acid;
(2R,4S)-2-Aminomethyl-7-(2,4-difluoro-phenyl)-4-ethyl-heptanoic acid;
(2S,4S)-2-Aminomethyl-7-(2,4-difluoro-phenyl)-4-ethyl-heptanoic acid;
(2R,4S)-2-Aminomethyl-4-(2,4-difluoro-benzyl)-hexanoic acid;
(2S,4S)-2-Aminomethyl-4-(2,4-difluoro-benzyl)-hexanoic acid;
(2S,4S)-2-Aminomethyl-4-(3,5-difluoro-benzyl)-hexanoic acid;
(2S,4S)-2-Aminomethyl-4-(2-fluoro-benzyl)-hexanoic acid;
(2S,4S)-2-Aminomethyl-5-(2,4-difluoro-phenyl)-4-methyl-pentanoic acid;
(2S)-2-Aminomethyl-5-(2,4-difluoro-phenyl)-pentanoic acid;
(2S,4S)-2-Aminomethyl-4-(2,6-difluoro-benzyl)-hexanoic acid;
(2S,4S)-2-Aminomethyl-4-(4-fluoro-benzyl)-hexanoic acid;
(2S,4S)-2-Aminomethyl-4-(2,5-difluoro-benzyl)-hexanoic acid;
(2S,4S)-2-Aminomethyl-4-(3-fluoro-benzyl)-hexanoic acid;
(2S,4S)-2-Aminomethyl-4-pentafluorophenylmethyl-hexanoic acid;
(2S,4R)-2-Aminomethyl-7-(2,4-difluoro-phenyl)-4-ethyl-heptanoic acid;
(2S,4S)-2-Aminomethyl-4-(4-trifluoromethyl-benzyl)-hexanoic acid;
2-Aminomethyl-4-(4-methoxy-2-methyl-benzyl)-hexanoic acid;

2-Aminomethyl-5-(4-methoxy-2-methyl-phenyl)-4-methyl-pentanoic acid;
2-Aminomethyl-4-(4-methoxy-3-methyl-benzyl)-hexanoic acid; and
2-Aminomethyl-5-(4-methoxy-3-methyl-phenyl)-4-methyl-pentanoic acid.

Other compounds of formula V include the following compounds, and their pharmaceutically acceptable salts:
2-Aminomethyl-4-ethyl-5-methyl-hexanoic acid;
2-Aminomethyl-4-ethyl-3-methyl-hexanoic acid;
2-Aminomethyl-3,4-dimethyl-hexanoic acid;
2-Aminomethyl-3-ethyl-4-methyl-hexanoic acid;
2-Aminomethyl-4-ethyl-3-methyl-heptanoic acid;
2-Aminomethyl-3,4-dimethyl-octanoic acid;
2-Aminomethyl-3-methyl-pentanoic acid;
2-Aminomethyl-3-methyl-hexanoic acid;
2-Aminomethyl-3-methyl-heptanoic acid;
2-Aminomethyl-3,4-dimethyl-pentanoic acid;
2-Aminomethyl-3,5-dimethyl-hexanoic acid;
2-Aminomethyl-3,6-dimethyl-heptanoic acid;
2-Aminomethyl-3,5,5-trimethyl-hexanoic acid;
2-Aminomethyl-3-cyclopropyl-butyric acid;
2-Aminomethyl-3-cyclopentyl-butyric acid;
2-Aminomethyl-3-cyclohexyl-butyric acid;
2-Aminomethyl-4-cyclohexyl-3-methyl-butyric acid;
2-Aminomethyl-5-cyclohexyl-3-methyl-pentanoic acid;
2-Aminomethyl-3-methyl-4-(4-methyl-cyclohexyl)-butyric acid;
2-Aminomethyl-3-ethyl-pentanoic acid;
2-Aminomethyl-3-ethyl-hexanoic acid;
2-Aminomethyl-3-ethyl-heptanoic acid;
2-Aminomethyl-3-ethyl-4-methyl-pentanoic acid;
2-Aminomethyl-3-cyclohexylmethyl-pentanoic acid;
2-Aminomethyl-5-(4-methoxy-cyclohexyl)-3-methyl-pentanoic acid;
2-Aminomethyl-5-(4-methoxy-phenyl)-3-methyl-pentanoic acid;
2-Aminomethyl-4-(2-methoxy-phenyl)-3-methyl-butyric acid;
2-Aminomethyl-4-(4-methoxy-phenyl)-3-methyl-butyric acid;
2-Aminomethyl-3-phenyl-butyric acid;
2-Aminomethyl-3-methyl-4-phenyl-butyric acid;
2-Aminomethyl-3-methyl-5-phenyl-pentanoic acid;
2-Aminomethyl-3-methyl-4-(3-trifluoromethyl-phenyl)-butyric acid;
2-Aminomethyl-3-(4-ethyl-phenyl)-butyric acid;
2-Aminomethyl-3-(2,5-dimethyl-phenyl)-butyric acid;
2-Aminomethyl-3-methyl-4-p-tolyl-butyric acid;
2-Aminomethyl-3-m-tolyl-butyric acid;
2-Aminomethyl-3-benzyl-pentanoic acid; and
2-Aminomethyl-4-(4-fluoro-phenyl)-3-methyl-butyric acid.

This invention also provides compounds of formula VI

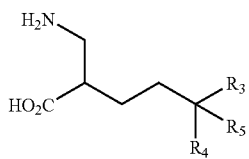

VI and their pharmaceutically acceptable salts, wherein $R_3$, $R_4$, and $R_5$ are as defined above in formula I, with the proviso that $R_3$, $R_4$, and $R_5$ are not simultaneously hydrogen atoms.

Specific compounds of formula VI include the following compounds and their pharmaceutically acceptable salts:
2-Aminomethyl-5-cyclopropyl-hexanoic acid;
2-Aminomethyl-5-cyclobutyl-hexanoic acid;
2-Aminomethyl-5-cyclopentyl-hexanoic acid;
2-Aminomethyl-5-cyclohexyl-hexanoic acid;
2-Aminomethyl-5-phenyl-hexanoic acid;
2-Aminomethyl-5-(3-chloro-phenyl)-hexanoic acid;
2-Aminomethyl-5-(3-trifluoromethyl-phenyl)-hexanoic acid;
2-Aminomethyl-5-(4-trifluoromethyl-phenyl)-hexanoic acid;
2-Aminomethyl-5-cyclopropyl-heptanoic acid;
2-Aminomethyl-5-cyclobutyl-heptanoic acid;
2-Aminomethyl-5-cyclopentyl-heptanoic acid;
2-Aminomethyl-5-cyclohexyl-heptanoic acid;
2-Aminomethyl-5-phenyl-heptanoic acid;
2-Aminomethyl-5-(3-chloro-phenyl)-heptanoic acid;
2-Aminomethyl-5-(3-trifluoromethyl-phenyl)-heptanoic acid;
2-Aminomethyl-5-(4-trifluoromethyl-phenyl)-heptanoic acid;
2-Aminomethyl-5-methyl-6-phenyl-hexanoic acid;
2-Aminomethyl-6-(3-chloro-phenyl)-5-methyl-hexanoic acid;
2-Aminomethyl-5-methyl-6-(3-trifluoromethyl-phenyl)-hexanoic acid;
2-Aminomethyl-5-methyl-6-(4-trifluoromethyl-phenyl)-hexanoic acid;
2-Aminomethyl-5-cyclopropylmethyl-heptanoic acid;
2-Aminomethyl-5-cyclobutylmethyl-heptanoic acid;
2-Aminomethyl-5-cyclopentylmethyl-heptanoic acid;
2-Aminomethyl-5-cyclohexylmethyl-heptanoic acid;
2-Aminomethyl-5-benzyl-heptanoic acid;
2-Aminomethyl-5-(3-chloro-benzyl)-heptanoic acid;
2-Aminomethyl-5-(3-trifluoromethyl-benzyl)-heptanoic acid;
2-Aminomethyl-5-(4-trifluoromethyl-benzyl)-heptanoic acid;
2-Aminomethyl-5-methyl-7-phenyl-heptanoic acid;
2-Aminomethyl-7-(3-chloro-phenyl)-5-methyl-heptanoic acid;
2-Aminomethyl-5-methyl-7-(3-trifluoromethyl-phenyl)-heptanoic acid;
2-Aminomethyl-5-methyl-7-(4-trifluoromethyl-phenyl)-heptanoic acid;
2-Aminomethyl-7-cyclopropyl-5-ethyl-heptanoic acid;
2-Aminomethyl-7-cyclobutyl-5-ethyl-heptanoic acid;
2-Aminomethyl-7-cyclopentyl-5-ethyl-heptanoic acid;
2-Aminomethyl-7-cyclohexyl-5-ethyl-heptanoic acid;
2-Aminomethyl-5-ethyl-7-phenyl-heptanoic acid;
2-Aminomethyl-7-(3-chloro-phenyl)-5-ethyl-heptanoic acid;
2-Aminomethyl-5-ethyl-7-(3-trifluoromethyl-phenyl)-heptanoic acid;
2-Aminomethyl-5-ethyl-7-(4-trifluoromethyl-phenyl)-heptanoic acid;
2-Aminomethyl-5,5-dimethyl-heptanoic acid;
2-Aminomethyl-5,5-dimethyl-octanoic acid; and
2-Aminomethyl-5,5-dimethyl-nonanoic acid.

This invention also provides pharmaceutical compositions comprising a therapeutically effective amount of a compound of formula I, II, III, IV, V or VI, or a pharmaceutically acceptable salt thereof, and a pharmaceutically acceptable carrier.

This invention also provides a method of treating a disorder or condition in a mammal, including a human, the disorder or condition selected from epilepsy, faintness attacks, fibromyalgia, hypokinesia, cranial disorders, hot flashes, essential tremor, chemical dependencies and addictions, (e.g., dependencies on or addictions to alcohol, amphetamines (or amphetamine-like substances), caffeine, cannabis, cocaine, heroin, hallucinogens, tobacco, inhalants and aerosol propellants, nicotine, opioids, phenylglycidine derivatives, sedatives, hypnotics, benzodiazepines and other anxiolytics), and withdrawal symptoms associated with such dependencies or addictions, addictive behaviors such as gambling; migraine, spasticity including muscle spasticity and hypotonia with paralysis, arthritis, irritable bowel syndrome (IBS), chronic pain, acute pain, neuropathic pain, post herpetic neuralgia, lower back pain, surgical pain, vascular headache, chronic headache, sinus headache, inflammatory disorders (e.g., rheumatoid arthritis, osteoarthritis, disease modification of osteoarthritis disease, psoriasis), diuresis, premenstrual syndrome, premenstrual dysphoric disorder, tinnitus, and gastric damage. The method comprises administering to a mammal in need of such treatment a therapeutically effective amount of a compound of formula I, II, III, IV, V or VI, or a pharmaceutically acceptable salt thereof.

The present invention also provides a method of treating neurodegenerative disorders termed acute brain injury. These include but are not limited to stroke, head trauma, and asphyxia. Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia, such as those that occur in patients undergoing carotid endarterectomy or other cerebrovascular or vascular surgical procedures, or diagnostic vascular procedures including cerebral angiography and the like.

Compounds of formula I, II, III, IV, V or VI, are also useful in the treatment of head trauma, spinal cord trauma, or injury from general anoxia, hypoxia, hypoglycemia, hypotension as well as similar injuries seen during procedures from embole, hyperfusion, and hypoxia. They are also useful in preventing neuronal damage that occurs during cardiac bypass surgery, in incidents of intracranial hemorrhage, in perinatal asphyxia, in cardiac arrest, and status epilepticus.

This invention also provides a method of treating a disorder or condition in a mammal, including a human, the disorder or condition selected from the group consisting of delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; Down's syndrome; demyelinating diseases such as multiple sclerosis (MS) and amylolateral sclerosis (ALS), peripheral neuropathy, for example diabetic and chemotherapy-induced-neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema. The method comprises administering to a mammal in need of such treatment a therapeutically effective amount of a compound of formula I, II, III, IV, V or VI, or a pharmaceutically acceptable salt thereof.

This invention also provides for improving cognition in mammals, including humans, having AD, PD, and fibromyalgia by enhancing the amount and the quality of sleep. The method comprises administering to a mammal in need of improved cognition a therapeutically effective amount of a compound of formula I, II, III, IV, V or VI, or a pharmaceutically acceptable salt thereof.

This invention also provides a method of treating pain in a mammal, including a human, the method comprising administering to a mammal in need of such treatment a therapeutically effective amount of a compound of formula I, II, III, IV, V or VI, or a pharmaceutically acceptable salt thereof. Pain refers to acute as well as chronic pain. Acute pain is usually short-lived and is associated with hyperactivity of the sympathetic nervous system. Examples are postoperative pain and allodynia. Chronic pain is usually defined as pain persisting from three to six months and includes somatogenic pain and psychogenic pain. Other pain is nociceptive.

Examples of the types of pain that can be treated with the compounds of formula I, II, III, IV, V or VI, and their pharmaceutically acceptable salts, include pain resulting from soft tissue and peripheral damage, such as acute trauma, pain associated with osteoarthritis and rheumatoid arthritis, musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, trigeminal neuralgia, neuropathic lower back pain, HIV related neuropathic pain, cancer related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain.

Still other pain is caused by injury or infection of peripheral sensory nerves. It includes, but is not limited to pain from peripheral nerve trauma, herpes virus infection, diabetes mellitus, fibromyalgia, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain include inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

This invention also provides a method of treating depression, which comprises administering to a mammal, including a human, in need of such treatment a therapeutically effective amount of a compound of formula I, II, III, IV, V or VI, or a pharmaceutically acceptable salt thereof. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in *Diagnostic and Statistical Manual of Mental Disorders* (4th ed., 1994), which is referred to as the DSM-IV-R Manual, and is published by the American Psychiatric Association.

This invention also provides a method of treating a disorder or condition in a mammal, including a human, the disorder or condition selected from the group consisting of mood disorders, such as depression, or more particularly, depressive disorders, for example, single episodic or recurrent major depressive disorders, dysthymic disorders, depressive neurosis and neurotic depression, melancholic depression, including anorexia, weight loss, including weight loss associated with anorexia, cancer, old age and/or frailty, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety disorder, social phobia, fear of flying, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; behavioral disturbances associated with mental retardation, autistic disorder, and conduct disorder. The method comprises administering to a mammal in need of such treatment a therapeutically effective amount of a compound of formula I, II, III, IV, V or VI, or a pharmaceutically acceptable salt thereof.

The compounds of the invention are also useful in the treatment of sleep disorders. Sleep disorders are disturbances that affect the ability to fall and/or stay asleep, that involve sleeping too much, or that result in abnormal behavior associated with sleep. The disorders include, for example, insomnia, drug-associated sleeplessness, hypersomnia, narcolepsy, sleep apnea syndromes, parasomnias, restless leg syndrome, jet lag, periodic limb movement disorder, and altered sleep architecture.

This invention also provides a method of treating a disorder or condition in a mammal, including a human, the disorder or condition selected from the group consisting of sleep disorders (e.g., insomnia, drug-associated sleeplessness, REM sleep disorders, hypersomnia, narcolepsy, sleep-wake cycle disorders, sleep apnea syndromes, parasomnias, and sleep disorders associated with shift work and irregular work hours). The method comprises administering to a mammal in need of such treatment a therapeutically effective amount of a compound of formula I, II, III, IV, V or VI, or a pharmaceutically acceptable salt thereof.

Compounds of formulas I, II, III, IV, V or VI contain at least one stereogenic (chiral) center and therefore may exist in different enantiomeric and diastereomeric forms. This invention includes all stereoisomers, including optical isomers, of the compounds of formula I, II, III, IV, V or VI. Samples of the compounds may exist as racemic mixtures, as individual enantiomers and diastereoisomers, and as mixtures thereof. The invention also includes all pharmaceutical compositions and methods of treatment defined above that contain or employ stereoisomers of the compounds of formula I, II, III, IV, V or VI.

This invention also provides a method of making a compound of formula IV and its pharmaceutically acceptable salts. The method comprises treating a compound of formula 39,

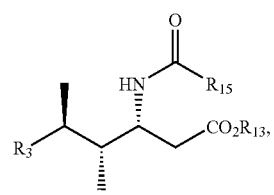

39 with an acid to give a hydrolysis product, and optionally treating the hydrolysis product with an acid or base to give the compound of formula IV or a pharmaceutically acceptable salt thereof. In formula 39, $R_3$ is as defined above in formula IV, and $R_{13}$ and $R_{15}$ are independently $(C_1-C_6)$alkyl, $(C_3-C_6)$cycloalkyl, or $(C_3-C_6)$cycloalkyl-$(C_1-C_3)$alkyl.

This invention provides another method of making the compound of formula IV or its pharmaceutically acceptable salts. The method comprises reacting a compound of formula 36,

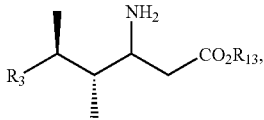

36 with $H_2$ in the presence of a catalyst to give the compound of formula 41,

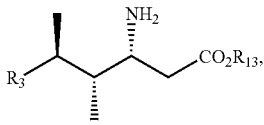

41 and treating the compound of formula 41 with an acid or base to give a hydrolysis product. The method also includes treating the hydrolysis product with a second base or acid to give the compound of formula IV or a pharmaceutically acceptable salt thereof. In formula 36 and formula 41, $R_3$ and $R_{13}$ are as defined above with respect to formula IV and formula 39, respectively.

In addition to the compounds of formula 36, 39, and 41, and their salts, this invention also provides the following compounds or salts thereof:

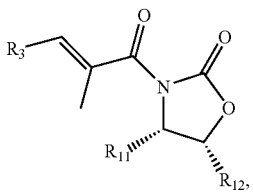

28

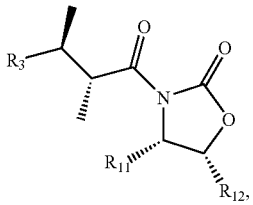

29

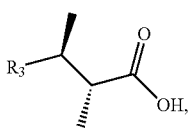

30

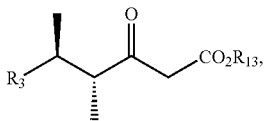

33

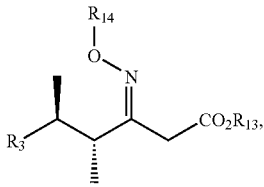

35

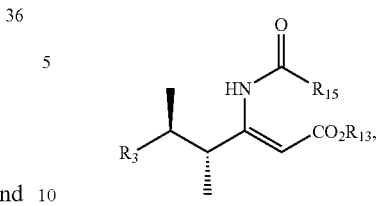

38 wherein $R_3$ is as defined above with respect to formula IV, and $R_{13}$, and $R_{15}$ are as defined above with respect to formula 39;

$R_{11}$ and $R_{12}$ are independently hydrogen, $(C_1-C_3)$alkyl, phenyl, or benzyl, provided that $R_{11}$ and $R_{12}$ are not both hydrogen;

$R_{13}$ and $R_{15}$ are independently $(C_1-C_6)$alkyl, $(C_3-C_6)$cycloalkyl, or $(C_3-C_6)$cycloalkyl-$(C_1-C_3)$alkyl; and $R_{14}$ is $(C_1-C_6)$alkyl, $(C_3-C_6)$cycloalkyl, $(C_3-C_6)$cycloalkyl-$(C_1-C_3)$alkyl, or silyl.

Compounds with one stereogenic center may exist as a racemic (equimolar) mixture, as a non-equimolar mixture of isomers, and as pure enantiomers having S- or R-stereoconfiguration. Compounds with two stereogenic centers may exist as a racemic mixture, as a non-equimolar mixture of isomers, and as pure enantiomers having SS, RR, SR or RS stereoconfiguration. Compounds with three stereogenic centers may exist as a racemic mixture, as a non-equimolar mixture of isomers, and as pure enantiomers having RRR, SSS, SRR, RSS, RSR, SRS, RRS or SSR stereoconfiguration. Individual isomers may be obtained by known methods, such as optical resolution, optically selective reaction, or chromatographic separation in the preparation of the final product or its intermediate. Individual enantiomers of the compounds of this invention may have advantages, as compared with racemic mixtures of these compounds, in the treatment of various disorders or conditions.

The present invention also includes isotopically labeled compounds, which are identical to those recited in formula I, II, III, IV, V, or VI but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I, II, III, IV, V, or VI of this invention and prodrugs thereof can generally be prepared by carrying out the procedures disclosed in the Schemes and/or in the Examples and Preparations below, by substituting a readily available isotopically labeled reagent for a non-isotopically labeled reagent.

Unless otherwise indicated, this disclosure uses definitions provided below. Some of the definitions and formulae may include a "—" (dash) to indicate a bond between atoms or a point of attachment to a named or unnamed atom or group of atoms. Other definitions and formulae may include an "=" (equal sign) or "≡" (identity sign) to indicate a double bond or a triple bond, respectively. Certain formulae may also include an "*" (asterisk) to indicate a stereogenic (chiral) center. Such formulae may refer to the racemate or to individual enantiomers, which may or may not be substantially pure.

The term "substituted" when used in connection with a compound, substituent, or moiety, indicates that one or more hydrogen atoms have been replaced with one or more non-hydrogen atoms or groups, provided that valence requirements are met and that a chemically stable compound results from the substitution.

The term "alkyl" refers to straight chain and branched saturated hydrocarbon groups, generally having a specified number of carbon atoms; i.e., ($C_1$-$C_6$)alkyl refers to an alkyl group having 1, 2, 3, 4, 5, or 6 carbon atoms. Examples of alkyl groups include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, 3-ethylbutyl, and the like.

The term "cycloalkyl" refers to saturated monocyclic and bicyclic hydrocarbon rings, generally having a specified number of carbon atoms that comprise the ring; i.e., ($C_3$-$C_6$)cycloalkyl refers to a cycloalkyl group having 3, 4, 5, or 6 carbon atoms as ring members. The cycloalkyl may be attached to a parent group or to a substrate at any ring atom, unless such attachment would violate valence requirements. Likewise, the cycloalkyl groups may include one or more non-hydrogen substituents unless such substitution would violate valence requirements. Useful substituents include, without limitation, alkyl, as defined above, and hydroxy, mercapto, nitro, halogen, and amino.

Examples of monocyclic cycloalkyl groups include, without limitation, cyclopropyl, cyclobutyl, cyclopentyl, cyclohexyl, and the like. Examples of bicyclic cycloalkyl groups include, without limitation, bicyclo[1.1.0]butyl, bicyclo [1.1.1]pentyl, bicyclo[2.1.0]pentyl, bicyclo[2.1.1]hexyl, bicyclo[3.1.0]hexyl, bicyclo[2.2.1]heptyl, bicyclo[3.2.0] heptyl, bicyclo[3.1.1]heptyl, bicyclo[4.1.0]heptyl, bicyclo [2.2.2]octyl, bicyclo[3.2.1]octyl, bicyclo[4.1.1]octyl, bicyclo[3.3.0]octyl, bicyclo[4.2.0]octyl, bicyclo[3.3.1]nonyl, bicyclo[4.2.1]nonyl, bicyclo[4.3.0]nonyl, bicyclo[3.3.2]decyl, bicyclo[4.2.2]decyl, bicyclo[4.3.1]decyl, bicyclo[4.4.0] decyl, bicyclo[3.3.3]undecyl, bicyclo[4.3.2]undecyl, bicyclo[4.3.3]dodecyl, and the like.

The term "alkoxy" refers to alkyl-O—, where alkyl is defined above. Examples of alkoxy groups include, without limitation, methoxy, ethoxy, n-propoxy, i-propoxy, n-butoxy, s-butoxy, t-butoxy, n-pentoxy, s-pentoxy, and the like.

The term "treating" refers to reversing, alleviating, inhibiting the progress of, or preventing the disorder or condition to which such term applies, or preventing one or more symptoms of such condition or disorder. The term "treatment," as used herein, refers to the act of treating, as "treating" is defined immediately above.

The phrase "leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts), sulfonates (including tosylates, brosylates, nosylates, and mesylates), triflates, nonaflates, tresylates, halide ions, carboxylate anions, phenolate ions, and alkoxides. Some stronger bases, such as $NH_2$— and OH— can be made better leaving groups by treatment with an acid. Common electrofugal leaving groups include the proton, $CO_2$, and metals.

The phrase "enantiomeric excess" or "ee" is a measure, for a given sample, of the excess of one enantiomer over a racemic sample of a chiral compound and is expressed as a percentage. Enantiomeric excess is defined as 100×(er−1)/ (er+1), where "er" is the ratio of the more abundant enantiomer to the less abundant enantiomer.

The phrase "diastereomeric excess" or "de" is a measure, for a given sample, of the excess of one diastereomer over a sample having equal amounts of diastereomers and is expressed as a percentage. Diastereomeric excess is defined as 100×(dr−1)/(dr+1), where "dr" is the ratio of a more abundant diastereomer to a less abundant diastereomer. The term does not apply if more than two diastereomers are present in the sample.

The terms "stereoselective," "enantioselective," and "diastereoselective," and variants thereof, refer to a given reaction (e.g., hydrogenation) that yields more of one stereoisomer, enantiomer, or diastereoisomer than another, respectively.

The phrases "high level of enantioselectivity" and "high level of diastereoselectivity" refer to a given reaction that yields product with an ee or de, respectively, of at least about 80%.

The phrases "enantiomerically enriched" and "diastereomerically enriched" refer, respectively, to a sample of a compound that has more of one enantiomer or diastereomer than another. The degree of enrichment is measured by, respectively, er or ee, or by dr or er.

The phrases "substantially pure enantiomer" or "substantially enantiopure" and "substantially pure diastereomer" or "substantially diastereopure" refer, respectively, to a sample of an enantiomer or diastereomer having an ee or de of about 90% or greater.

The phrases "enantiomerically pure" or "enantiopure" and "diastereomerically pure" or "diastereopure" refer, respectively, to a sample of an enantiomer or diastereomer having an ee or de of about 99% or greater.

The phrase "opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

The phrase "pharmaceutically acceptable salts, esters, amides, and prodrugs" refers to acid or base addition salts, esters, amides, zwifterionic forms, where possible, and prodrugs of claimed and disclosed compounds, which are within the scope of sound medical judgment, suitable for use in contact with the tissues of patients without undue toxicity, irritation, allergic response, and the like, commensurate with a reasonable benefit/risk ratio, and effective for their intended use.

Because amino acids are amphoteric, pharmacologically compatible salts can be salts of appropriate inorganic or organic acids, for example, hydrochloric, sulfuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethylammonium ion.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug that has been chemically modified and may be biologically inactive at its site of action, but which may be degraded or modified by one or more enzymatic or other in vivo processes to the parent bioactive form.

This chemically modified drug, or prodrug, should have a different pharmacokinetic profile than the parent drug, enabling easier absorption across the mucosal epithelium, better salt formulation, improved solubility, enhanced systemic stability (for an increase in plasma half-life, for example), and the like. These chemical modifications include, but are not limited to (1) ester or amide derivatives which may be cleaved by, for example, esterases or lipases; (2) peptides, which may be recognized by specific or non-specific proteinases; (3) derivatives that accumulate at a site of action through membrane selection of a prodrug form or modified prodrug form; and (4) any combination of (1) to (3). The ester or amides prodrugs may be derived from the carboxylic acid moiety of the parent drug molecule or from the carboxylic acid moiety or the amine moiety of the parent drug molecule, respectively, by known means. In addition, the peptide prodrug may be coupled to the parent drug molecule via amide bond formation with the amine or carboxylic acid moiety of the parent drug molecule using known techniques.

Current research in animal experiments has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug upon hydrolysis.

Soft quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the soft quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Prodrugs of compounds of formula I, II, III, IV, V or VI are included within the scope of this invention. For a discussion of prodrugs and soft drugs, see E. Palomino, *Drugs of the Future* 15(4):361-68 (1990). See also, T. Higuchi and V. Stella, "Pro-drugs as Novel Delivery Systems," *ACS Symposium Series* 14 (1975); E. B. Roche (ed.), *Bioreversible Carriers in Drug Design* (1987); and H. Bundgaar, *Design of Prodrugs* (1985).

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

DETAILED DESCRIPTION

The compounds of this invention can be prepared as described below. In the reaction schemes and discussion that follow, structural formulas I, II, III, IV, V, or VI, and the radicals $R_1$, $R_2$, $R_3$, $R_4$, $R_5$ and $R_6$, unless otherwise indicated, are as defined above.

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and the like, see T. W. Greene and P. G. Wuts, *Protecting Groups in Organic Chemistry* (1999) and P. Kocienski, *Protective Groups* (2000).

In addition, some of the schemes and examples below may omit details of common reactions, including oxidations, reductions, and so on, which are known to persons of ordinary skill in the art of organic chemistry. The details of such reactions can be found in a number of treatises, including Richard Larock, *Comprehensive Organic Transformations* (1999), and the multi-volume series edited by Michael B. Smith and others, *Compendium of Organic Synthetic Methods* (1974-2003). Generally, starting materials and reagents may be obtained from commercial sources.

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about RT (room temperature, 20° C. to 25° C., inclusive), but some reactions may use higher (e.g., reflux temperatures) or lower temperatures (e.g., −78° C.), depending on reaction kinetics, yields, selectivity, and the like. Furthermore, many of the chemical transformations may employ one or more compatible solvents, which depending on the nature of the reactants, may be polar protic solvents, polar aprotic solvents, non-polar solvents, or some combination. Although the choice of solvent or solvents may influence the reaction rate and yield, such solvents are generally considered to be inert (unreactive). Any references in the disclosure to a concentration range, a temperature range, a pH range, a catalyst loading range, and so on, whether expressly using the word "range" or not, includes the indicated endpoints.

Diverse methods exist for the preparation of chiral and racemic β-amino acids. Such methods can be found in Eusebio Juaristi (editor), *Enantioselective Synthesis of β-Amino Acids* (1997).

The methods described below are illustrative of methods that can be utilized for the preparation of such compounds but are not limiting in scope.

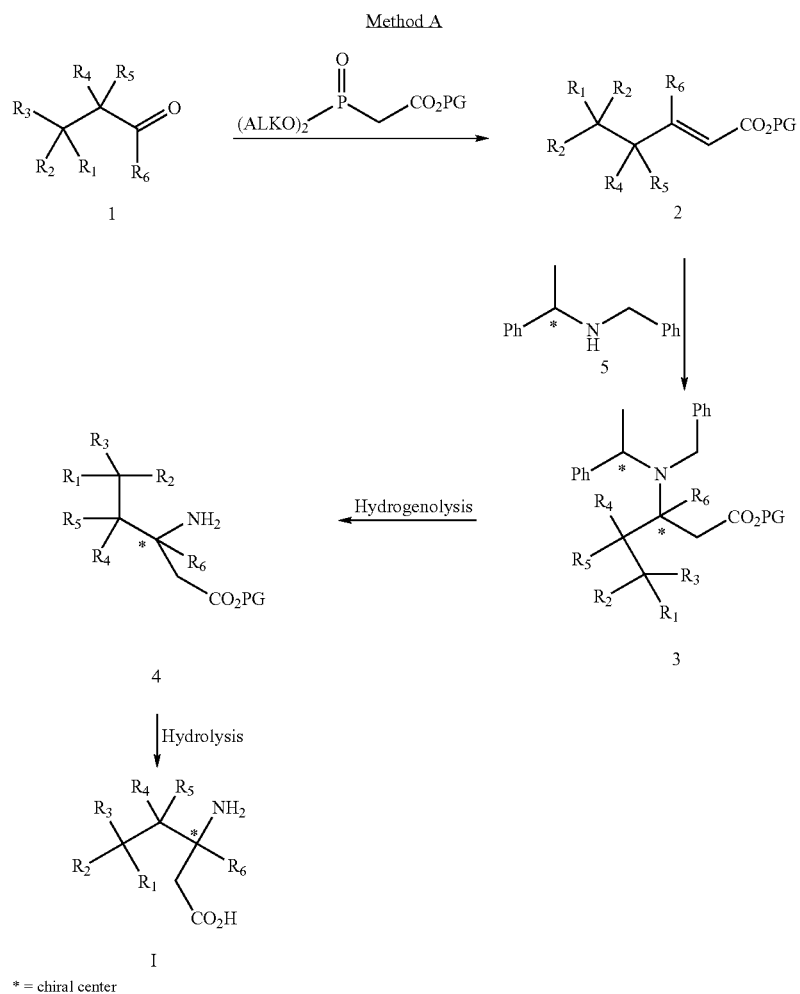

Method A

* = chiral center

The use of chiral amine additions to α,β-unsaturated systems as a synthetic approach to β-amino acids, as illustrated in Method A above, has been described previously. See, e.g., S. G. Davies et al, *J. Chem. Soc. Chem. Commun.* 1153 (1993); S. G. Davies, *Synlett* 117 (1994); Ishikawa et al, *Synlett* 1291 (1998); and Hawkins, *J. Org. Chem.* 51:2820 (1985). Referring to Method A above, compounds of formula I can be prepared from the corresponding compounds of formula 4, wherein PG represents a suitable ester protecting group that can be removed by hydrolysis or hydrogenolysis, using conditions well known to those of skill in the art. See T. W. Greene and P. G. M. Wuts, *Protective groups in organic synthesis* (1991) for a detailed description for the formation and removal of suitable protecting groups). For example, this reaction can be conducted under hydrolytic conditions by treatment with an appropriate acid, such as hydrochloric acid or sulfuric acid, at a temperature from about room temperature to about the reflux temperature of the reaction mixture, preferably at the reflux temperature, or by treatment with an appropriate inorganic base, such as sodium hydroxide, potassium hydroxide, or lithium hydroxide, preferably sodium hydroxide, at a temperature from about room temperature to about the reflux temperature, preferably at about room temperature. This reaction is preferably carried out using hydrochloric acid at the reflux temperature. When PG is t-butyl, however, the reaction is preferably carried out in trifluoroacetic acid (TFA). When PG is a basic group, the hydrolysis can be carried out under basic conditions, using methods well known to those of skill in the art, for example, using sodium or potassium hydroxide.

Compounds of formula 4 can be prepared from the corresponding compounds of formula 3 using hydrogenolysis conditions that are well known to those of skill in the art. For example, this reaction can be carried out by treating the compounds of formula 3 with a palladium metal catalyst, such as, for example, palladium hydroxide on carbon, or palladium on carbon, or with Raney Nickel, in a solvent such as, for example, methanol, ethanol or tetrahydrofuran, under an atmosphere of hydrogen (between about 1 and 5 atmospheres of pressure) to give the desired compound of formula 4. Preferably, the reaction is carried out using palladium on carbon in ethanol under about 1 atmosphere of hydrogen.

Compounds of formula 3 can be prepared by treating the corresponding compounds of formula 2 with an appropriate amine such as (R)-(+)-N-benzyl-α-methylbenzylamine, (S)-(−)-N-benzyl-α-methylbenzylamine after treatment with an appropriate base such as lithium diisopropylamide, n-butyl lithium, or lithium or potassium bis(trimethylsilyl)amide, in a solvent such as ethyl ether, or, preferably, tetrahydrofuran (THF), at a temperature from about −80° C. to about 25° C., and then adding the appropriate compound of formula 2. The stereochemistry about the nitrogen of the amine will determine the stereochemistry about the nitrogen of the final product. Preferably, this reaction is carried out using either (R)-(+)-N-benzyl-α-methylbenzylamine, (S)-(−)-N-benzyl-α-methylbenzylamine, after deprotonation with n-butyl-lithium in tetrahydrofuran, at a temperature of about −78° C., according to method described by S. D. Bull et al., *J. Chem. Soc., Perkin Trans.* 1 22:2931-38 (2001). Preferably, this reaction is carried out using either (R)-(+)-N-benzyl-α-methylbenzylamine, or (S)-(−)-N-benzyl-α-methylbenzylamine, after deprotonation with n-butyl-lithium in tetrahydrofuran, at a temperature of about −78° C., according to method described by S. D. Bull et al., *J. Chem. Soc., Perkin Trans.* 1 22:2931-38 (2001).

Compounds of formula 2 can be prepared from the corresponding compounds of formula 1 by treating them with an appropriate phosphonate ester in the presence of a suitable base such as sodium hydride, lithium diisopropylamide, or triethyl amine and either lithium chloride or lithium bromide, in a solvent such as ether or THF. Preferably, the compound of formula 1 is reacted with a phosphonate ester (ALK=methyl, ethyl, isopropyl, benzyl or the like) in the presence of lithium bromide and triethylamine in tetrahydrofuran at about room temperature. Compounds of formula 1 can be prepared from commercially available materials using methods well known to those of skill in the art. It will be appreciated that compounds of formula I may possess one or more stereogenic centers. Using the above-described method, compounds with specific stereochemical configurations can be prepared.

Compounds that can be made by this method include, but are not limited to the following:
3-Amino-4,5-dimethyl-hexanoic acid;
3-Amino-4,5-dimethyl-heptanoic acid;
3-Amino-4,5-dimethyl-octanoic acid;
3-Amino-4,5-dimethyl-nonanoic acid;
3-Amino-4-ethyl-5-methyl-heptanoic acid;
3-Amino-4-ethyl-5-methyl-octanoic acid;
3-Amino-4-ethyl-5-methyl-nonanoic acid;
3-Amino-4-ethyl-5,6-dimethyl-heptanoic acid;
3-Amino-4-ethyl-5,7-dimethyl-octanoic acid;
3-Amino-4-ethyl-5,8-dimethyl-nonanoic acid;
(3R,4R)-3-Amino-4,5-dimethyl-hexanoic acid;
(3R,4R,5R)-3-Amino-4,5-dimethyl-heptanoic acid;
(3R,4R,5R)-3-Amino-4,5-dimethyl-octanoic acid;
(3R,4R,5R)-3-Amino-4,5-dimethyl-nonanoic acid;
(3R,4R,5R)-3-Amino-4,5-dimethyl-decanoic acid;
3-Amino-4,6-dimethyl-heptanoic acid;
3-Amino-4,6-dimethyl-octanoic acid;
3-Amino-4,6-dimethyl-nonanoic acid;
3-Amino-4,6-dimethyl-decanoic acid;
3-Amino-4,6,7-trimethyl-octanoic acid;
3-Amino-4,6,8-trimethyl-nonanoic acid;
3-Amino-4,6,9-trimethyl-decanoic acid;
3-Amino-6-cyclopropyl-4-methyl-heptanoic acid;
3-Amino-6-cyclobutyl-4-methyl-heptanoic acid;
3-Amino-6-cyclopentyl-4-methyl-heptanoic acid;
3-Amino-6-cyclohexyl-4-methyl-heptanoic acid;
3-Amino-7-cyclopropyl-4,6-dimethyl-heptanoic acid;
3-Amino-7-cyclobutyl-4,6-dimethyl-heptanoic acid;
3-Amino-7-cyclopentyl-4,6-dimethyl-heptanoic acid;
3-Amino-7-cyclohexyl-4,6-dimethyl-heptanoic acid;
3-Amino-8-cyclopropyl-4,6-dimethyl-octanoic acid;
3-Amino-8-cyclobutyl-4,6-dimethyl-octanoic acid;
3-Amino-8-cyclopentyl-4,6-dimethyl-octanoic acid;
3-Amino-8-cyclohexyl-4,6-dimethyl-octanoic acid;
3-Amino-6-(3-chloro-phenyl)-4-methyl-heptanoic acid;
3-Amino-6-(3,4-dichloro-phenyl)-4-methyl-heptanoic acid;
3-Amino-4-methyl-6-(3-trifluoromethyl-phenyl)-heptanoic acid;
3-Amino-4-methyl-6-(4-trifluoromethyl-phenyl)-heptanoic acid;
3-Amino-7-(3-chloro-phenyl)-4,6-dimethyl-heptanoic acid;
3-Amino-7-(3,4-dichloro-phenyl)-4,6-dimethyl-heptanoic acid;
3-Amino-4,6-dimethyl-7-(3-trifluoromethyl-phenyl)-heptanoic acid;
3-Amino-4,6-dimethyl-7-(4-trifluoromethyl-phenyl)-heptanoic acid;
3-Amino-8-(3-chloro-phenyl)-4,6-dimethyl-octanoic acid;
3-Amino-8-(3,4-dichloro-phenyl)-4,6-dimethyl-octanoic acid;
3-Amino-4,6-dimethyl-8-(3-trifluoromethyl-phenyl)-octanoic acid;
3-Amino-4,6-dimethyl-8-(4-trifluoromethyl-phenyl)-octanoic acid;
3-Amino-4-ethyl-6-methyl-octanoic acid;
3-Amino-4-ethyl-6-methyl-nonanoic acid;
3-Amino-4-ethyl-6-methyl-decanoic acid;
3-Amino-4-ethyl-6,7-dimethyl-octanoic acid;
3-Amino-4-ethyl-6,8-dimethyl-nonanoic acid;
3-Amino-4-ethyl-6,9-dimethyl-decanoic acid;
3-Amino-6-cyclopropyl-4-ethyl-heptanoic acid;
3-Amino-6-cyclobutyl-4-ethyl-heptanoic acid;
3-Amino-6-cyclopentyl-4-ethyl-heptanoic acid;
3-Amino-6-cyclohexyl-4-ethyl-heptanoic acid;
3-Amino-7-cyclopropyl-4-ethyl-6-methyl-heptanoic acid;
3-Amino-7-cyclobutyl-4-ethyl-6-methyl-heptanoic acid;
3-Amino-7-cyclopentyl-4-ethyl-6-methyl-heptanoic acid;
3-Amino-7-cyclohexyl-4-ethyl-6-methyl-heptanoic acid;
3-Amino-8-cyclopropyl-4-ethyl-6-methyl-octanoic acid;
3-Amino-8-cyclobutyl-4-ethyl-6-methyl-octanoic acid;
3-Amino-8-cyclopentyl-4-ethyl-6-methyl-octanoic acid;
3-Amino-8-cyclohexyl-4-ethyl-6-methyl-octanoic acid;
3-Amino-6-(3-chloro-phenyl)-4-ethyl-heptanoic acid;
3-Amino-6-(3,4-dichloro-phenyl)-4-ethyl-heptanoic acid;
3-Amino-4-ethyl-6-(3-trifluoromethyl-phenyl)-heptanoic acid;
3-Amino-4-ethyl-6-(4-trifluoromethyl-phenyl)-heptanoic acid;
3-Amino-7-(3-chloro-phenyl)-4-ethyl-6-methyl-heptanoic acid;
3-Amino-7-(3,4-dichloro-phenyl)-4-ethyl-6-methyl-heptanoic acid;
3-Amino-4-ethyl-6-methyl-7-(3-trifluoromethyl-phenyl)-heptanoic acid;
3-Amino-4-ethyl-6-methyl-7-(4-trifluoromethyl-phenyl)-heptanoic acid;
3-Amino-8-(3-chloro-phenyl)-4-ethyl-6-methyl-octanoic acid;
3-Amino-8-(3,4-dichloro-phenyl)-4-ethyl-6-methyl-octanoic acid;
3-Amino-4-ethyl-6-methyl-8-(3-trifluoromethyl-phenyl)-octanoic acid; and
3-Amino-4-ethyl-6-methyl-8-(4-trifluoromethyl-phenyl)-octanoic acid.

Method B

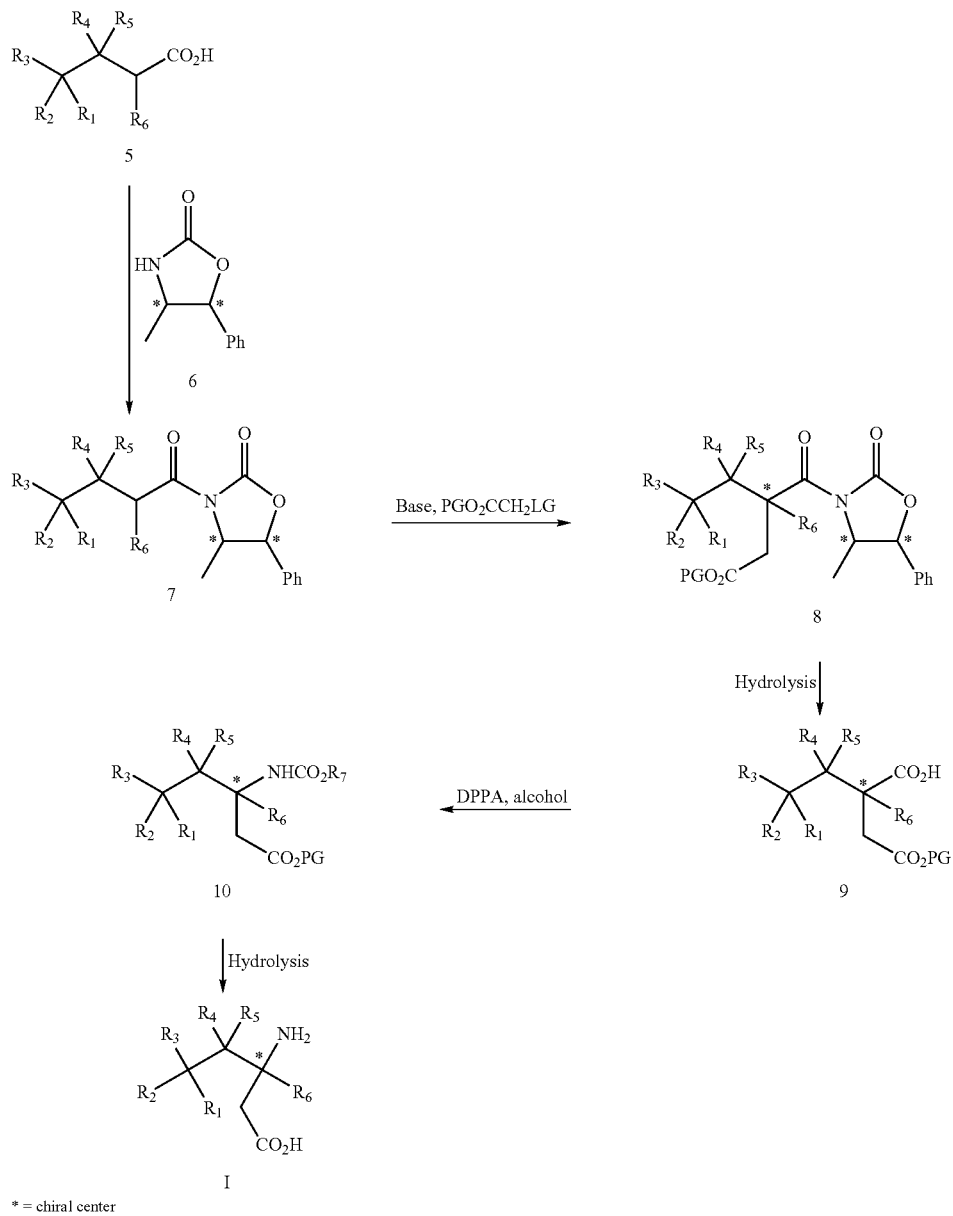

\* = chiral center

The diastereoselective alkylation of imides such as those of formula 7 to afford chiral succinate analogs such as those of formula 8 has been previously described as an approach to preparing β-amino acids. See, e.g., Evans et al, *J. Org. Chem.* 64:6411 (1999); Sibi and Deshpande, *J. Chem. Soc. Perkin Trans* 1 1461 (2000); and Arvanitis et al, *J. Chem. Soc. Perkin Trans* 1 521 (1998).

Compounds of formula 8 can be prepared from compounds of formula 7 in the presence of a suitably derived ester (PG as defined above, LG=Br or I or Cl) such as, for example, t-butyl bromoacetate, benzyl bromoacetate with an organometallic base such as, for example, lithium diisopropylamide or lithium bis(trimethylsilyl)amide or sodium bis (trimethylsilyl)amide and the like in a solvent such as, for example, tetrahydrofuran, ether, and the like. The reaction can be carried out using sodium bis(trimethylsilyl)amide in tetrahydrofuran at −78° C. and treatment of the resultant anion intermediate with t-butyl bromoacetate at −78° C. to −30° C.

Compounds of formula 9 can be prepared by hydrolyzing the corresponding compounds of formula 8 in the presence of lithium hydroxide and hydrogen peroxide in a solvent such as water or THF, at a temperature from about 0° C. to about room temperature. Preferably, this reaction is carried out using hydrogen peroxide and lithium hydroxide in aqueous tetrahydrofuran at about 0° C. according to the method described in the literature. See P.-W. Yuen et al., *Bioorganic and Medicinal Chem. Lett.* 4(6):823-26 (1994).

Treatment of the compound of formula 9 with diphenylphosphorylazide (DPPA) followed by treatment with a suitable alcohol such as t-butanol, benzyl alcohol or p-methoxybenzyl alcohol, in a suitable solvent such as toluene, benzene, MTBE, or THF, at a temperature from about 50° C. to about the reflux temperature of the reaction mixture yields the corresponding compound of formula 10, wherein $R_7$ is methyl, ethyl, t-butyl, benzyl, or p-methoxybenzyl. $R_7$ is dependent on the choice of the alcohol used. Preferably, this reaction is carried out using a toluene solvent in the presence of p-methoxybenzyl alcohol under refluxing conditions.

Compounds of formula 10 can be converted into the desired compounds of formula I by hydrolysis or hydrogenolysis, using conditions well known to those of skill in the art. See T. W. Greene and P. G. M. Wuts, *Protective groups in organic synthesis* (1991) for a detailed description for the formation and removal of suitable protecting groups. For example, this reaction can be conducted under hydrolytic conditions by treatment with an appropriate acid, such as hydrochloric acid or sulfuric acid, at a temperature from about room temperature to about the reflux temperature of the reaction mixture, preferably at the reflux temperature, or by treatment with an appropriate inorganic base, such as sodium hydroxide, potassium hydroxide, or lithium hydroxide, preferably sodium hydroxide, at a temperature from about room temperature to about the reflux temperature, preferably at about room temperature. This reaction is preferably carried out using hydrochloric acid at the reflux temperature. When PG is t-butyl, however, the reaction is preferably carried out in trifluoroacetic acid (TFA). When PG is a basic group, the hydrolysis can be carried out under basic conditions, using methods well known to those of skill in the art, for example, using sodium or potassium hydroxide.

Compounds of formula 7 can be prepared by treating the corresponding compounds of formula 5 with an amine base such as triethylamine, in the presence of trimethylacetylchloride, in an ethereal solvent such as THF, and then treating the intermediates formed by this reaction (in situ) with a chiral oxazolidinone of formula 6. Examples of other oxazolidinones that can be used in this method are: (4S)-(−)-4-isopropyl-2-oxazolidinone; (S)-(−)-4-benzyl-2-oxazolidinone; (4S,5R)-(−)-4-methyl-5-phenyl-2-oxazolidinone; (R)-(+)-4-benzyl-2-oxazolidinone, (S)-(+)-4-phenyl-2-oxazolidinone; (R)-(−)-4-phenyl-2-oxazolidinone; (R)-4-isopropyl-2-oxazolidinone; and (4R,5S)-(+)-4-methyl-5-phenyl-2-oxazolidinone)) and lithium chloride. Preferably, this reaction is carried out by treating an acid of formula 5 with trimethylacetylchloride and triethylamine in tetrahydrofuran at about −20° C., followed by treatment of the intermediate formed in such reaction with an oxazolidinone of formula 6 and lithium chloride at about room temperature according to literature procedures. See G.-J. Ho and D. J. Mathre, *J. Org. Chem.* 60:2271-73 (1995).

Alternatively, compounds of formula 7 can be prepared by treating the corresponding compounds of formula 6 with an acid chloride derived from treatment of the corresponding compound of formula 5 with oxalyl chloride, in a solvent such as dichloromethane, in the presence of dimethylformamide (DMF). Acids of formula 5 can be prepared from commercially available materials using methods well known to those of skill in the art. These acids may possess one or more stereogenic centers.

Alternatively, referring to Method C below, compounds of formula 8 can be treated with an appropriate acid (for example, trifluoroacetic acid (TFA) when the t-butyl ester is used) to yield the corresponding compounds of formula 12, which can then be subjected to a Curtius rearrangement (where $R_7$ is defined as above) to yield the corresponding compounds of formula 13. See Arvanitis et al, *J. Chem. Soc. Perkin Trans* 1 521 (1998) for a description of this approach. Further hydrolysis of the imide group yields the corresponding compound of formula 14; hydrolysis of the resulting carbamate group in formula 14 gives the desired β-amino acids of formula V.

Compounds of formula 13 may be converted to compounds of formula 14 in a manner similar to the method for converting compounds of formula 8 into compounds of formula 9 (Method B). Furthermore, compounds of formula 14 may be converted to compounds of formula II through treatment with a strong acid, such as hydrochloric acid or the like, or a strong base, such as sodium or potassium hydroxide or, if $R_7$ is benzyl or p-methoxybenzyl, through hygrogenolytic conditions, using palladium on carbon in ethanol or THF under a hydrogen atmosphere. This approach, which preserves the stereochemistry about the stereogenic center in the compounds of formula 8 and formula II, is utilized in Example 4 below.

Method C

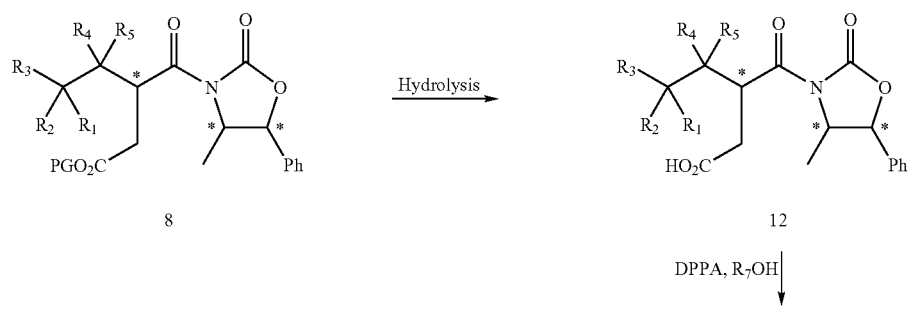

-continued

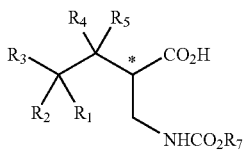

14

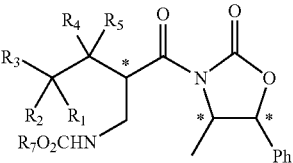

13

Hydrolysis

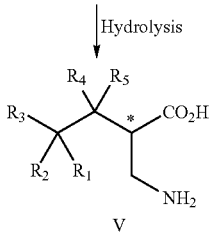

V

* = chiral center

Other alternative approaches to synthesizing α-substituted β-amino acids that can be utilized for preparing the compounds of this invention. See, e.g., Juaristi et al., *Tetrahedron Asymm.* 7(8):2233 (1996); Seebach et al., *Eur. J. Org. Chem.* 335 (1999); Nagula et al., *Org, Lett*, 2:3527 (2000); Arvanitis et al., *J. Chem. Soc. Perkin Trans* 1 521 (1998); and Hintermann et al., *Helv. Chim. Acta* 81:2093 (1998), as shown in Method D below.

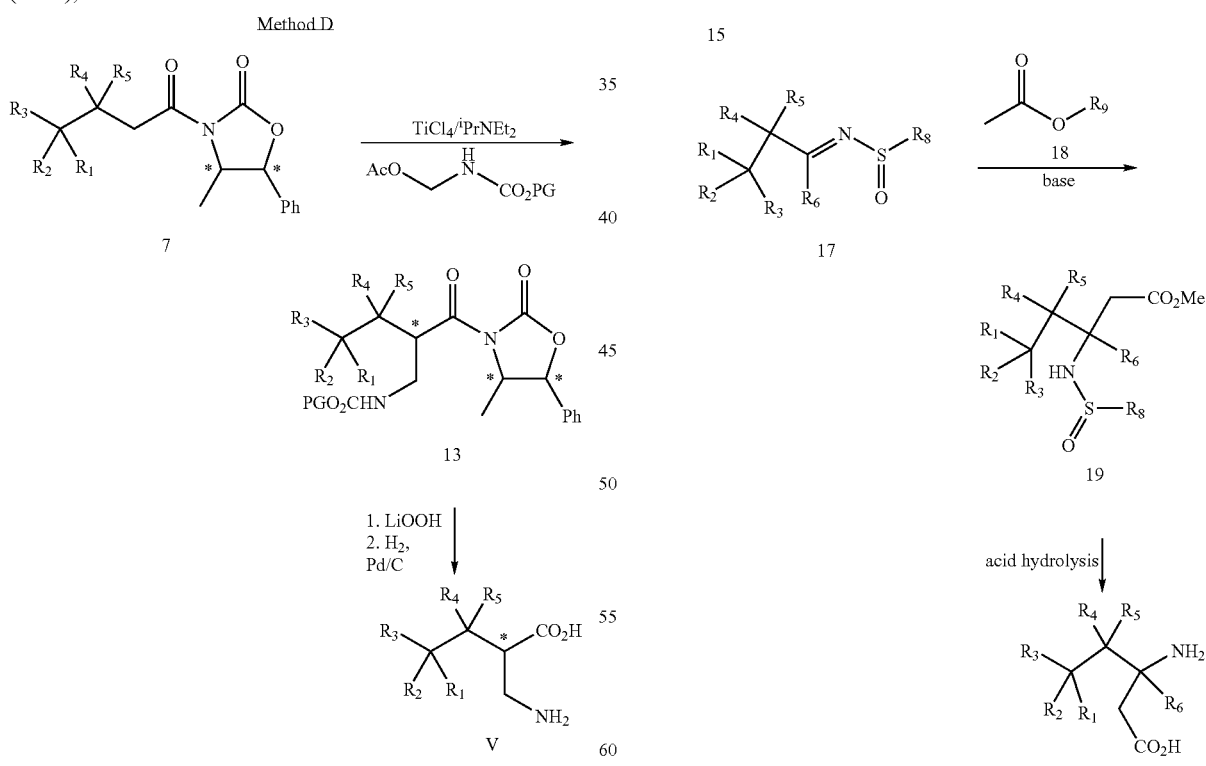

The use of chiral sulfimines to afford β-amino acids, as illustrated in Method E below, has been described previously. See, e.g., T. P. Tang and J. A. Ellman, *J. Org. Chem.* 64:12-13 (1999); Davis and McCoull, *J. Org. Chem.* 64:3396-97 (1999), and Davis et al., *J. Org. Chem.* 64:1403-06 (1999).

The final step in the above scheme ($R_8$=t-butyl or p-tolyl, $R_9$=a suitably derived ester such as methyl, ethyl or t-butyl) is a hydrolysis of both the sulfonamide and ester groups of a compound of formula 19 to give a compound of formula I. This reaction is generally carried out using a strong acid such as trifluoroacetic acid, hydrochloric acid, hydrobromic acid or sulfuric acid, in a solvent such as water or dioxane or a mixture of water and dioxane, at a temperature from about 20° C. to about 100° C., preferably at about room temperature. The reaction may be carried out by treating compounds of formula 19 with an acid such as TFA in a solvent such as methanol then treating the product with TFA in a solvent such as dichloromethane to give a compound of formula I.

Compounds that can be made by this method include, but are not limited to the following:
3-Amino-4,5-dimethyl-hexanoic acid;
3-Amino-4,5-dimethyl-heptanoic acid;
3-Amino-4,5-dimethyl-octanoic acid;
3-Amino-4,5-dimethyl-nonanoic acid;
3-Amino-4-ethyl-5-methyl-heptanoic acid;
3-Amino-4-ethyl-5-methyl-octanoic acid;
3-Amino-4-ethyl-5-methyl-nonanoic acid;
3-Amino-4-ethyl-5-methyl-decanoic acid;
3-Amino-4-ethyl-5,6-dimethyl-heptanoic acid;
3-Amino-4-ethyl-5,7-dimethyl-octanoic acid;
3-Amino-4-ethyl-5,8-dimethyl-nonanoic acid;
3-Amino-5-ethyl-4-methyl-octanoic acid;
3-Amino-5-ethyl-4-methyl-nonanoic acid;
3-Amino-4,5-diethyl-heptanoic acid;
3-Amino-4,5-diethyl-octanoic acid;
3-Amino-4,5-diethyl-nonanoic acid;
3-Amino-5-ethyl-4,7-dimethyl-octanoic acid;
3-Amino-5-ethyl-4,8-dimethyl-nonanoic acid;
3-Amino-4,5-diethyl-6-methyl-heptanoic acid;
3-Amino-4,5-diethyl-7-methyl-octanoic acid;
3-Amino-4,5-diethyl-8-methyl-nonanoic acid;
3-Amino-4,5,6-trimethyl-heptanoic acid;
3-Amino-4,5,7-trimethyl-octanoic acid;
3-Amino-4,5,8-trimethyl-nonanoic acid;
3-Amino-4-ethyl-5-methyl-hexanoic acid;
3-Amino-5-ethyl-4-methyl-octanoic acid;
3-Amino-5-ethyl-4-methyl-heptanoic acid;
3-Amino-4-methyl-5-propyl-octanoic acid;
3-Amino-6-cyclopentyl-4,5-dimethyl-hexanoic acid;
3-Amino-7-cyclopentyl-4,5-dimethyl-heptanoic acid;
3-Amino-5-ethyl-4,6-dimethyl-heptanoic acid;
3-Amino-5-ethyl-4,7-dimethyl-octanoic acid;
3-Amino-5-ethyl-4,8-dimethyl-nonanoic acid;
(3R,4R)-3-Amino-4,5-dimethyl-hexanoic acid;
(3R,4R,5R)-3-Amino-4,5-dimethyl-heptanoic acid;
(3R,4R,5R)-3-Amino-4,5-dimethyl-octanoic acid;
(3R,4R,5R)-3-Amino-4,5-dimethyl-nonanoic acid;
(3R,4R,5R)-3-Amino-4,5-dimethyl-decanoic acid;
3-Amino-5-cyclopropyl-4-ethyl-hexanoic acid;
3-Amino-6-cyclopropyl-4-ethyl-5-methyl-hexanoic acid;
3-Amino-5-cyclobutyl-4-ethyl-hexanoic acid;
3-Amino-6-cyclobutyl-4-ethyl-5-methyl-hexanoic acid;
3-Amino-5-cyclopentyl-4-methyl-hexanoic acid;
3-Amino-5-cyclopentyl-4-ethyl-hexanoic acid;
3-Amino-6-cyclopentyl-4-ethyl-5-methyl-hexanoic acid;
3-Amino-6-cyclohexyl-4-ethyl-hexanoic acid;
3-Amino-6-cyclohexyl-4-ethyl-5-methyl-hexanoic acid;
3-Amino-5-cyclopropyl-4-methyl-hexanoic acid;
3-Amino-6-cyclopropyl-4,5-dimethyl-hexanoic acid;
3-Amino-5-cyclobutyl-4-methyl-hexanoic acid;
3-Amino-6-cyclobutyl-4,5-dimethyl-hexanoic acid;
3-Amino-5-cyclopentyl-4-methyl-hexanoic acid;
3-Amino-6-cyclopentyl-4,5-dimethyl-hexanoic acid;
3-Amino-5-cyclohexyl-4-methyl-hexanoic acid;
3-Amino-6-cyclohexyl-4,5-dimethyl-hexanoic acid;
3-Amino-8-cyclohexyl-4,5-dimethyl-octanoic acid;
3-Amino-8-cyclohexyl-4,5-dimethyl-octanoic acid;
3-Amino-4,6-dimethyl-heptanoic acid;
3-Amino-4,6-dimethyl-octanoic acid;
3-Amino-4,6-dimethyl-nonanoic acid;
3-Amino-4,6-dimethyl-decanoic acid;
3-Amino-4,6,7-trimethyl-octanoic acid;
3-Amino-4,6,8-trimethyl-nonanoic acid;
3-Amino-4,6,9-trimethyl-decanoic acid;
3-Amino-6-cyclopropyl-4-methyl-heptanoic acid;
3-Amino-6-cyclobutyl-4-methyl-heptanoic acid;
3-Amino-6-cyclopentyl-4-methyl-heptanoic acid;
3-Amino-6-cyclohexyl-4-methyl-heptanoic acid;
3-Amino-7-cyclopropyl-4,6-dimethyl-heptanoic acid;
3-Amino-7-cyclobutyl-4,6-dimethyl-heptanoic acid;
3-Amino-7-cyclopentyl-4,6-dimethyl-heptanoic acid;
3-Amino-7-cyclohexyl-4,6-dimethyl-heptanoic acid;
3-Amino-8-cyclopropyl-4,6-dimethyl-octanoic acid;
3-Amino-8-cyclobutyl-4,6-dimethyl-octanoic acid;
3-Amino-8-cyclopentyl-4,6-dimethyl-octanoic acid;
3-Amino-8-cyclohexyl-4,6-dimethyl-octanoic acid;
3-Amino-6-(3-chloro-phenyl)-4-methyl-heptanoic acid;
3-Amino-6-(3,4-dichloro-phenyl)-4-methyl-heptanoic acid;
3-Amino-4-methyl-6-(3-trifluoromethyl-phenyl)-heptanoic acid;
3-Amino-4-methyl-6-(4-trifluoromethyl-phenyl)-heptanoic acid;
3-Amino-7-(3-chloro-phenyl)-4,6-dimethyl-heptanoic acid;
3-Amino-7-(3,4-dichloro-phenyl)-4,6-dimethyl-heptanoic acid;
3-Amino-4,6-dimethyl-7-(3-trifluoromethyl-phenyl)-heptanoic acid;
3-Amino-4,6-dimethyl-7-(4-trifluoromethyl-phenyl)-heptanoic acid;
3-Amino-8-(3-chloro-phenyl)-4,6-dimethyl-octanoic acid;
3-Amino-8-(3,4-dichloro-phenyl)-4,6-dimethyl-octanoic acid;
3-Amino-4,6-dimethyl-8-(3-trifluoromethyl-phenyl)-octanoic acid;
3-Amino-4,6-dimethyl-8-(4-trifluoromethyl-phenyl)-octanoic acid;
3-Amino-4-ethyl-6-methyl-octanoic acid;
3-Amino-4-ethyl-6-methyl-nonanoic acid;
3-Amino-4-ethyl-6-methyl-decanoic acid;
3-Amino-4-ethyl-6,7-dimethyl-octanoic acid;
3-Amino-4-ethyl-6,8-dimethyl-nonanoic acid;
3-Amino-4-ethyl-6,9-dimethyl-decanoic acid;
3-Amino-6-cyclopropyl-4-ethyl-heptanoic acid;
3-Amino-6-cyclobutyl-4-ethyl-heptanoic acid;
3-Amino-6-cyclopentyl-4-ethyl-heptanoic acid;
3-Amino-6-cyclohexyl-4-ethyl-heptanoic acid;
3-Amino-7-cyclopropyl-4-ethyl-6-methyl-heptanoic acid;
3-Amino-7-cyclobutyl-4-ethyl-6-methyl-heptanoic acid;
3-Amino-7-cyclopentyl-4-ethyl-6-methyl-heptanoic acid;
3-Amino-7-cyclohexyl-4-ethyl-6-methyl-heptanoic acid;
3-Amino-8-cyclopropyl-4-ethyl-6-methyl-octanoic acid;
3-Amino-8-cyclobutyl-4-ethyl-6-methyl-octanoic acid;
3-Amino-8-cyclopentyl-4-ethyl-6-methyl-octanoic acid;
3-Amino-8-cyclohexyl-4-ethyl-6-methyl-octanoic acid;
3-Amino-6-(3-chloro-phenyl)-4-ethyl-heptanoic acid;
3-Amino-6-(3,4-dichloro-phenyl)-4-ethyl-heptanoic acid;
3-Amino-4-ethyl-6-(3-trifluoromethyl-phenyl)-heptanoic acid;
3-Amino-4-ethyl-6-(4-trifluoromethyl-phenyl)-heptanoic acid;
3-Amino-7-(3-chloro-phenyl)-4-ethyl-6-methyl-heptanoic acid;
3-Amino-7-(3,4-dichloro-phenyl)-4-ethyl-6-methyl-heptanoic acid;
3-Amino-4-ethyl-6-methyl-7-(3-trifluoromethyl-phenyl)-heptanoic acid;
3-Amino-4-ethyl-6-methyl-7-(4-trifluoromethyl-phenyl)-heptanoic acid;
3-Amino-8-(3-chloro-phenyl)-4-ethyl-6-methyl-octanoic acid;

3-Amino-8-(3,4-dichloro-phenyl)-4-ethyl-6-methyl-octanoic acid;
3-Amino-4-ethyl-6-methyl-8-(3-trifluoromethyl-phenyl)-octanoic acid; and
3-Amino-4-ethyl-6-methyl-8-(4-trifluoromethyl-phenyl)-octanoic acid.

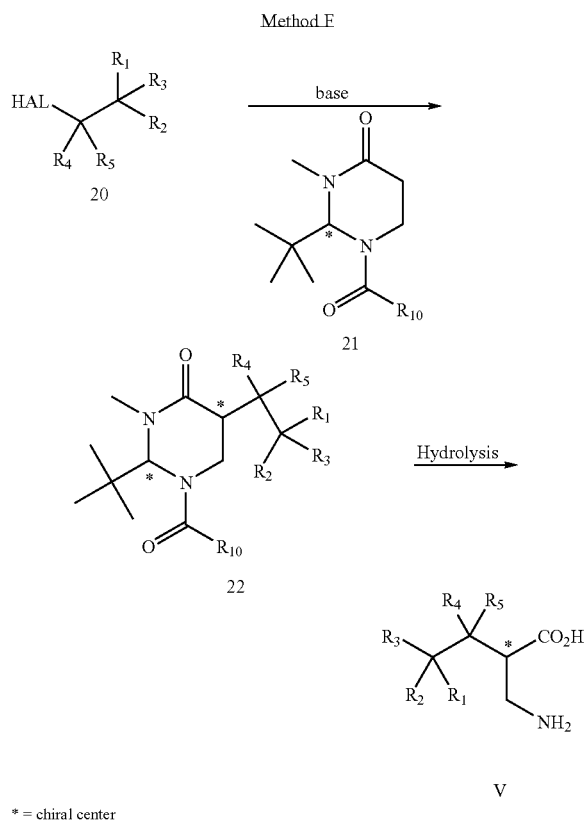

* = chiral center

The synthesis of β-amino acids of formula V via the enantioselective alkylation of enantiopure 1-substituted-2-tert-butyl-3-methylperhydropyrimidine-4-one 21, as illustrated by Method F above, has been described previously. See, e.g., E. Juaristi, et al., *Tetrahedron: Asymmetry* 7:2233 (1996) and references cited therein. Referring to Method F above, compounds of formula 22 can be prepared from corresponding compounds of formula 20 (HAL=Br, I, Cl or another suitable leaving group), wherein $R_{10}$ represents a phenyl or methoxy group, preferably a methoxy group. The hydrolysis can be conducted under acidic conditions in a sealed tube, at reflux, or in a microwave. For instance, the method utilizing 6N HCl in a sealed tube heated at 90-100° C. for 8 hr is described by E. Juaristi et al., *Tetrahedron: Asymmetry* 7:2233 (1996). Other preferred methods include heating a solution of compound 22 in a 1:1 mixture of dioxane:6N HCl in a microwave for 1-3 hrs or at reflux for several days to give a compound of formula V.

Compounds of formula 22 can be prepared from the corresponding compounds of formula 20 by treating them with an appropriate perhydropyrimidine-4-one of formula 21 after deprotonation with an appropriate base such as lithium diisopropylamide or lithium or sodium bis(trimethylsilyl)amide, in a solvent such as ethyl ether, or, preferably, tetrahydrofuran (THF), at a temperature from about 80° C. to about 0° C., and then adding the appropriate compound of formula 20. The stereochemistry of the C5 center arises from approach of the electrophile from the opposite face of the enolate from the sterically congested axial disposition of the tert-butyl group at C2. Preferably, the compound 22 is prepared by the reaction of electrophiles 20 with compounds of formula 21, which have been deprotonated at -78° C. with sodium bis(trimethylsilyl)amide in THF, at -78° C. to -10° C. The synthesis of enantiopure compound 21 ($R_{10}$=Ph) from L-asparagine is described by E. Juaristi et al., *Tetrahedron: Asymmetry* 7:2233 (1996).

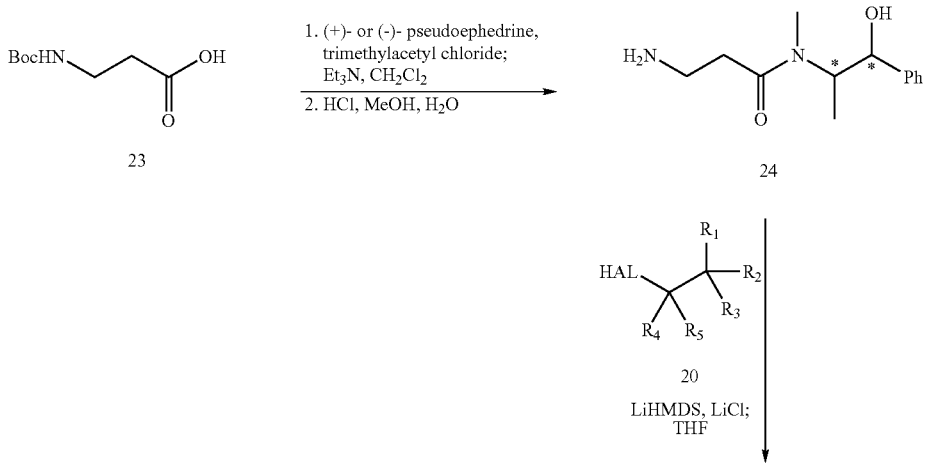

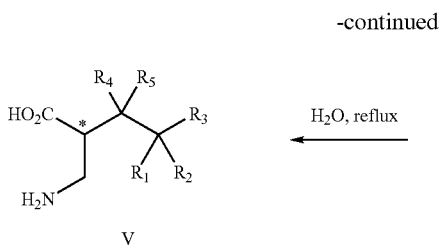 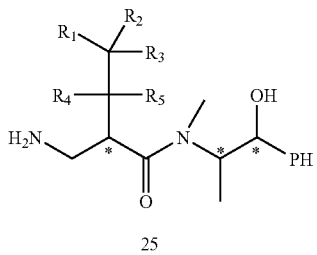

V

* = chiral center

25

In a like manner, Method G shows the synthesis of α-substituted, β-amino acids of formula V via the enantioselective alkylation of enantiopure 3-amino-N-(2-hydroxy-1-methyl-2-phenyl-ethyl)-N-methyl-propionamide (formula 24). See, G. Nagula et al., *Organic Letters* 2:3527-29 (2000). The method includes alkylation of compound 24 using an appropriate alkylating agent 20, where HAL in formula 20 is Br, I, Cl or another suitable leaving group. The enolate alkylation is carried out in a polar aprotic solvent (THF) with excess LiCl at a temperature of about −5° C. to about 0° C. using a hindered base (e.g., lithium hexamethyldisilazide, lithium diisopropylamide, etc.) that is sufficiently strong to deprotonate the α-carbon of formula 24. Hydrolysis of the resulting alkylated amide 25 gives the desired β-amino acid of formula V.

The compound of formula 24 is prepared through N-acylation of a chiral auxiliary, (+)- or (−)-pseudoephedrine, using a mixed anhydride. The mixed anhydride is obtained by reacting an N-terminal protected, 3-amino-propionic acid (e.g., 3-tert-butoxycarbonylamino-propionic acid 23) with trimethylacetyl chloride in the presence of triethylamine in methylene chloride. Following the coupling reaction, the protecting group is removed via known methods (e.g., treatment of the resulting Boc-protected amide with HCl and MeOH) to give the compound of formula 24. See A. Myers et al., *J. Am. Chem. Soc.* 119:656-73 (1997).

Compounds of formula 20 shown in Method F and Method G can be prepared from commercially available materials using methods well known to those of skill in the art. It will be appreciated that compounds of formula 20 may possess one or more stereogenic centers. Using the above-described method, compounds with specific stereochemical configurations can be prepared.

Method H shows a synthesis of β-substituted, β-amino acids of formula IV and their salts, solvates, and hydrates. The method employs a stereoselective hydrogenation of a chiral eneamide (formula 38) to give a chiral amide ester (formula 39), which is subsequently hydrolyzed with a strong acid, such as HCl and other mineral acids, to give a chiral amino acid salt (formula 40). The acid addition salt (formula 40) may be treated with an inorganic or organic base to give the zwitterionic form of formula IV, if desired. Generally, the hydrolysis reaction is carried out in water at reflux conditions, and the resulting salt (formula 40) is recrystallized from a polar solvent, such as MeOH, EtOH, IPA, and the like. In formula 38 through formula 40, $R_3$ is as defined above in connection with formula IV; in formula 38 and formula 39, $R_{13}$ and $R_{15}$ are independently selected from $(C_1-C_6)$alkyl, $(C_3-C_6)$cycloalkyl, and $(C_3-C_6)$cycloalkyl-$(C_1-C_3)$alkyl. As noted in the examples, useful values of $R_{13}$ and $R_{15}$ include, without limitation, ethyl and methyl, respectively.

The hydrogenation is carried out in the presence of a catalyst and one or more polar solvents, such as MeOH, EtOH, IPA, THF, EtOAc, and the like. Useful catalysts include, without limitation, heterogeneous catalysts containing from about 0.1% to about 20%, and more typically, from about 1% to about 5%, by weight, of Pd, Pt, Rh, Ru, Ir, and combinations thereof, which are supported on various materials, including $Al_2O_3$, C, $CaCO_3$, $SrCO_3$, $BaSO_4$, MgO, $SiO_2$, $TiO_2$, $ZrO_2$, and the like. Many of these metals, including Pd, may be doped with an amine, sulfide, or a second metal, such as Pb, Cu, or Zn. Useful catalysts thus include palladium catalysts such as $Pd/SrCO_3$, $Pd/Al_2O_3$, $Pd/MgO$, $Pd/CaCO_3$, $Pd/BaSO_4$, and the like, containing from about 1% to about 5% Pd, based on weight. The reaction may be carried out at a temperature ranging from about 5° C. to about 100° C., though as shown in the examples, good yields (e.g., ≧95%) and high stereoselectivity (e.g., ≧90%) may be obtained for reactions carried out at room temperature. Generally, the substrate-to-catalyst ratio may range from about 1:1 to about 1000:1, based on weight, and $H_2$ pressure may range from about atmospheric pressure, 0 psig, to about 1500 psig. More typically, the substrate-to-catalyst ratios range from about 4:1 to about 20:1, and $H_2$ pressures range from about 25 psig to about 100 psig.

As can be seen in Method H, the chiral eneamide (formula 38) can be prepared from a chiral β-keto ester (formula 33). The β-keto ester (formula 33) may be treated with ammonium acetate in MeOH or EtOH to give a chiral enamine (formula 36), which is subsequently acylated with an acyl. halide (e.g., acid chloride of formula 37), anhydride, etc., to give the chiral eneamide of formula 38. To minimize epimerization of the α-carbon adjacent to the keto moiety, the β-keto ester (formula 33) may be first treated with an alkoxy amine, silyloxy amine, etc. (formula 34) in the presence of an acid catalyst (e.g., HCl), and in the absence of water, to give an oxime (formula 35), which in turn is hydrogenated in the presence of a catalyst, such as Ra—Ni, to give the enamine (formula 36). Typically, the conversion of the β-keto ester (formula 33) to the oxime (formula 35) is carried out at temperatures ranging from about 0° C. to about RT, and the subsequent hydrogenation of the oxime (formula 36) to the enamine (formula 36) is carried out at RT. Substituents $R_3$ and $R_{13}$ in formula 33-36, are as defined above in connection with formula IV and formula 38, respectively. Similarly, $R_{15}$ in formula 37 is as defined above in connection with formula 38. In formula 34, $R_{14}$ is selected from $(C_1-C_6)$alkyl, $(C_3-C_6)$cycloalkyl, $(C_3-C_6)$cycloalkyl-$(C_1-C_3)$alkyl, and silyl.

The β-keto ester (formula 33) may be prepared from a chiral acid (formula 30) using a variety of methods. For example, the chiral acid (formula 30) may be reacted with carbonyl diimidazole (CDI) to give an activated ester (an imidazolide), which is subsequently reacted with an enolate to give the β-keto ester (formula 33). The enolate is prepared by treatment of a malonate derivative (formula 31) with $MgCl_2$, $Mg(OEt)_2$, and so on. Alternatively, the chiral acid (formula 30) may be reacted with chloromethylene dimethyl-ammonium chloride to give an activated acyl chloride, which is subsequently reacted with the enolate, as prepared above, or with an enolate prepared by treating a methyl ester (formula 32) with a hindered base. The hindered base is sufficiently strong to deprotonate the methyl group of formula 32 and includes lithium diisopropylamide (LDA), lithium isopropylcyclohexylamide (LICA), 2,2,6,6-tetramethylpiperidine (LTMP), lithium hexamethyldisilazide (LHMDS), and the like. In formula 30, $R_3$ is as defined above in connection with formula 6, and in formula 31 and formula 32, $R_{13}$ is $(C_1-C_6)$alkyl, $(C_3-C_6)$cycloalkyl, and $(C_3-C_6)$cycloalkyl-$(C_1-C_3)$alkyl. Useful $R_{13}$ substituents thus include ethyl.

As shown in Method H, the chiral acid (formula 30) may be obtained by hydrolysis of a chiral imide (formula 29), which is prepared by the stereoselective conjugate addition of an alkyl(methyl) group to an α,β-unsaturated imide (formula 28). The conjugate addition is carried out by reacting a Grignard reagent (e.g., $CH_3MgX$, where X=Cl, Br, I, $CH_3Li$, etc.) with a suitable Cu(I) salt (e.g., copper bromide dimethylsulfide complex, CuI, etc.) in a compatible solvent, such as THF, diethylether, and the like, in the presence of a lithium salt (LiCl, LiBr, etc.) to form an organocopper reagent. The organocopper reagent is then reacted with the α,β-unsaturated imide of formula 28 to give the chiral imide (formula 29). The conjugate addition may be quenched by treating the reaction mixture with an acid (e.g., acetic acid) at RT or below. The formation of the organocopper reagent and the conjugate addition are typically carried out at temperatures ranging from about −25° C. to about 0° C.

The α,β-unsaturated imide (formula 28) may be prepared from an α,β-unsaturated acid (formula 26) and appropriately substituted oxazolidinone (formula 27) using a coupling agent, 2-ethoxy-1-ethoxycarbonyl-1,2-dihydroquinoline (EEDQ). Generally, the reaction may be carried out at temperatures ranging from about RT to about 100° C., but more typically, the reaction may be carried out at temperatures ranging from about 40° C. to about 75° C. Alternatively, the coupling reaction may be carried out using the methods described above to prepare compound 7. In formula 26 through formula 29, $R_3$ is as defined above in connection with formula IV. In the chiral auxiliary (formula 27), $R_{11}$ and $R_{12}$ are independently hydrogen, $(C_1-C_3)$alkyl, phenyl, and benzyl, provided that $R_{11}$ and $R_{12}$ are not both hydrogen. Useful $R_{11}$ and $R_{12}$ thus include phenyl and hydrogen, respectively.

The enamine (formula 36) may optionally be converted to a corresponding ester (formula 41) of the zwitterionic form (formula IV) via the use of a chiral catalyst. The resulting ester may then be converted to a salt (formula 40) via acid or base hydrolysis, which may be treated with an appropriate acid or base to give the zwitterionic compound (formula IV). Potentially useful chiral catalysts include chiral phosphine (e.g., bisphosphine) or phosphinite ligands bound to transition metals, such as ruthenium, rhodium or iridium. Ru-, Rh- or Ir-phosphine, phosphinite or phospino oxazoline complexes are optically active because they possess a chiral phosphorus atom or a chiral group connected to a phosphorus atom, or because in the case of BINAP and similar atropisomeric ligands, they possess axial chirality. Chiral ligands include, without limitation, BisP*, (R,R)-DIOP, (R,R)-DIPAMP, (R)-(S)-BPPFA, (S,S)-BPPM, (+)-CAMP, (S,S)-CHIRAPHOS, (R)-PROPHOS, (R,R)-NORPHOS, (R)-BINAP, (R)-CYCPHOS, (R,R)-BDPP, (R,R)-DEGUPHOS, (R,R)-Me-DUPHOS, (R,R)-Et-DUPHOS, (R,R)-i-Pr-DUPHOS, (R,R)-Me-BPE, (R,R)-Et-BPE (R)-PNNP, (R)-BICHEP, (R,S,R,S)-Me-PENNPHOS, (S,S)-BICP, (R,R)-Et-FerroTANE, (R,R)-t-butyl-miniPHOS, (R)-Tol-BINAP, (R)-MOP, (R)-QUINAP, CARBOPHOS, (R)-(S)-JOSIPHOS, (R)-PHANEPHOS, BIPHEP, (R)-Cl-MeO-BIPHEP, (R)-MeO-BIPHEP, (R)-MonoPhos, BIFUP, (R)-SpirOP, (+)-TMBTP, (+)-tetraMeBITIANP, (R,R,S,S) TANGPhos, (R)-PPh$_2$-PhOx-Ph, (S,S) MandyPhos and (R)-CnTunaPHOS, where n is an integer of 1 to 6.

Other chiral ligands include, without limitation, (R)-(−)-1-[(S)-2-(di(3,5-bistrifluoromethylphenyl)phosphino)ferrocenyl]ethyidicyclohexyl-phosphine; (R)-(−)-1-[(S)-2-(di(3,5-bis-trifluoromethylphenyl)phosphino)ferrocen-yl]ethyldi(3,5-dimethylphenyl)phosphine; (R)-(−)-1-[(S)-2-(di-t-butylphosphino)-ferro-cenyl]ethyldi(3,5-dimethylphenyl) phosphine; (R)-(−)-1-[(S)-2-(dicyclo-hexylphosphino) ferrocenyl]ethyidi-t-butylphosphine; (R)-(−)-1-[(S)-2-(dicyclo-hexylphosphino)ferrocenyl] ethyldicyclohexylphosphine; (R)-(−)-1-[(S)-2-(dicyclohexylphosphino)ferrocenyl] ethyldiphenylphosphine; (R)-(−)-1-[(S)-2-(di(3,5-dimethyl-4-methoxyphenyl)phosphino)ferrocenyl] ethyidicyclohexylphosphine; (R)-(−)-1-[(S)-2-(diphenylphos-phino)ferrocenyl]ethyidi-t-butylphosphine; (R)-N-[2-(N,N-dimethylamino)ethyl]-N-methyl-1-[(S)-1',2-bis(diphenyl-phosphino)ferrocenyl]ethylamine; and (R)-(+)-2-[2-(diphenylphosphino)-phenyl]-4-(1-methylethyl)-4,5-dihydrooxazole.

Useful ligands may also include stereoisomers (enantiomers and diastereoisomers) of the chiral ligands described in the preceding paragraphs, which may be obtained by inverting all or some of the stereogenic centers of a given ligand or by inverting the stereogenic axis of an atropoisomeric ligand. Thus, for example, useful chiral ligands also include (S)-Cl-MeO-BIPHEP, (S)-PHANEPHOS, (S,S)-Me-DUPHOS, (S,S)-Et-DUPHOS, (S)-BINAP, (S)-Tol-BINAP, (R)-(R)-JOSIPHOS, (S)-(S)-JOSIPHOS, and so on.

Many of the chiral catalysts, catalyst precursors, or chiral ligands may be obtained from commercial sources or may be prepared using known methods. A catalyst precursor or pre-catalyst is a compound or set of compounds, which are converted into the chiral catalyst prior to use. Catalyst precursors typically comprise Ru, Rh or Ir complexed with the phosphine ligand and either a diene (e.g., norboradiene, COD, (2-methylallyl)$_2$, etc.) or a halide (Cl or Br) or a diene and a halide, in the presence of a counterion, X$^−$, such as OTf$^−$, PF$_6^−$, BF$_4^−$, SbF$_6^−$, ClO$_4^−$, etc. Thus, for example, a catalyst precursor comprised of the complex, [(bisphosphine ligand)Rh(COD)]$^+$X$^−$ may be converted to a chiral catalyst by hydrogenating the diene (COD) in MeOH to yield [(bisphosphine ligand)Rh(MeOH)$_2$]$^+$X$^−$. MeOH is subsequently displaced by the enamine (formula 36), which undergoes enantioselective hydrogenation to the desired chiral compound. Example chiral catalysts or catalyst precursors include (+)-TMBTP-ruthenium(II) chloride acetone complex; (S)-Cl-MeO-BIPHEP-ruthenium(II) chloride Et$_3$N complex; (S)-BINAP-ruthenium(II) Br$_2$ complex; (S)-tol-BINAP-ruthenium(II) Br$_2$ complex; and (1,5-cyclooctadiene)[(3R,4R)-3,4-bis(diphenylphosphino)-1-methylpyrrolidine]rhodium tetrafluoroborate.

For a given chiral catalyst and prochiral substrate, the molar ratio of the substrate and catalyst (s/c) may depend on, among other things, H$_2$ pressure, reaction temperature, and solvent. Usually, the substrate-to-catalyst ratio exceeds about 10:1 or 20:1, and substrate-to-catalyst ratios of about 100:1 or 200:1 are common. Although the chiral catalyst may be recycled, higher substrate-to-catalyst ratios are useful. For example, substrate-to-catalyst ratios of about 1000:1, 10,000/1, and 20,000:1, or greater, would be useful. The asymmetric hydrogenation is typically carried out at about RT or above, and under about 0.1 MPa (1 atm) or more of H$_2$. The temperature of the reaction mixture may range from about 20° C. to about 80° C., and the H$_2$ pressure may range from about 0.1 MPa to about 5 Mpa or higher, but more typically, ranges from about 0.3 Mpa to about 3 Mpa. The combination of temperature, H$_2$ pressure, and substrate-to-catalyst ratio is generally selected to provide substantially complete conversion (i.e., about 95 wt %) of the prochiral olefin within about 24 hours. With many of the chiral catalysts, increasing the H$_2$ pressure increases the enantioselectivity.

A variety of organic solvents may be used in the asymmetric hydrogenation, including protic solvents, such as MeOH, EtOH, and IPA. Other useful solvents include aprotic polar solvents, such as THF, MeCl$_2$, and acetone, or aromatic solvents, such as toluene, trifluorotoluene, and chlorobenzene. The enantioselective hydrogenation may employ a single solvent, or may employ a mixture of solvents, such as MeOH and THF.

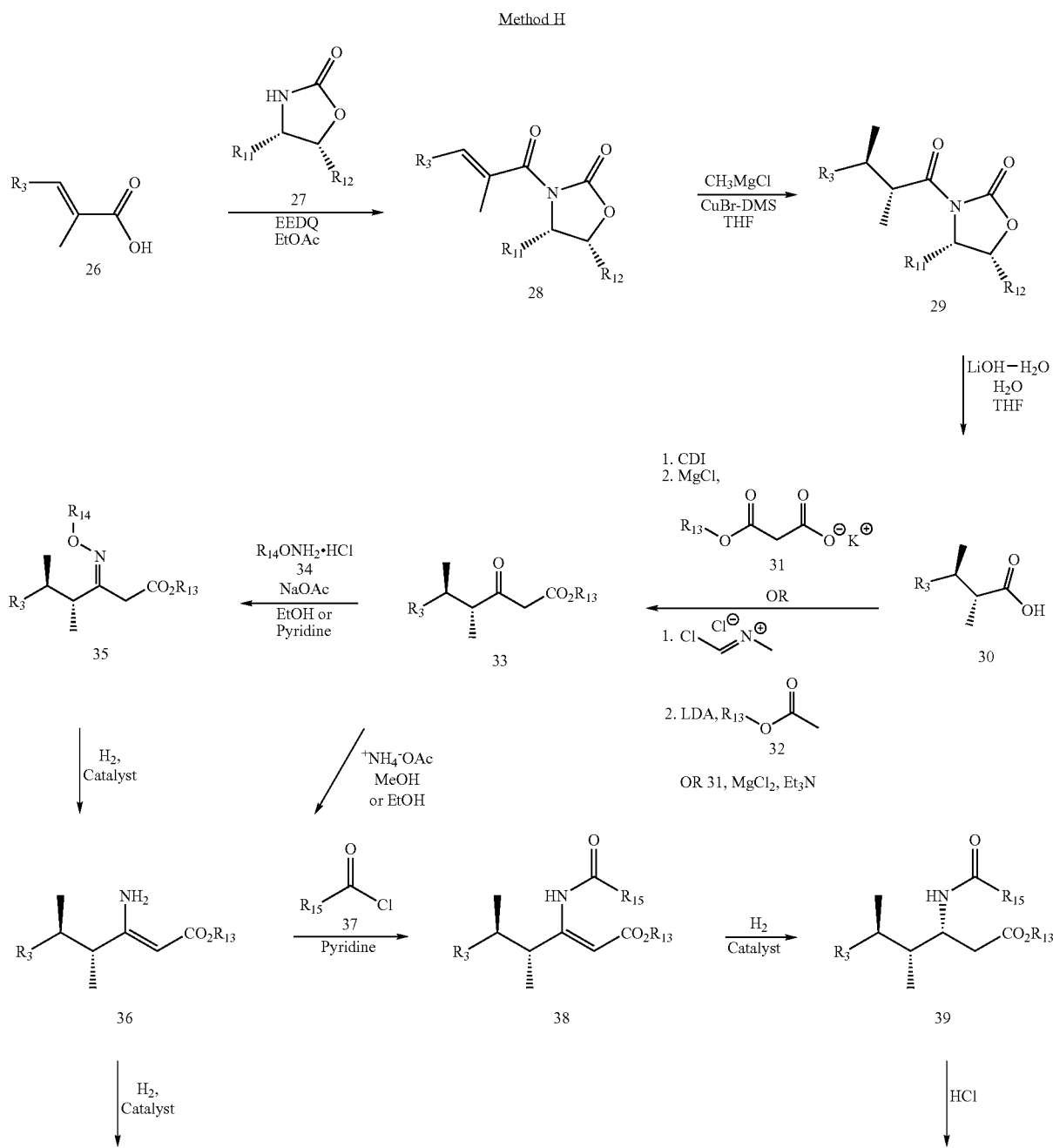

Method H

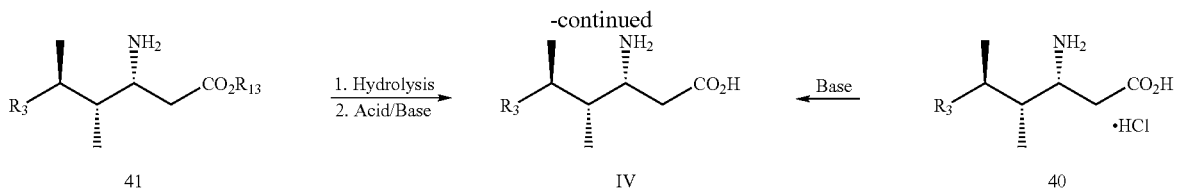

The preparation of compounds of this invention that are not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formula I, II, III, IV, V, and VI, and the intermediates shown in the above reaction schemes can be isolated and purified by conventional procedures, such as recrystallization or chromatographic separation.

The ability of compounds of the present invention to bind to the α2δ-subunit of a calcium channel can be determined using the following binding assay.

The radioligand binding assay using [$^3$H]-gabapentin and the α2δ-subunit derived from porcine brain tissue was used. See Nicolas S. Gee et al., "The novel anticonvulsant drug, gabapentin (Neurontin), binds to the α2δ subunit of a calcium channel," J. Biol. Chem. 271(10):5768-76 (1996). Compounds of the invention bind with nanomolar to micromolar affinity for the α2δ protein. For example, 2-aminomethyl-5-ethyl-nonanoic acid binds with 75 nM affinity to the α2δ protein; (S)-3-amino-5-ethyl-3-methyl-heptanoic acid binds with 149 nM affinity to the α2δ protein; and (3S,5R)-3-amino-3,5-dimethyl-heptanoic acid binds with 236 nM affinity to the α2δ protein.

The in vivo activity of compounds of this invention can be determined in animal models. For animal models related to hyperalgesia, see, e.g., K. Sluka et al., "Unilateral intramuscular injections of acidic saline produce a bilateral, long-lasting hyperalgesia," Muscle Nerve 24:37-46 (2001); W. Dixon, "Efficient analysis of experimental observations," Ann. Rev. Pharmacol. Toxicol. 20:441-62 (1980); L. O. Randall and J. J. Selitto, "A method for measurement of analgesic activity on inflamed tissue," Arch. Int. Pharmacodyn 4:409-19 (1957); K. Hargreaves et al., "A new and sensitive method for measuring thermal nociception in cutaneous hyperalgesia," Pain 32:77-88 (1988). Fir animal models related to anxiety, see J. R. Vogel et al., "A simple and reliable conflict procedure for testing anti-anxiety agents," Psychopharmacologia 21:1-7 (1971).

The compounds of the present invention, and their pharmaceutically acceptable salts, can be administered to mammals via either the oral, parenteral (such as subcutaneous, intravenous, intramuscular, intrasternal and infusion techniques), rectal, buccal or intranasal routes.

The novel compounds of the present invention may be administered alone or in combination with pharmaceutically acceptable carriers or diluents by any of the routes previously indicated, and such administration may be carried out in single or multiple doses. More particularly, the novel therapeutic agents of this invention can be administered in a wide variety of different dosage forms; i.e., they may be combined with various pharmaceutically acceptable inert carriers in the form of tablets, capsules, lozenges, troches, hard candies, suppositories, jellies, gels, pastes, ointments, aqueous suspensions, injectable solutions, elixirs, syrups, and the like. Such carriers include solid diluents or fillers, sterile aqueous media and various non-toxic organic solvents, etc.

Moreover, oral pharmaceutical compositions can be suitably sweetened and/or flavored. In general, the weight ratio of the novel compounds of this invention to the pharmaceutically acceptable carrier will be in the range from about 1:6 to about 2:1, and preferably from about 1:4 to about 1:1.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

For intranasal administration or administration by inhalation, the novel compounds of the invention are conveniently delivered in the form of a solution or suspension from-a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. Formulations of the active compounds of this invention for treatment of the conditions referred to above in the average adult human are preferably arranged so that each metered dose or "puff" of aerosol contains 20 µg to 1000 µg of active compound. The overall daily dose with an aerosol will be within the range 100 µg to 10 mg. Administration may be several times daily, for example 2, 3, 4 or 8 times, giving for example, 1, 2 or 3 doses each time.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of formulas I to VI or a corresponding pharmaceutically acceptable salt of such compound.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material. In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.01 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.1 mg to about 1 g daily. The dosages, however, may be varied depending upon the requirements of the patient, the severity of the condition being treated, and the compound being employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day, if desired.

The following Examples illustrate the preparation of the compounds of the present invention. They are not meant to be limiting in scope. Melting points are uncorrected. NMR data are reported in parts per million and are referenced to the deuterium lock signal from the sample solvent.

EXAMPLE 1

(4S,5R)-4-Methyl-3-pentanoyl-5-phenyl-oxazolidin-2-one

To a 0° C. stirred solution of valeric acid (3.83 mL, 35.2 mmol) and $Et_3N$ (14.7 mL, 106 mmol) in dry THF (175 mL) was added trimethylacetyl chloride (5.29 mL, 42.3 mmol) dropwise. The mixture was stirred at 0° C. for 1 hour and (4S,5R)-(−)-4-methyl-5-phenyl-2-oxazolidinone (7.50 g, 42.3 mmol) was added followed by LiCl (1.79 g, 42.3 mmol). The reaction was warmed to room temperature overnight with good stirring. The mixture was filtered and the filtrate was concentrated under reduced pressure. $Et_2O$ (75 mL) was added to the residue, which was washed with sat. $NaHCO_3$ (3×40 mL), 1N HCl (3×40 mL), and brine (2×40 mL). The organic phase was dried over $MgSO_4$, filtered and concentrated under reduced pressure to give a quantitative yield of crude product.

(4S,5R)-3-((S)-2-Ethyl-pentanoyl)-4-methyl-5-phenyl-oxazolidin-2-one

To a −78° C. stirred solution of the (4S,5R)-4-Methyl-3-pentanoyl-5-phenyl-oxazolidin-2-one (9.20 g, 35.2 mmol) in dry THF (150 mL) was added NaHMDS (42.2 mL, 1.0 M in THF) dropwise. After 1 hour, ethyl trifluoromethanesulfonate (5.93 mL, 45.7 mmol) was added dropwise and the reaction was stirred at −78° C. for an additional 2 hours. The reaction was warmed to −30° C. for 30 minutes and quenched with sat. $NH_4Cl$. The layers were separated and the aqueous layer was extracted with EtOAc (3×40 mL). The organic extracts were combined and washed with brine (2×40 mL). The organic phase was dried over $MgSO_4$, filtered, and concentrated under reduced pressure to yield 8.05 g of crude product.

(S)-2-Ethyl-pentan-1-ol

To a room temperature solution of the (4S,5R)-3-((S)-2-ethyl-pentanoyl)-4-methyl-5-phenyl-oxazolidin-2-one (8.05 g, 27.8 mmol) in THF (200 mL) was added a solution of $NaBH_4$ (4.21 g, 111 mmol) in $H_2O$ (90 mL). The reaction was allowed to stir overnight at room temperature, was quenched with 2N HCl (75 mL) and the layers were separated. The aqueous layer was extracted with EtOAc (4×40 mL), and the organic extracts were combined and washed with brine (2×30 mL). The organic phase was dried over $MgSO_4$, filtered and concentrated under reduced pressure. The residue was triturated with n-hexanes (2×20 mL) to remove the oxazolidinone side product. After filtering off the oxazolidinone, the filtrate was concentrated under reduced pressure to yield 2.56 g of crude product.

Methanesulfonic acid (S)-2-ethyl-pentyl ester

To a −10° C. stirred solution of (S)-2-ethyl-pentan-1-ol (1.30 g, 11.2 mmol) in dry $CH_2Cl_2$ (35 mL) was added $Et_3N$ (2.33 mL, 16.8 mmol). The reaction was stirred at this temperature for 15 minutes and methansulfonyl chloride (0.952 mL, 12.3 mmol) was added. The reaction was allowed to warm to room temperature overnight with good stirring. The reaction was washed with 1N HCl (3×30 mL), sat. $NaHCO_3$ (3×30 mL), and brine (2×30 mL). The organic phase was dried over $MgSO_4$, filtered and concentrated under reduced pressure to give a quantitative yield of crude product.

(S)-3-Iodomethyl-hexane

To a stirred solution of methanesulfonic acid (S)-2-ethyl-pentyl ester (2.18 g, 11.2 mmol) in acetone (35 mL) was added NaI (3.36 g, 22.4 mmol) and the reaction was heated to reflux overnight with good stirring. The reaction was allowed to cool to room temperature and the mixture was filtered. The salts were washed with acetone (3×15 mL) and $H_2O$ (60 mL) was added to the filtrate. The aqueous phase was extracted with hexanes (4×30 mL) and the organic extracts were combined and washed with brine (2×30 mL). The organic phase was dried over $MgSO_4$, filtered and concentrated under reduced pressure. The residue was purified by chromatography using hexanes (100%) to yield 1.24 g (49%) of pure product.

(2S,5R)-2-tert-Butyl-5-((S)-2-ethyl-pentyl)-3-methyl-4-oxo-tetrahydro-pyrimidine-1-carboxylic acid methyl ester To a −78° C. stirred solution of (S)-2-tert-butyl-3-methyl-4-oxo-tetrahydro-pyrimidine-1-carboxylic acid methyl ester (1.04 g, 4.57 mmol) in dry THF (15 mL) was added NaHMDS (5.03 mL, 1.0 M in THF) dropwise. The reaction was stirred at −78° C. for 1 hour and then a solution of (S)-3-Iodomethyl-hexane (1.24 g, 5.48 mmol) in dry THF (5 mL) was added dropwise. The reaction was stirred at this temperature for 2 hours and than was placed in a −10° C. refrigerator overnight. The reaction was quenched with sat. $NH_4Cl$ (20 mL) and was allowed to warm to room temperature. The layers were separated and the aqueous layer was extracted with EtOAc (3×15 mL). The organic extracts were combined and washed with brine (2×15 mL). The organic phase was dried over $MgSO_4$, filtered and concentrated under reduced pressure. The product was purified by chromatography using hexanes/EtOAc (10→20%) to yield 0.185 g (12%) of pure product: $^1$H NMR (400 MHz, $CD_3OD$) δ ppm 0.9 (m, 6H), 1.3 (m, 5H), 1.4 (m, 3H), 1.7 (m, 1H), 2.5 (m, 1H), 2.9 (d, J=6.6 Hz, 2H). MS: M+1 (328).

(2R,4S)-2-Aminomethyl-4-ethyl-heptanoic acid

A stirred solution of (2S,5R)-2-tert-Butyl-5-((S)-2-ethyl-pentyl)-3-methyl-4-oxo-tetrahydro-pyrimidine-1-carboxylic acid methyl ester (0.185 g, 0.567 mmol) in a 1:1 mixture of 6N HCl/dioxane (8 mL) was heated at 105° C. for 6 days. The reaction was cooled to room temperature and concentrated under reduced pressure. The product was dissolved in 1:1 $MeOH/H_2O$ and loaded onto an ion exchange chromatography column (Varian SCX-Prepacked 10 g, 60 mL) and eluted with 1:1 $MeOH/H_2O$ (95%)+$NH_4OH$. The fractions containing product were collected and concentrated under reduced pressure to yield 0.06 g (57%) of product: $^1$H NMR (400 MHz, $CD_3OD$) δ ppm 0.9 (m, 6H), 1.3 (m, 5H), 1.4 (m, 3H) 1.7 (m, 1H), 2.5 (m, 1H), 2.9 (d, J=6.6 Hz, 2H). MS: M+1 (188).

Using the above methodology the following compounds were also made:

| Compound Name | MS, APCl+ | $^1$H NMR, 400MHz, δ, PPM, $CD_3OD$ |
|---|---|---|
| (4R)-2-Aminomethyl-4-ethyl-heptanoic acid | 188(M+1) | 0.9(s, 6H), 1.3(m, 5H), 1.4(m, 3H), 1.7(s, 1H), 2.5(m, 1H), 2.9(d, J=6.1Hz, 2H) |
| (2R,4S)-2-Aminomethyl-4-7-dimethyl-octanoic acid | 202(M+1) | 0.9(d, J=6.6Hz, 6H), 0.9(d, J=6.6Hz, 3H), 1.2(m, 4H), 1.2(m, 1H), 1.4(m, 1H), 1.5(m, 2H), 1.7(m, 1H), 2.5(m, 1H), 2.9(d, 2H) |
| (2S,4S)-2-Aminomethyl-4-ethyl-8- | 230(M+1) | 2.93(d, 2H), 2.47(5-line m, 1H), 1.72(m, 1H), 1.54(7-line m, |

| Compound Name | MS, APCl+ | 1H NMR, 400MHz, δ, PPM, CD3OD |
|---|---|---|
| methylnonanoic acid | | 1H), 1.42-1.11(m, 10H), 0.85(d, 3H) |
| (2R/S,4S)-2-Aminomethyl-8-methyl-4-propyl-nonanoic acid | 257(M+1) | 2.93(d, 2H), 2.44(5-line m, 1H), 1.72(m, 1H), 1.55(7-line m, 1H), 1.44(m, 1H), 1.40-1.10(m, 11H), 0.89(d, 3H) |
| (2S,4S)-2-Aminomethyl-4-ethyl-6-methyl-heptanoic acid. | 202(M+1) | 2.93(d, 2H), 2.43(m, 1H), 1.71(m, 1H), 1.63(m, 1H), 1.42(m, 1H), 1.36(m, 2H), 1.22(m, 1H), 1.06(m, 2H), 0.85(m, 9H) |
| (2R,4S)-2-Aminomethyl-4-ethyl-6-methyl-heptanoic acid | 202(M+1) | 2.89(d, 2H), 2.43(m, 1H), 1.62(m, 2H), 1.44(m, 1H), 1.34(m, 1H), 1.22(m, 2H), 1.12(m, 1H), 1.05(m, 1H), 0.80(m, 9H) |
| (2R,4R)-2-Aminomethyl-4-ethyl-6-methyl-heptanoic acid | 202.1(M+1) | 2.90(d, 2H), 2.43(m, 1H), 1.68(m, 1H), 1.61(m, 1H), 1.42(m, 1H), 1.32(m, 2H), 1.21(m, 1H), 1.11(m, 2H), 0.80(m, 9H) |
| (2S,4R)-2-Aminomethyl-4-ethyl-6-methyl-heptanoic acid | 202(M+1) | 2.94(d, 2H), 2.23(m, 1H), 1.62(m, 2H), 1.44(m, 1H), 1.42(m, 1H), 1.22(m, 2H), 1.13(m, 1H), 1.03(m, 1H), 0.85(m, 9H) |

EXAMPLE 2

(R)-3-((R)-3-Methyl-hexanoyl)-4-phenyl-oxazolidin-2-one

To the copper (1) bromide dimethylsulfide complex (13.34 g, 64.87 mmol) in dry THF (150 mL) at −30° C. under Nitrogen was added a 2M ether solution of Propyl-magnesiumchloride (64.87 mL, 129.7 mmol) and stirred for 20 minutes. (R)-3-But-2-enoyl-4-phenyl-oxazolidin-2-one (15.0 g, 64.87 mmol) in THF (60 mL) was added over a 15 minute period at −35° C. and let slowly warm up to room temperature over 4 hours. The mixture was cooled to 0° C. and quenched with saturated ammonium chloride solution. The suspension was extracted into ether, washed with 5% ammonium hydroxide solution and then with brine and dried over MgSO4. The solution was concentrated under reduced pressure to afford the titled compound (13.34 g; 100% yield) as a white solid: 1H NMR (400 MHz, CDCl3) δ ppm 0.8 (m, 6H) 1.2 (m, 3H) 1.6 (s, 1H) 2.0 (m, 1H) 2.7 (dd, J=16.1, 8.5 Hz, 1H) 3.0 (dd, J=15.9, 5.4 Hz, 1H) 4.3 (dd, J=8.9, 3.8 Hz, 1H) 4.7 (t, J=8.9 Hz, 1H) 5.4 (dd, J=8.8, 3.9 Hz, 1H) 5.4 (dd, J=8.8, 3.9 Hz, 1H) 7.3 (m, 5H). MS, m/z (relative intensity): 276 [M+1H, 100%].

(R)-3-((2R,3R)-2,3-Dimethyl-hexanoyl)-4-phenyl-oxazolidin-2-one

To a 1M THF solution of Sodium hexamethyldisylamide (16.2 g, 88.3 mmol) at −78° C. was added via canular a 0° C. solution of (R)-3-((R)-3-methyl-hexanoyl)-4-phenyl-oxazolidin-2-one (18.7 g, 67.9 mmol) in 70 mL dry THF. The resulting solution was stirred at −78° C. for 30 minutes. Methyl Iodide (48.2 g, 339.5 mmol) was added and stirring at −78° C. was continued for 4 hours. The reaction was quenched with saturated ammonium chloride solution, extracted into CH2Cl2 and washed with 1M sodium Bisulfite. The solution was dried over MgSO4, concentrated and chromatographed in 10% ethylacetate in hexane to give the titled compound (11.1 g, 56.5% yield) as an oil. MS, m/z (relative intensity): 1H NMR (400 MHz, CDCl3) δ ppm 0.8 (t, J=7.0 Hz, 3H) 0.9 (d, J=6.6 Hz, 3H) 1.0 (d, J=6.8 Hz, 3H) 1.0 (d, J=8.5 Hz, 1H) 1.1 (m, 1H) 1.4 (m, 1H) 1.7 (m, 1H) 3.7 (m, 1H) 4.2 (dd, J=8.8, 3.4 Hz, 1H) 4.6 (t, J=8.7 Hz, 1H) 5.4 (dd, J=8.7, 3.3 Hz, 1H) 7.2 (m, 2H) 7.3 (m, 3H). MS, m/z (relative intensity):290 [M+1H, 100%].

(2R,3R)-2,3-Dimethyl-hexan-1-ol

A 1M THF solution of LAH (95.9 mL, 95.9 mmol) was added to (R)-3-((2R,3R)-2,3-dimethyl-hexanoyl)-4-phenyl-oxazolidin-2-one in THF (300 mL) under nitrogen at −78° C. and stirred for 3 hours at that temperature. Water was added dropwise to quench the excess LAH and the solution was poured into a mixture of ice and ether. The mixture was extracted into ether, washed with water and dried over MgSO4. The solution was concentrated followed by the addition of excess hexane. The resulting white precipitate was filtered and washed with haxane. The filtrate was concentrated to afford the titled compound (5.05 g, 100% yield) as an oil: 1H NMR (400 MHz, CDCl3) δ ppm 0.9 (m, 9H) 1.0 (d, J=6.8 Hz, 1H) 1.1 (m, 1H) 1.2 (m, 3H) 1.6 (m, 2H) 3.4 (m, 1H) 3.6 (m, 1H).

(2R,3R)-2,3-Dimethyl-hexanal

Pyridinium chlorochromate (27.35 g, 126.9 mmol) and neutral alumina (96 g, 3.5 g per gram of pyridinium chlorochromate) in dry dichloromethane (200 mL) was stirred under nitrogen for 0.25 hours. (2R,3R)-2,3-Dimethyl-hexan-1-ol (5.0 g, 38.46 mmol) in dichloromethane (60 mL) was added and the resulting dark slurry was stirred at room temperature for 3 hours. The slurry was filtered through a short pad of silica eluting with excess dichloromethane. Evaporation of the solvent afforded the titled compound (4.1 g, 84% yield) as an oil: 1H NMR (400 MHz, CDCl3) δ ppm 0.8 (m, 3H) 0.9 (d, J=6.6 Hz, 3H) 1.0 (d, J=6.6 Hz, 3H) 1.2 (m, 4H) 1.8 (m, 1H) 2.2 (m, 1H) 9.6 (s, 1H).

4-Methyl-benzenesulfinic acid ((2R,3R)-2,3-dimethyl-hexylidene)-amide

Titanium(IV) ethoxide (5.16 g, 22.6 mmol) and (S)-(+)-p-toluenesulfinamide (7.02 g, 45.2 mmol) were added to (2R,3R)-2,3-dimethyl-hexanal (2.9 g, 22.6 mmol) in dry THF (30 mL). The resulting mixture was stirred at room temperature for 18 hours and poured into a brine solution (40 mL). The slurry was rapidly stirred for 10 minutes and filtered. The filtrate was extracted into ethyl acetate, washed with brine and dried over MgSO₄. The solvent was evaporated and the residue was filtered through a silica plug, eluting with 50/50 solution of hexane/ethyl acetate to afford the titled compound (3.1 g, 51.6% yield) as an oil: ¹H NMR (400 MHz, CDCl₃) δ ppm 0.8 (m, 6H) 1.1 (m, 4H) 1.3 (m, 3H) 1.7 (m, 1H) 2.4 (s, 3H) 2.5 (m, 1H) 7.3 (d, J=8.3 Hz, 2H) 7.5 (d, J=8.1 Hz, 2H) 8.1 (d, J=5.4 Hz, 1H). MS, m/z (relative intensity): 266 [M+1H, 100%].

(4R,5R)-4,5-Dimethyl-(R)-3-(toluene-4-sulfiny-lamino)-octanoic acid tert-butyl ester Butyl lithium (26.3 mL, 42.04 mmol) was added to a solution of diisopropylamine (4.6 g, 45.6 mmol) in dry THF (40 mL) under nitrogen at 0° C. and stirred for 20 minutes. The solution was cooled to −78° C. followed by the addition of t-butyl acetate (4.1 g, 35.0 mmol) and stirred at that temperature for 45 minutes. Chlorotitanium triisopropoxide (9.4 g, 36.2 mmol) was added dropwise and stirring was continued for 30 minutes at −78° C. A −50° C. solution of 4-methyl-benzenesulfinic acid ((2R,3R)-2,3-dimethyl-hexylidene)-amide (3.1 g, 11.7 mmol) in dry THF (10 mL) was added to the reaction and the resulting mixture was stirred at −78° C. for 4 hours. The reaction was quenched with a saturated solution of NaH₂PO₄ and extracted into ethyl acetate. The solution was dried over MgSO₄ and concentrated. The resulting residue was chromatographed on silica, eluting with 15% ethyl acetate in hexane to give the titled compound (2.4 g, 53.9% yield) as white solid: 1H NMR (400 MHz, CDCl₃) δ ppm 0.9 (m, 6H) 1.0 (d, J=6.6 Hz, 3H) 1.1 (m, 1H) 1.3 (m, 2H) 1.4 (m, 9H) 1.5 (m, 2H) 2.4 (s, 3H) 2.6 (m, 2H) 3.8 (m, 1H) 4.4 (d, J=10.0 Hz, 1H) 7.3 (d, J=8.1 Hz, 2H) 7.6 (d, J=8.1 Hz, 2H). MS, m/z (relative intensity): 382 [M+1H, 100%], 326 [M+1H—C(CH₃)₃, 50%].

(3R,4R,5R)-3-Amino-4,5-dimethyl-octanoic acid

To the solution of (4R,5R)-4,5-dimethyl-(R)-3-(toluene-4-sulfinylamino)-octanoic acid tert-butyl ester (1.8 g, 4.71 mmol) in dry methanol (30 mL) at 0° C. under nitrogen was added excess trifluoroacetic acid (25 mL) and stirred for 2 hours at that temperature. The solution was concentrated to dryness followed by the addition of dry dichloromethane (20 mL) and trifluoroacetic acid (20 mL). The resulting mixture was stirred for 2 hours under nitrogen and concentrated to dryness. The residue was applied to BondElute SCX ion exchange resin and eluted with water until the eluent was at constant pH of 6.5. The resin was then eluted with a 1:1 solution of methanol and with 10% ammonium hydroxide solution. The ammonium hydroxide solution was evaporated and the residue was crystallized with methanol-acetonitrile mixture to afford the titled compound (0.717 g, 81.2% yield) as a white solid: ¹H NMR (400 MHz, CD3OD-D) δ ppm 0.9 (m, 11H) 1.1 (m, 2H) 1.3 (m, 1H) 1.4 (m, 1H) 1.6 (m, 1H) 1.7 (m, 2H) 2.3 (dd, J=16.6, 10.0 Hz, 1H) 2.5 (dd, J=16.7, 3.5 Hz, 1H) 3.3 (m, 1H). MS, m/z (relative intensity): 188 [M+1H, 100%], 186 [M−1H, 100%].

EXAMPLE 3

(S)-4-Methyl-hexan-2-one (2)

The Grignard reagent made from (S)-1-bromo-2-methylbutane (10 g, 66.2 mmol) and Mg (1.77 g, 72.8 mmol) in Et₂O (65 mL) was added dropwise to a solution of acetic anhydride (8.1 g, 79.3 mmol) in Et₂O (65 mL) at −78° C. in 1 hour. Lots of white solid precipitated. The reaction mixture was stirred at −78° C. for 1 hour. Then the temperature was allowed to slowly rise to RT. The reaction was quenched with saturated NH₄Cl aqueous solution (150 mL). The ether phase was washed by 1 N NaOH (150 mL) and brine (150 mL). The ether phase was stripped under reduce pressure at 0° C. The residual oil was dissolved in hexane (50 mL). The solution was dried by anhydrous Na₂SO4 and evaporated at 0° C. under reduced pressure to give (S)-4-methyl-hexan-2-one (5.7 g, 75% yield) as a light orange oil: ¹H NMR (CDCl₃) δ 2.26 (m, 2H), 2.08 (s, 3H), 1.86 (m, 1H), 1.21 (m, 2H), 0.83 (m, 6H); MS (APCI) (M+1)⁺ 115.0.

(S)-2-Methyl-propane-2-sulfinic acid ((3S)-1,3-dimethyl-pentylidene)-amide

A mixture of (S)-4-methyl-hexan-2-one (1.6 g, 14 mmol), (S)-2-methyl-propane-2-sulfinic acid amide (1.7 g, 14 mmol) and titanium(IV) ethoxide (6.4 g, 28 mmol) in THF (30 mL) was refluxed for 10 hours. Then the reaction mixture was poured into brine (150 mL). The mixture was filtered. The filtrate was extracted by EtOAc (3×70 mL). The EtOAc phase was removed under reduce pressure and the residue was purified by a silica gel column (Hexane/EtOAc 3:1) to give the titled compound (1.93 g, 63% yield) as a colorless oil: ¹H NMR (CDCl₃) δ 2.24 (m, 2H), 2.27 (s, 3H), 1.85 (m, 1H), 1.22 (m, 2H), 1.20 (s, 9H), 0.85 (m, 6H); MS (APCI) (M+1)⁺ 218.1.

(3S,5S)-3,5-Dimethyl-3-((S)-2-methyl-propane-2-sulfinylamino)-heptanoic acid methyl ester To a solution of diisopropylamine (3.1 mL, 22.2 mmol) in THF (40 mL) at −78° C. was slowly added butyllithium (14.4 mL, 1.6 M, 23 mmol). The mixture was stirred at 0° C. for 25 minutes and subsequently cooled down to −78° C. Methyl acetate (1.76 mL, 22.2 mmol) in THF (7 mL) was added. After Stirring for 20 minutes, chlorotitaniumtriisopropoxide (11 mL, 46.2 mmol) in THF (10 mL) was added and the resulting mixture was stirred at −78° C. for 20 minutes. (S)-2-Methyl-propane-2-sulfinic acid ((3S)-1,3-dimethyl-pentylidene)-amide (1.9 g, 8.9 mmol) in THF (10 mL) was added. The mixture was stirred at −78° C. overnight. The reaction was quenched by NH₄Cl solution (50 mL). The mixture was filtered. The filtrate was extracted by EtOAc (3×70 mL). The EtOAc phase was reduced under reduce pressure and the residue was purified by a silica gel column (Hexane/EtOAc 1:1) to give the titled compound (1.61 g, 62% yield) as a colorless oil: ¹H NMR (CDCl₃) δ 3.64 (s, 3H), 2.60 (m, 2H), 1.47 (m, 2H), 1.44 (m, 1H), 1.36 (s, 3H), 1.27 (m, 2H), 1.19 (s, 9H), 0.90 (d, J=6.4 Hz, 3H), 0.81 (t, J=7.6 Hz, 3H); MS (APCI) (M+1)⁺ 292.2.

(3S,5S)-3-Amino-3,5-dimethyl-heptanoic acid

A mixture of (3S,5S)-3,5-dimethyl-3-((S)-2-methyl-propane-2-sulfinylamino)-heptanoic acid methyl ester (0.4 g, 1.37 mmol) and concentrated hydrochloric acid (7.6 mL) in acetone (10 mL) was refluxed for 3 hours. The solvents were stripped under reduced pressure. The residue was dissolved in water (10 mL) and extracted by EtOAc (2×15 mL). The aqueous phase was evaporated to dryness. The residue was dissolved in a mixture of water (10 mL) and triethylamine (0.5 mL). The mixture was stirred at 40° C. for 20 minutes and then was evaporated to dryness. The residue was washed thoroughly with acetonitrile, filtered, and dried under vacuum to give the final product, (3S,5S)-3-amino-3,5- dimethyl-heptanoic acid (0.182 g, 77% yield) as a white solid. m.p. 215-217° C.: $^1$H NMR (CDCl$_3$) δ 4.85 (s, 3H), 2.38 (m, 2H), 1.75 (m, 1H), 1.39 (m, 4H), 1.35 (s, 3H), 0.98 (d, J=6.6 Hz, 3H), 0.90 (t, J=7.5 Hz, 3H); MS (APCI) (M+1)$^+$ 174.1.

Using the above methodology the following compounds were also made.

| Compound Name | MS, APCl$^+$ | $^1$H NMR, 400MHz, δ, PPM, CD$_3$OD |
|---|---|---|
| (3R,5S)-3-Amino-3,5-dimethyl-heptanoic acid | 174(M+1) | 4.84(s, 3H), 2.38(m, 2H), 1.58(m, 1H), 1.37(m, 4H), 1.34(s, 3H), 0.98(d, J=6.3Hz, 3H), 0.91(t, J=7.4Hz, 3H) |
| (3S,5R)-3-Amino-3,5-dimethyl-heptanoic acid | 174(M+1) | 4.84(s, 3H), 2.38(m, 2H), 1.58(m, 1H), 1.37(m, 4H), 1.34(s, 3H), 0.98(d, J=6.3Hz, 3H), 0.91(t, J=7.4Hz, 3H) |
| (3R)-3-Amino-3,5-dimethyl-octanoic acid | 188(M+1) | 4.84(s, 3H), 2.39(m, 2H) 1.72(m, 1H) 1.59(s, 3H) 1.38(m, 6H) 0.98(d, J=6.1Hz, 3H), 0.91(m, 3H) |
| (3R, 4R/S)-3-Amino-4-methyl-heptanoic acid | 160(M+1) | 0.98(m, 6H) 1.20(m, 1H) 1.32(m, 1H) 1.43(m, 2H) 1.78(m, 1H), 2.32(m, 1H) 2.47(m, 1H) 3.30(m, 1H) |
| (3S,6R)-3-Amino-8-cyclohexyl-6-methyl-octanoic acid | 256(M+1) | 0.87(m, 2H) 0.88(dd, J=15.86, 6.10Hz, 3H) 1.20(m, 11H) 1.39(m, 4H) 1.69(m, 6H) 2.53(dd, J=17.32, 8.05Hz, 1H) 2.69(m, 1H) 3.44(ddd, J=14.70, 6.89, 4.76Hz, 1H) |

EXAMPLE 4

(3R)-(3,7-Dimethyl-oct-6-enyl)-cyclohexane

A flask was charged with 100 mL of dry THF and cooled to 0° C. To this flask was added 103 mL (205 mmol) of 2 M cyclohexylmagnesium chloride in diethylether. Then 2.30 g (17 mmol) copper(II) chloride was taken up in 60 mL of THF and added as a slurry to the Grignard reagent. To this mixture was added 0.73 g (17.1 mmol) lithium chloride, and the mixture was stirred at 0° C. for 30 minutes. Then 13.5 mL (68.4 mmol) of (S)-citronellyl bromide was added, and the mixture was stirred 2 hours at 0° C. The reaction mixture was allowed to warm to room temperature and stirred overnight. The reaction was quenched by the addition of sat. aq. NH$_4$Cl until bubbling ceased. The THF was removed under reduced pressure. The residue was taken up in water and extracted with diethyl ether. The combined ether layers were dried over MgSO$_4$. The drying agent was removed by filtration. The solvent was removed under reduced pressure to yield 11.48 g (76% yield) of a clear oil. The crude long-chain alkyl was not readily characterized, and was carried on without further purification.

3-((R)-5-Cyclohexyl-3-methyl-pentyl)-2,2-dimethyl-oxirane

A flask was charged with 11.48 g (51.6 mmol) of crude (3R)-(3,7-dimethyl-oct-6-enyl)-cyclohexane, 100 mL of dichloromethane, and 9.33 g (111 mmol) of sodium bicarbonate. The mixture was cooled in a 0° C. bath. Slowly 11.6 mL (55.2 mmol) 32% peracetic acid was added. The mixture was stirred for 4 hours at 0° C. Then 10% aqueous sodium sulfite was added slowly until bubbling ceased. The layers were separated, and the organic layer was washed twice with 10% aqueous sodium sulfite and dried over magnesium sulfate. The drying agent was removed by filtration, and the solvent was removed under reduced pressure. The remaining residue was 10.65 g (87%) of a clear oil: $^1$H NMR (400 MHz, CDCl$_3$) ppm 0.86 (m, 5H) 1.00 (d, J=6.59 Hz, 2H) 1.14 (m, 7H) 1.25 (s, 3H) 1.29 (s, 3H) 1.35 (m, 2H) 1.50 (m, 3H) 1.65 (m, 5H) 2.68 (td, J=6.16, 1.83 Hz, 1H). MS (APCI) m+1/z=239.

(R)-6-Cyclohexyl-4-methyl-hexanal

A flask was charged with 10.65 g (44.7 mmol) of 3-((R)-5-cyclohexyl-3-methyl-pentyl)-2,2-dimethyl-oxirane, 70 mL of acetone, 12.3 g (53.6 mmol) of potassium periodate, 70 mL of water, and 0.765 g (4 mmol) of tosic acid-monohydrate. The mixture was stirred for 46 hours. The acetone was removed under reduced pressure, and the mixture was diluted with water. The aqueous layer was extracted with hexanes and dried with sodium sulfate. The drying agent was filtered off and solvent was removed under reduced pressure to get 7.12 g (81% yield) of a clear oil: $^1$H NMR (400 MHz, CDCl$_3$) ppm 0.87 (m, 5H) 1.13 (m, 3H) 1.25 (m, 5H) 1.66 (m, 8H) 2.40 (m, 2H) 9.75 (s, 1H). MS (APCI) m+1/z is inconclusive.

(R)-6-Cyclohexyl-4-methyl-hexanoic acid

A flask was charged with 7.12 g (36.3 mmol) of (R)-6-cyclohexyl-4-methyl-hexanal, 40 mL of water, 20 mL of acetone, 4 mL acetic acid, and 6.18 g (39.9 mmol) of potassium permanganate. The mixture was stirred vigorously overnight. The mixture was then treated with sat. aqueous sodium bisulfite until the liquid became clear. The liquid was extracted with hexanes. The combined hexane layers were washed with sat. aqueous sodium bisulfite until the hexane layer was clear. The hexane phases were dried with magnesium sulfate. The drying agent was filtered off and the solvent was removed under reduced pressure, which yielded 4.17 g (54% yield) of a clear oil: $^1$H NMR (400 MHz, CDCl$_3$) ppm 0.89 (m, 5H), 1.13 (m, 3H) 1.25 (m, 5H) 1.66 (m, 8H) 2.40 (m, 2H). MS (APCI) m+1/z=211.

(4R,5S)-3-((R)-6-Cyclohexyl-4-methyl-hexanoyl)-4-methyl-5-phenyl-oxazolidin-2-one A flask was charged with 4.17 g (19.6 mmol) of (R)-6-cyclohexyl-4-methyl-hexanoic acid, 40 mL of THF, and 8.56 mL (61.4 mmol) of triethylamine. The mixture was cooled in a 0° C. bath, and 2.41 mL (19.6 mmol) of pivaloyl chloride was added. The mixture was stirred for 1 h at 0° C. Then 2.79 g (16.4 mmol) of (4R,5S)-4-methyl-5-phenyl-2-oxazolidinone and 0.823 g (19.6 mmol) of lithium chloride were added as solids. The mixture was allowed to warm to room temperature and stirred overnight. The resulting solids were filtered off. The solvent was stripped under reduce pressure, and the residue was purified by column chromatography (eluent: 4:1 hexanes/ethyl acetate) to give 6.09 g (quant.) of a clear oil: $^1$H NMR (400 MHz, CDCl$_3$) δ ppm 0.89 (m, 8H) 1.16 (m, 6H) 1.68 (m, 9H) 2.87 (m, 1H) 2.99 (m, 1H) 4.76 (qd, J=6.83, 6.59 Hz, 1H) 5.66 (d, J=7.32 Hz, 1H) 7.30 (m, 2H) 7.40 (m, 3H). MS (APCI) m+1/z=372.

(5R,3S)-7-Cyclohexyl-5-methyl-3-((4R,5R)-4-methyl-2-oxo-5-phenyl-oxazolidine-3-carbonyl)-heptanoic acid tert-butyl ester A dry flask was charged with 60 mL of THF, 2.87 mL (20.5 mmol) of diisopropyl amine, and the resulting solution was cooled in a −78° C. bath. To this solution was added 13.3 mL (19.7 mmol) of 1.48 M n-butyl lithium solution. The mixture was allowed to warm to 0° C. and was stirred for 30 minutes at this temperature. The LDA solution was cooled again to −78° C., and 6.10 g (16.4 mmol) of (4R,5S)-3-((R)-6-cyclohexyl-4-methyl-hexanoyl)-4-methyl-5-phenyl-oxazolidin-2-one was added dropwise as a solution in 35 mL of THF. The mixture was stirred for 45 minutes at −78° C., and was then allowed to warm slowly to −20° C. over 2.5 hours. The reaction mixture was quenched by the addition of sat. aq. ammonium chloride. The solvent was removed under reduced pressure, and the residue was partitioned between diethyl ether and water. The ether layer was collected and washed successively with sat. aq. ammonium chloride solution and sat. aq. sodium bicarbonate solution. The ether layer was dried with magnesium sulfate. The solvent was removed under reduced pressure, and the residue was purified by column chromatography (eluent 10:1 hexanes:ethyl acetate). This gave 4.13 g (52% yield) of a white solid: $^1$H NMR (400 MHz, CDCl$_3$) δ ppm 0.88 (m, 8H) 1.14 (m, 8H) 1.39 (m, 12H) 1.67 (m, 6H) 2.41 (dd, J=16.47, 5.00 Hz, 1H) 2.70 (dd, J=16.47, 9.64 Hz, 1H) 4.31 (m, J=9.58, 7.29, 7.29, 5.12 Hz, 1H) 4.75 (qd, J=6.75, 6.59 Hz, 1H) 5.64 (d, J=7.08 Hz, 1H) 7.31 (m, 2H) 7.38 (m, 3H). MS (APCI) m+1/z=430 (loss of t-Bu group).

(S)-2-((R)-4-Cyclohexyl-2-methyl-butyl)-succinic acid 4-tert-butyl ester

A flask was charged with 4.13 g (8.50 mmol) of (5R,3S)-7-cyclohexyl-5-methyl-3-((4R,5R)-4-methyl-2-oxo-5-phenyl-oxazolidine-3-carbonyl)-heptanoic acid tert-butyl ester, 100 mL of THF, 25 mL of water, and the resulting mixture was cooled in a 0° C. bath. To this solution was added 0.57 g (13.6 mmol) of lithium hydroxide monohydrate and 3.48 mL (34 mmol) of 30% hydrogen peroxide. The mixture was stirred for 2.5 hours. The reaction was quenched by the addition of 4.29 g (34 mmol) of sodium sulfite in 26 mL water. The mixture was allowed to warm to room temperature and stirred overnight. The THF was removed under reduced pressure and the remaining material was further diluted with water. The water layer was made acidic by the slow addition of conc. HCl aq. The aqueous layer was extracted with dichloromethane. The organic layers were dried with magnesium sulfate. The resulting oil was purified by column chromatography (eluent 3:1 hexanes:ethyl acetate). This gave 2.19 g (79% yield) of a clear oil: $^1$H NMR (400 MHz, CDCl$_3$) δ ppm 0.88 (m, 5H) 1.17 (m, 10H) 1.43 (s, 10H) 1.68 (m, 7H) 2.35 (dd, J=16.35, 5.37 Hz, 1H) 2.60 (m, 1H) 2.87 (m, J=9.09, 9.09, 5.61, 5.49 Hz, 1H). MS (APCI) m+1/z is inconclusive.

(3S,5R)-3-Amino-7-cyclohexyl-5-methyl-heptanoic acid methyl ester

A flask was charged with 2.19 g (6.71 mmol) of (S)-2-((R)-4-cyclohexyl-2-methyl-butyl)-succinic acid 4-tert-butyl ester, 40 mL of toluene, 0.935 mL (6.71 mmol) of triethylamine, and 1.45 mL (6.71 mmol) of diphenylphosphorylazide. The mixture was stirred for 15 minutes at room temperature and then heated to 110° C. and stirred for 6 hours. The toluene was removed under reduced pressure, and the residue was taken up in diethyl ether. The ether layer was washed with 3M HCl aq., water, and brine. The ether was removed under reduced pressure, and the crude isocyanate was taken up in 3 M HCl aq. and heated at reflux for 8 hours. The water was removed under reduced pressure, and the residue was triturated with ether. This provided 1.45 g of an impure white solid. A portion of the white solid was dissolved in methanol, and HCl gas was bubbled through for 15 minutes. The acidic solution was stirred 2 hours. The methanol was removed under reduced pressure, and the crude ester was purified by column chromatography (4:1 dichloromethane:methanol). This gave 0.356 g of the pure ester: $^1$H NMR (400 MHz, CDCl$_3$) δ ppm 0.85 (m, 2H) 0.88 (d, J=8.00 Hz, 3H) 1.15 (m, 6H) 1.26 (m, 1H) 1.36 (ddd, J=13.73, 9.21, 4.64 Hz, 1H) 1.51 (m, 1H) 1.65 (m, 7H) 2.28 (dd, J=15.86, 8.78 Hz, 1H) 2.43 (dd, J=16.0, 4.00 Hz, 1H) 3.28 (m, J=8.97, 8.97, 4.39, 4.27 Hz, 1H) 3.69 (s, 3H). MS (APCI) m+1/z=256.

(3S,5R)-3-Amino-7-cyclohexyl-5-methyl-heptanoic acid

A flask was charged with 0.356 g of (3S,5R)-3-amino-7-cyclohexyl-5-methyl-heptanoic acid methyl ester and 20 mL of 3 M HCl, and the mixture was heated at reflux overnight. The mixture was cooled to room temperature and the solvent was removed under reduced pressure. This provided 0.340 g (88%) of a white solid HCl salt: $^1$H NMR (400 MHz, CD$_3$OD) δ ppm 0.87 (s, 2H) 0.95 (d, J=6.34 Hz, 3H) 1.21 (m, 6H) 1.35 (m, 1H) 1.43 (ddd, J=13.85, 8.24, 5.98 Hz, 1H) 1.55 (ddd, J=12.81, 6.34, 6.22 Hz, 1H) 1.64 (dd, J=8.30, 5.37 Hz, 2H) 1.71 (m, 5H) 2.57 (dd, J=17.45, 7.44 Hz, 1H) 2.70 (m, 1H) 3.59 (m, J=7.72, 7.72, 5.73, 5.43 Hz, 1H). MS (APCI) m+1/z=242.

EXAMPLE 5

(4R,5S)-3-[3-(2,4-Difluoro-phenyl)-propionyl]-4-methyl-5-phenyl-oxazolidin-2-one A flask was charged with 29.5 g (158 mmol) of 3-(2,4-difluoro-phenyl)-propionic acid, 700 mL of THF, and 82.8 mL of triethylamine. The mixture was cooled to 0° C. and 23.4 mL of trimethyl acetyl chloride was added slowly. The mixture was stirred cold for 1 hour. Then 8.06 g (190 mmol) of LiCl and 28.1 g of (4S,5R)-4-methyl-5-phenyl-oxazolidin-2-one was added. The mixture was allowed to warm room temperature and stirred overnight. The solids were filtered off, and the solvent was removed under reduced pressure. The residue was taken up in diethyl ether and washed with sat. aq. ammonium chloride, sat. aq. sodium bicarbonate, and the solvent was removed under reduced pressure. The crude residue was purified by column chromatography (3:1 dichloromethane/hexanes eluent) to give 54 g (99% yield) of the titled compound.

(4R,5S)-[(S)-2-(2,4-Difluoro-benzyl)-butyryl]-4-methyl-5-phenyl-oxazolidin-2-one A flask was charged with 54 g (156 mmol) of (4R,5S)-3-[3-(2,4-difluoro-phenyl)-propionyl]-4-methyl-5-phenyl-oxazolidin-2-one and 300 mL of dry THF, and the solution was cooled to −78° C. To this solution was added 172 mL (172 mmol) of 1 M NaHMDS in THF, and the mixture was stirred cold for 1 hour. Then 30.6 g (172 mmol) of ethyl triflate was added dropwise to the enolate solution, and the reaction mixture was warmed to −40° C. to −30° C. and stirred for 1.5 hours. The reaction mixture was quenched by the addition of aqueous brine. The THF was removed under reduced pressure and the residue was partitioned between EtOAc and water. The organics were collected, and EtOAc was removed under reduced pressure. The resulting crude oil was purified by column chromatography (3:1 hexanes/EtOAc eluent) to get 29.5 g of an impure oil that was used without further purification.

(S)-2-(2,4-Difluoro-benzyl)-butan-1-ol

A flask was charged with 29.5 g (~78.6 mmol) of (4R, 5S)-[(S)-2-(2,4-difluoro-benzyl)-butyryl]-4-methyl-5-phenyl-oxazolidin-2-one and 200 mL of dry THF, and the solution was cooled to 0° C. In a separate flask, 11.9 g (314 mmol) of sodium borohydride was taken up in 70 mL of water and added dropwise over 15 minutes to the imide solution. The mixture was allowed to warm to room temperature and stirred overnight. The reaction mixture was quenched with conc. HCl until pH=3 (keeping the reaction mixture temperature <20° C.). THF was removed under reduced pressure, and the residue was taken up in hexanes. The hexane layer was washed with sat. aq. sodium bicarbonate. The hexane layer was removed under reduced pressure, and the residue was purified by column chromatography (9:1 Hexanes/EtOAc) which gave 7.2 g (46% yield) of the titled compound as a clear oil.

(2S)-Methanesulfonic acid 2-(2,4-difluoro-benzyl)-butyl ester

A flask was charged with 7.2 g (36 mmol) of (S)-2-(2,4-difluoro-benzyl)-butan-1-ol and 30 mL of dichloromethane, and the solution was cooled to 0° C. To this solution was added 7.53 mL (54 mmol) of triethylamine, and the mixture was stirred cold for 5 minutes. Then 3.1 mL (39.6 mmol) of methane sulfonyl chloride was added dropwise. The reaction mixture was stirred at room temperature for 16 hours. The dichloromethane was removed under reduced pressure, and the residue was partitioned between 1 N HCl aq. and diethyl ether. The ether layer was collected and washed with sat. aq. sodium bicarbonate, water, and brine. The ether layer was dried over sodium sulfate, filtered, and the ether was removed under reduced pressure. This procedure gave 9.54 g (95% yield) of (2S)-methanesulfonic acid 2-(2,4-difluoro-benzyl)-butyl ester as an orange oil. This material was used without further purification.

(S)-2,4-Difluoro-1-(2-iodomethyl-butyl)-benzene

A flask was charge with 9.54 g (34.3 mmol) of (2S)-methanesulfonic acid 2-(2,4-difluoro-benzyl)-butyl ester, 10.3 g (68.6 mmol) of sodium iodide, and 60 mL of acetone. The solution was heated at reflux for 30 hours. The acetone was removed under reduced pressure. The residue was partitioned between water and hexanes. The organic layer was collected and washed with sodium bisulfite solution and brine. The hexane was removed under reduced pressure, and the crude oil was purified by column chromatography (hexanes eluent). This procedure gave 9.7 g (91% yield) of the titled compound as a clear oil.

2-tert-Butyl-5-[2-(2,4-difluoro-benzyl)-butyl]-3-methyl-4-oxo-tetrahydro-pyrimidine-1-carboxylic acid methyl ester A flask was charged with 1.35 mL (9.64 mmol) of diisopropyl amine and 15 mL of dry THF. The solution was cooled to −78° C. and 6.0 mL (9.64 mmol) of 1.6 M n-butyl lithium solution in hexanes was added. The mixture was warmed to 0° C. and stirred for 30 minutes. The mixture was cooled again to −78° C. and 2.0 g (8.76 mmol) of (2S)-2-tert-butyl-3-methyl-4-oxo-tetrahydro-pyrimidine-1-carboxylic acid methyl ester was added as a solution in 10 mL of THF. This mixture was warmed to 0° C. and stirred for 1 hour. The anion solution was cooled again to −78° C. and 2.99 g (9.64 mmol) of (S)-2,4-difluoro-1-(2-iodomethyl-butyl)-benzene was added as a solution in THF. The mixture was stirred at −78° C. for 4 hours. The reaction mixture was warmed to −21° C. and stirred at that temperature for 5 days. The reaction mixture was quenched with sat. aq. ammonium chloride solution. The crude reaction mixture was extracted with diethyl ether. The ether was removed under reduced pressure, and the crude residue was purified by column chromatography (9:1 hexanes/EtOAc eluent) which gave 1.67 g (46% yield) of the titled compound as a white solid.

(2R,4R)-2-Aminomethyl-4-(2,4-difluoro-benzyl)-hexanoic acid

A flask was charged with 0.5 g (1.2 mmol) of 2-tert-butyl-5-[2-(2,4-difluoro-benzyl)-butyl]-3-methyl-4-oxo-tetrahydro-pyrimidine-1-carboxylic acid methyl ester, 20 mL of dioxane, and 20 mL of conc. HCl solution. The mixture was stirred and heated at 110° C. for 4 days. The solvents were removed under reduced pressure. The residue was taken up in 20 mL of water and 4 drops of conc. HCl solution. The aqueous layer was washed with dichloromethane. The aqueous layer was collected and the water was removed under reduced pressure. The residue was treated with 2 mL of triethylamine, and the excess triethylamine was removed under reduced pressure. The remaining solid was purified by column chromatography (1:8:27 $NH_4OH$, MeOH, dichloromethane eluent). The resulting white solid was washed with acetonitrile and dried under vacuum. This gave 80 mg (24% yield) of the titled compound as a white solid.

EXAMPLE 6

3-(2-Methyl-pent-2-enoyl)-4-phenyl-oxazolidin-2-one

A flask was charged with 29.5 g (158 mmol) of 3-(2,4-difluoro-phenyl)-propionic acid, 700 mL of THF, and 82.8 mL of triethylamine. The mixture was cooled to 0° C. and 23.4 mL of trimethyl acetyl chloride was added slowly. The mixture was stirred cold for 1 hour. Then 8.06 g (190 mmol) of LiCl and 28.1 g of (4S,5R)-4-methyl-5-phenyl-oxazolidin-2-one was added. The mixture was allowed to warm room temperature and stirred overnight. The solids were filtered off, and the solvent was removed under reduced pressure. The residue was taken up in diethyl ether and washed with sat. aq. ammonium chloride, sat. aq. sodium bicarbonate, and the solvent were removed under reduced pressure. The crude residue was purified by column chromatography (3:1 dichloromethane/hexanes eluent) to give 54 g (99% yield) of the titled compound.

(4R,5S)-[(S)-2-(2,4-Difluoro-benzyl)-butyryl]-4-methyl-5-phenyl-oxazolidin-2-one A flask was charged with 54 g (156 mmol) of (4R,5S)-3-[3-(2,4-difluoro-phenyl)-propionyl]-4-methyl-5-phenyl-oxazolidin-2-one and 300 mL of dry THF, and the solution was cooled to −78° C. To this solution was added 172 mL (172 mmol) of 1 M NaHMDS in THF, and the mixture was stirred cold for 1 hour. Then 30.6 g (172 mmol) of ethyl triflate was added dropwise to the enolate solution, and the reaction mixture was warmed to −40° C. to −30° C. and stirred for 1.5 hour. The reaction mixture was quenched by the addition of aqueous brine. The THF was removed under reduced pressure and the residue was partitioned between EtOAc and water. The organics were collected, and EtOAc was removed under reduced pressure. The resulting crude oil was purified by column chromatography (3:1 hexanes/EtOAc eluent) to get 29.5 g of an impure oil that was used without further purification.

(S)-2-(2,4-Difluoro-benzyl)-butan-1-ol

A flask was charged with 29.5 g (~78.6 mmol) of (4R,5S)-[(S)-2-(2,4-difluoro-benzyl)-butyryl]-4-methyl-5-phenyl-oxazolidin-2-one and 200 mL of dry THF, and the solution was cooled to 0° C. In a separate flask, 11.9 g (314 mmol) of sodium borohydride was taken up in 70 mL of water and added dropwise over 15 minutes to the imide solution. The mixture was allowed to warm to room temperature and stirred overnight. The reaction mixture was quenched with conc. HCl until pH=3 (keeping the reaction mixture temperature <20° C.). THF was removed under reduced pressure, and the residue was taken up in hexanes. The hexane layer was washed with sat. aq. sodium bicarbonate. The hexane layer was removed under reduced pressure, and the residue was purified by column chromatography (9:1 Hexanes/EtOAc) which gave 7.2 g (46% yield) of the titled compound as a clear oil.

(2S)-Methanesulfonic acid 2-(2,4-difluoro-benzyl)-butyl ester

A flask was charged with 7.2 g (36 mmol) of (S)-2-(2,4-difluoro-benzyl)-butan-1-ol and 30 mL of dichloromethane, and the solution was cooled to 0° C. To this solution was added 7.53 mL (54 mmol) of triethylamine, and the mixture was stirred cold for 5 minutes. Then 3.1 mL (39.6 mmol) of methane sulfonyl chloride was added dropwise. The reaction mixture was stirred at room temperature for 16 hours. The dichloromethane was removed under reduced pressure, and the residue was partitioned between 1 N HCl aq. and diethyl ether. The ether layer was collected and washed with sat. aq. sodium bicarbonate, water, and brine. The ether layer was dried over sodium sulfate, filtered, and the ether was removed under reduced pressure. This procedure gave 9.54 g (95% yield) of the titled compound as an orange oil. This material was used without further purification.

(S)-2,4-Difluoro-1-(2-iodomethyl-butyl)-benzene

A flask was charge with 9.54 g (34.3 mmol) of (2S)-methanesulfonic acid 2-(2,4-difluoro-benzyl)-butyl ester, 10.3 g (68.6 mmol) of sodium iodide, and 60 mL of acetone. The solution was heated at reflux for 30 hours. The acetone was removed under reduced pressure. The residue was partitioned between water and hexanes. The organic layer was collected and washed with sodium bisulfite solution and brine. The hexane was removed under reduced pressure, and the crude oil was purified by column chromatography (hexanes eluent). This procedure gave 9.7 g (91% yield) of the titled compound as a clear oil.

2-tert-Butyl-5-[2-(2,4-difluoro-benzyl)-butyl]-3-methyl-4-oxo-tetrahydro-pyrimidine-1-carboxylic acid methyl ester A flask was charged with 1.35 mL (9.64 mmol) of diisopropyl amine and 15 mL of dry THF. The solution was cooled to −78° C. and 6.0 mL (9.64 mmol) of 1.6 M n-butyl lithium solution in hexanes was added. The mixture was warmed to 0° C. and stirred for 30 minutes. The mixture was cooled again to −78° C. and 2.0 g (8.76 mmol) of (2S)-2-tert-butyl-3-methyl-4-oxo-tetrahydro-pyrimidine-1-carboxylic acid methyl ester was added as a solution in 10 mL of THF. This mixture was warmed to 0° C. and stirred for 1 hour. The anion solution was cooled again to −78° C. and 2.99 g (9.64 mmol) of (S)-2,4-difluoro-1-(2-iodomethyl-butyl)-benzene was added as a solution in THF. The mixture was stirred at −78° C. for 4 hours. The reaction mixture was warmed to −21° C. and stirred at that temperature for 5 days. The reaction mixture was quenched with sat. aq. ammonium chloride solution. The crude reaction mixture was extracted with diethyl ether. The ether was removed under reduced pressure, and the crude residue was purified by column chromatography (9:1 hexanes/EtOAc eluent) which gave 1.67 g (46% yield) of the titled compound as a white solid.

(2R,4R)-2-Aminomethyl-4-(2,4-difluoro-benzyl)-hexanoic acid

A flask was charged with 0.5 g (1.2 mmol) of 2-tert-butyl-5-[2-(2,4-difluoro-benzyl)-butyl]-3-methyl-4-oxo-tetrahydro-pyrimidine-1-carboxylic acid methyl ester, 20 mL dioxane, and 20 mL of conc. HCl solution. The mixture was stirred and heated at 110° C. for 4 days. The solvents were removed under reduced pressure. The residue was taken up in 20 mL of water and 4 drops of conc. HCl solution. The aqueous layer was washed with dichloromethane. The aqueous layer was collected and the water was removed under reduced pressure. The residue was treated with 2 mL of triethylamine, and the excess triethylamine was removed under reduced pressure. The remaining solid was purified by column chromatography (1:8:27 $NH_4OH$, MeOH, dichloromethane eluent). The resulting white solid was washed with acetonitrile and dried under vacuum. This gave 80 mg (24% yield) of the titled compound as a white solid.

EXAMPLE 7

(S)-3-((E)-2-Methyl-pent-2-enoyl)-4-phenyl-oxazolidin-2-one

A 20 L jacketed reactor was fitted with a reflux condenser and a nitrogen inlet. To the flask was charged 1006 g (8.81 mol) of (E)-2-methyl-2-pentenoic acid, 1250 g (7.661 mol) of (S)-(+)-4-phenyl-oxazolidin-2-one, 2179 g (8.81 mol) of 2-ethoxy-1-ethoxycarbonyl-1,2-dihydroquinoline (EEDQ), 81 g (1.915 mol) of lithium chloride, and 12.5 L of ethyl acetate (EtOAc). The reaction was heated to 75° C. for 20 hours and then cooled to room temperature. The reaction solution was extracted 3× with 4 L aliquots of 1N HCl and 1× with 4 L of 0.2N NaOH. The 20 L reactor was fitted with a distillation head. The organic layer was distilled to remove, in succession: 6.5 L of EtOAc, after which 8 L of heptane was added back to the reactor; 4 L of EtOAc/heptane, after which 4 L of heptane was added to the reactor; and 4 L of EtOAc/heptane, after which 8 L of heptane was added to the reactor. After an additional 2 L of EtOAc/heptane was removed by distillation, the reaction mixture was cooled to an internal temperature of 40° C., and the reactor contents were charged to a filter and filtered under 5 psig of nitrogen washing with 8 L of heptane. The solids were dried under 5 psig of nitrogen overnight to give 1772 g of the titled compound: $^1$H-NMR (DMSO) 7.363-7.243 (m, 5H), 6.137-6.096 (m, 1H), 5.434-5.394 (m, 1H), 4.721-4.678 (t, 1H, J=8.578), 4.109-4.069 (m, 1H), 2.119-2.044 (m, 2H), 1.703-1.700 (d, 3H, J=1.364), 0.945-0.907 (t, 3H, J=7.603); Anal Calc'd for $C_{15}H_{17}N_1O_3$: C, 69.48; H, 6.61; N, 5.40. Found: C, 68.66; H, 6.60; N, 5.60; MS (Ion Mode: APCI) m/z=260 $[M+1]^+$.

(4S,5R)-3-((E)-2-Methyl-pent-2-enoyl)-4,5-diphenyl-oxazolidin-2-one

To a solution of (E)-2-methyl-2-pentenoic acid (5.3 g, 47 mmol) in 250 mL of THF at 0° C. was added 16.3 mL (117 mmol) of triethylamine, then 5.8 mL (47 mmol) of pivaloyl chloride resulting in a thick suspension. The mixture was stirred for 1 hour at 0° C. at which time 2.0 g (47 mmol) of lithium chloride was added in one portion, followed by 10 g (42 mmol) of (4S,5R)-4,5-diphenyl-2-oxazolidinone in four batches. Stirring was maintained throughout the solid additions. The reaction mixture was stirred for 1 hour at 0° C., and for 1 hour at ambient temperature, and was vacuum filtered through a coarse frit and concentrated. The residue was partitioned between EtOAc/water, and the organics were dried over $MgSO_4$ and concentrated. To the residue was added 200 mL of MTBE and the mixture was warmed cautiously with swirling. The warm slurry was filtered to provide 13.0 g (83% yield) of the titled compound as a colorless solid: $^1$H NMR ($CDCl_3$) δ 7.12 (m, 3H), 7.08 (m, 3H), 6.93 (m, 2H), 6.86 (m, 2H), 6.14 (m, 1H), 5.90 (d, J=7.8 Hz, 1H), 5.69 (d, J=7.8 Hz, 1H), 2.23 (pent, J=7.6 Hz, 2H), 1.92 (s, 3H), 1.07 (t, J=7.6 Hz, 3H). The titled acylated oxazolidinone may be used in the next step instead of (S)-3-((E)-2-Methyl-pent-2-enoyl)-4-phenyl-oxazolidin-2-one.

(2R,3R,4S)-3-(2,3-Dimethyl-pentanoyl)-4-phenyl-oxazolidin-2-one

A 20 L jacketed reactor was fit with a gas inlet and a 2 L dripping funnel. A nitrogen sweep was begun over the reactor and maintained throughout the process. To the reactor was charged 392 g (9.26 mol) of lithium chloride, 1332 g (6.479 mol) of copper bromide dimethylsulfide complex and 11 L of tetrahydrofuran. The reaction was stirred for 30 minutes at room temperature and then cooled to −15° C. To the reaction mixture was added 4.268 L (12.80 mol) of 3.0M methyl magnesium chloride at a rate such that the reaction temperature did not exceed −10° C. Upon completion of the addition, the cuprate solution was allowed to stir at −5° C. overnight. To the cuprate solution was added 500 g (3.09 mol) of (S)-3-((E)-2-methyl-pent-2-enoyl)-4-phenyl-oxazolidin-2-one as a solid. The reaction was stirred at −3° C. for 2 hours. The reaction solution was charged to a 22 L round bottom flask containing 800 mL of acetic acid and 2 L of tetrahydrofuran at a rate such that the temperature of the quench solution did not exceed 25° C. To the quenched solution was added 6 L water. The resulting emulsion was filtered and the layers were separated. The organic layer was extracted with 9 L of 4.8 M $NH_4OH$ followed by 9 L of saturated $NH_4Cl$. The organic layer was clarified through a plug of magnesol. The organic layer was concentrated to give 822 g of a crude solid. The crude solid was recrystallized from 8 L of 20% $H_2O$ in MeOH, filtered and dried in a vacuum oven to give 550 g of a white solid. The white solid was recrystallized from 5 L of 20% $H_2O$ in MeOH, filtered and dried in a vacuum oven to give 475 g of the titled compound: $^1$H-NMR (DMSO) 7.338-7.224 (m, 5H), 5.431-5.399 (q, 1H, J=4.288), 4.696-4.652 (t, 1H, J=8.773), 4.120-4.087 (m, 1H), 3.622-3.556 (m, 1H), 1.648-1.584 (m, 1H), 1.047-0.968 (m, 1H), 0.900-0.883 (d, 3H, J=6.823), 0.738-0.721 (d, 3H, J=6.628), 0.693-0.656 (t, 3H, J=7.408); Anal Calc'd for $C_{16}H_{21}N_1O_3$: C, 69.79; H, 7.69; N, 5.09. Found: C, 69.81; H, 7.61; N, 5.07; MS (Ion Mode: APCI) m/z=276 $[M+1]^+$.

(2R,3R)-2,3-Dimethyl-pentanoic acid

A 20 L jacketed flask was fit with a gas inlet. A nitrogen purge was begun over the reactor and maintained throughout the process. To the flask was charged 450 g (1.634 mol) of (2R,3R,4S)-3-(2,3-dimethyl-pentanoyl)-4-phenyl-oxazolidin-2-one and 3.375 L tetrahydrofuran. The contents of the reactor were stirred at 15° C. In a separate 3 L round bottom flask, placed in an ice bath, was charged 500 mL of water, 137 g (3.269 mol) of LiOH—$H_2O$ and 942 mL (9.81 mol) of 30% wt/wt $H_2O_2$. The contents of the 3 L round bottom flask were stirred for 3 minutes and then poured into the 20 L jacketed reactor at a rate such that the temperature did not exceed 25° C. The reaction was stirred at 15° C. for 2 hours and then raised to 25° C. and stirred for an additional 2 hours. The jacket temperature of the reactor was set to −20° C. To the reaction was added 1.66 L of saturated $NaHSO_3$ at a rate such that the temperature of the reaction did not exceed 25° C. The layers were separated. The aqueous layer was extracted 2× with 1 L aliquots of MTBE. The organic phases were combined and concentrated to give a solid/oil mixture. The solid/oil mixture was slurried in 1.7 L of hexane. The slurry was filtered and the collected solids were washed with 1.7 L of hexane. The hexane filtrates were extracted 2× with 1.35 L aliquots of 1N NaOH. The aqueous extracts were combined and extracted with 800 mL of dichloromethane. The aqueous layer was then acidified with 240 mL of concentrated hydrochloric acid. The aqueous solution was extracted 2× with 1 L aliquots of dichloromethane. The organic extracts were combined, dried over $MgSO_4$ and concentrated to give 201 g of the titled compound: $^1$H-NMR (DMSO) 11.925 (bs, 1H), 2.204-2.135 (m, 1H), 1.556-1.490 (m, 1H), 1.382-1.300 (m, 1H), 1.111-1.000 (m, 1H), 0.952-0.934 (d, 3H, J=7.018), 0.809-0.767 (m, 6H); Gas Chromatogram 9.308 minutes, 98.91% area; Anal Calc'd for $C_7H_{14}O_2$: C, 64.58; H, 10.84; N, 0. Found: C, 64.39; H, 10.77; N, 0.18; MS (Ion Mode: APCI) m/z=131 $[M+1]^+$.

(4R,5R)-4,5-Dimethyl-3-oxo-heptanoic acid ethyl ester

To a 1 L round bottom flask equipped with a nitrogen inlet was charged 22 g (230 mmol) of magnesium chloride, 39 g (230 mmol) of potassium ethyl malonate and 200 mL of dimethylformamide. The contents of the flask were stirred at 50° C. for 1 hour and then cooled to 35° C. In a separate 500 mL, nitrogen inerted flask was added 200 mL of dimethylformamide, 28.6 g (177 mmol) of carbonyl diimidazole and 20 g of (2R,3R)-2,3-dimethyl-pentanoic acid was dripped in over 30 minutes. When the gas evolution had ceased, the contents of the 500 mL flask were added to the 1 L flask. The reaction was stirred for 2 days at 35° C. The reaction was cooled to room temperature and diluted with 800 mL of 1N HCl. The aqueous solution was extracted 3× with 1 L aliquots of MTBE. The organic extracts were combined and extracted with 200 mL of saturated $NaHCO_3$. The organic layer was dried over $MgSO_4$ and concentrated to give 31.74 g of the titled compound: $^1$H-NMR ($CDCl_3$) 4.180-4.120 (m, 2H), 3.454 (s, 2H), 2.522-2.453 (q, 1H, J=7.018), 1.738-1.673 (m, 1H), 1.418-1.328 (m, 1H), 1.270-1.217 (m, 3H), 1.113-1.010 (m, 4H), 0.889-0.815 (m, 5H); MS (Ion Mode: APCI) m/z=201 $[M+1]^+$.

(4R,5R)-3-Methoxyimino-4,5-dimethyl-heptanoic acid ethyl ester (4R,5R)-4,5-Dimethyl-3-oxo-heptanoic acid ethyl ester (21.23 g, 106 mmol) was dissolved in 200 mL of EtOH and added to 10.6 g (127 mmol) of methoxylamine-HCl and 10.6 g (127 mmol) of sodium acetate solids. The slurry was stirred at room temperature for 48 hours. MTBE (200 mL) and 100 mL of water were added, and the resulting phases were separated. The organic phase was washed with 100 mL of water and was evaporated to yield a two-phase mixture. Hexanes (100 mL) were added and the phases were separated. The aqueous phase was extracted with 50 mL of hexanes and the combined organic phases were washed with 50 mL of water, dried over magnesium sulfate, and evaporated to give 21.24 g (87.4% yield) of the titled compound as a clear yellow oil: $^1$H NMR (CDCl$_3$, 399.77 MHz) δ 0.84-0.88 (m, 6H), 1.07 (d, J=7.1 Hz, 3H), 1.24 (t, J=7.1 Hz, 3H), 1.4-1.6 (m, 2H), 2.24 (m, 1H), 3.08 (d, J=15.8 Hz, 1H), 3.19 (d, J=15.8 Hz, 1H), 3.80 (s, 3H), 4.10-4.2 (m, 3H). Low resolution mass spec: nominal m/e calc'd for C$_{12}$H$_{23}$NO$_3$ (M+H)$^+$: 230. Found: m/e 230.

(4R,5R)-3-Amino-4,5-dimethyl-hept-2-(Z)-enoic acid ethyl ester

A solution of 21.1 g (92 mmol) of (4R,5R)-3-methoxyimino-4,5-dimethyl-heptanoic acid ethyl ester in methanol (200 mL) was treated with Sponge nickel (10 g, Johnson Matthey A7000). The resulting slurry was hydrogenated on a Parr shaker type hydrogenator at 50 psig and room temperature for 20 hours. At this time an additional 10 g of the nickel catalyst was added and hydrogenation was continued for a total of 42.0 hours. The slurry was filtered, the solids were washed with fresh methanol, and the combined filtrate was evaporated to give 17.75 g (96.8% yield) of the titled compound as a colorless oil: $^1$H NMR (CDCl$_3$, 399.77 MHz) δ 0.83-0.89 (m, 6H), 1.1 (d, J=6.8 Hz, 3H), 1.25 (t, J=7.1 Hz, 2H), 1.35-1.6 (m, 4H), 1.85-1.93 (m, 1H), 4.1 (q, J=7.0 Hz, 2H), 4.5 (s, 1H). Low resolution mass spec: nominal m/e calc'd for C$_{11}$H$_{21}$NO$_2$ (M+H)$^+$: 200. Found: m/e 200.

(4R,5R)-3-Acetylamino-4,5-dimethyl-hept-2-(Z)-enoic acid ethyl ester

A solution of 15.84 g (79.84 mmol) of (4R,5R)-3-amino-4,5-dimethyl-hept-2-(Z)-enoic acid ethyl ester and 6.89 g (7.04 mL, 87.82 mL) of pyridine was stirred in 200 mL of methylene chloride and cooled to 0° C. A solution of 6.85 g (6.21 mL, 87.82 mL) of acetyl chloride in 20 mL of methylene chloride was added dropwise over 1 hour. The solution was warmed to room temperature and stirred for two hours. 1M hydrochloric acid (100 mL) was added and the phases were separated. The organic phase was washed with saturated aqueous NaHCO$_3$ solution and dried briefly over Na$_2$SO$_4$. The solvent was evaporated and then the resulting oil was passed through a short column of silica (200 g silica, 230-400 mesh) with 8:1 (v/v) hexane/EtOAc. The product-containing fractions were evaporated to give 13.75 g (71.7% yield) of the titled compound as a clear, nearly colorless oil: $^1$H NMR (CDCl$_3$, 399.77 MHz) δ 0.84 (t, J=7.1 Hz, 3H), 0.95 (d, J=6.8 Hz, 3H), 1.0 (d, J=7.0 Hz, 3H), 1.29 (t, J=7.2 Hz, 3H), 1.30-1.45 (m, 3H), 2.13 (s, 3H), 3.79-3.82 (m, 1H), 4.11-4.18 (m, 2H), 5.01 (s, 1H). Low resolution mass spec: nominal m/e calc'd for C$_{13}$H$_{23}$NO$_3$ (M+H)$^+$: 242. Found: m/e 242.

(3R,4R,5R)-3-Acetylamino-4,5-dimethyl-heptanoic acid ethyl ester

A solution containing 13.75 g (57 mmol) of (4R,5R)-3-acetylamino-4,5-dimethyl-hept-2-(Z)-enoic acid ethyl ester in 200 mL of methanol was treated with 5% Pd/Al$_2$O$_3$ (1.5 g, Johnson Matthey #2127, lot 13449). The resulting slurry was hydrogenated on a Parr shaker type hydrogenator at 40 psig to 50 psig and room temperature for a total of 3.8 hours. The slurry was filtered and the solids were washed with fresh methanol. The combined filtrate was evaporated to give 13.63 g (98.6% yield) of the titled compound as a colorless oil: $^1$H NMR (CDCl$_3$, 399.77 MHz) δ 0.82 (d, J=7.0 Hz, 3H), 0.86 (t, J=7.3 Hz, 3H), 0.90 (d, J=6.5 Hz, 3H), 0.98-1.1 (m, 2H), 1.25 (t, J=7.2 Hz, 2H), 1.3-1.6 (m, 2H), 1.96 (s, 3H), 2.48 (dd, J=16, 5.65 Hz, 1H), 2.53 (dd, J=16, 5.2 Hz, 1H), 4.08-4.19 (m, 2H), 4.27-4.34 (m, 1H), 5.86 (br d, J=8.9 Hz, 1H). Low resolution mass spec: nominal m/e calc'd for C$_{13}$H$_{25}$NO$_3$ (M+H)$^+$: 244. Found: m/e 244.

(3R,4R,5R)-3-Amino-4,5-dimethyl-heptanoic acid hydrochloride (3R,4R,5R)-3-Acetylamino-4,5-dimethyl-heptanoic acid ethyl ester (13.63 g, 56.0 mmol) was heated under reflux with 200 mL of 1M hydrochloric acid for 72 hours. The solution was cooled and extracted 2× with 50 mL aliquots of MTBE. The aqueous phase was evaporated to a semisolid. Acetonitrile (4×100 mL) was added and evaporated to give 10.75 g (89% yield) of the titled compound as a white crystalline solid: $^1$H NMR (CD$_3$OD, 399.77 MHz) 0.87 (t, J=7.3 Hz, 3H), 0.94 (t, J=6.6 Hz, 6H), 1.02-1.15 (m, 1H), 1.37-1.53 (m, 2H), 1.58-1.68 (m, 1H), 2.64 (dd, J=17.5, 7.4 Hz, 1H), 2.73 (dd, J+17.5, 4.8 Hz, 1H), 3.54-3.61 (m, 1H). Low resolution mass spec: nominal m/e calc'd for C$_9$H$_{20}$ClNO$_2$ (M+H)$^+$: 174. Found: m/e 174.

(3R,4R,5R)-3-Amino-4,5-dimethyl-heptanoic acid (3R,4R,5R)-3-Amino-4,5-dimethyl-heptanoic acid hydrochloride (10.8 g, 51.5 mmol) was dissolved in 50 mL of methanol. To this solution was added triethylamine (5.2 g, 7.2 mL, 51.5 mmol). The solution was stirred for 10 minutes and then evaporated to a flocculent solid. Dichloromethane (376 mL) was added and the resulting slurry was stirred at room temperature for 45 minutes. Next, 188 mL of acetonitrile was added and the slurry was stirred for 30 minutes and then filtered. The solids were washed with 20 mL of 2:1 (v/v) dichloromethane-acetonitrile and dried on a nitrogen press to give 7.64 g (85.6% yield) of the titled compound as a white solid: $^1$H NMR (CD$_3$OD, 399.77 MHz) 0.88 (t, J=7.5 Hz, 3H), 0.91 (d, J=7.0 Hz, 3H), 0.94 (d, J=6.6 Hz, 3H), 0.98-1.12 (m, 1H), 1.32-1.43 (m, 1H), 1.43-1.64 (m, 2H), 2.26 (dd, J=16.5, 9.9 Hz, 1H), 2.47 (dd, J=9.5, 3.7 Hz, 1H), 3.28-3.36 (m, 1H). Low resolution mass spec: nominal m/e calc'd for C$_9$H$_{19}$NO$_2$ (M+H)$^+$: 174. Found: m/e 174.

(3R,4R,5R)-3-Amino-4,5-dimethyl-heptanoic Acid-1/6-succinic acid complex-1/6-hydrate, i.e., 6-((3R,4R,5R)-3-amino-4,5-dimethyl-heptanoic acid): 1-(succinic acid): 1-(H$_2$O)

(3R,4R,5R)-3-Amino-4,5-dimethyl-heptanoic acid (7.6 g, 44 mmol) and succinic acid (2.6 g, 22 mmol) were suspended in 20.2 mL of water. The slurry was heated to 100° C. to dissolve the solids. Acetonitrile (253 mL) was added to the hot solution. The mixture was stirred at 55° C. for 1 hour, and then cooled gradually to room temperature overnight. The resulting solids were filtered, washed with 10 mL of acetonitrile, and dried on a nitrogen press to give 6.21 g (72% yield) of the titled compound as fluffy white crystals: $^1$H NMR (CD$_3$OD, 399.77 MHz) $^1$H NMR (CD$_3$OD, 399.77

MHz) 0.88 (t, J=7.5 Hz, 3H), 0.91 (d, J=7.0 Hz, 3H), 0.94 (d, J=6.6 Hz, 3H), 0.98-1.12 (m, 1H), 1.32-1.43 (m, 1H), 1.43-1.64 (m, 2H), 2.26 (dd, J=16.5, 9.9 Hz, 1H), 2.47 (dd, J=19.5, 3.7 Hz, 1H), 2.50 (s, 0.67H), 3.28-3.36 (m, 1H). Low resolution mass spec: nominal m/e calc'd for $C_9H_{19}NO_2$ (M+H)$^+$: 174. Found: m/e 174. Anal. calc'd for 6-((3S,4R,5R 3-amino-4,5-dimethyl-heptanoic Acid): 1-(succinic Acid): 1-($H_2O$), $C_{58}H_{122}N_6O_{13}$: C, 59.26; H, 10.46; N, 7.15. Found: C, 59.28; H, 10.58; N, 7.09. KF calc'd for $C_{58}H_{122}N_6O_{13}:H_2O$, 1.43 wt %. Found: $H_2O$, 1.50 wt %.

EXAMPLE 8

(4S,5R)-4,5-Diphenyl-oxazolidin-2-one

To a 5 L round bottom flask equipped with an overhead stirrer, thermocouple and distillation head, was charged 550 g (2.579 mol) of (1R,2S)-diphenyl-2-aminoethanol, 457 g (3.868 mol, 1.5 eq) of diethylcarbonate, 18 g (0.258 mol, 0.1 eq) of NaOEt in 100 mL of EtOH and 3.5 L of toluene. The reaction was heated until an internal temperature of 90° C. was reached and EtOH distillation began. The reaction was refluxed until an internal temperature of 110° C. was reached (7 hours). For every 500 mL of solvent that was removed via the distillation head, 500 mL of toluene was added back to the reaction. A total of about 1.6 L of solvent was removed. The reaction was allowed to cool to room temperature and then filtered on a 3 L coarse fritted funnel with 2 psig $N_2$. Nitrogen was blown over the cake overnight to give 580 g (94% yield) of the titled compound: $^1$H NMR (DMSO) 7.090-6.985 (m, 6H), 6.930-6.877 (m, 4H), 5.900 (d, 1H, J=8.301), 5.206 (d, 1H, J=8.301).

(4S,5R)-3-((E)-2-Methyl-hex-2-enoyl)-4,5-diphenyl-oxazolidin-2-one (Alternative A)

A 20 L jacketed reactor was fitted with a reflux condenser. To the reactor was charged 1100 g (4.597 mol) of (4S,5R)-4,5-diphenyl-oxazolidin-2-one, 884 g (6.896 mol) (E)-2-methyl-2-pentenoic acid, 1705 g (6.896 mol) of EEDQ, 48 g (1.149 mol) of LiCl and 16 L of EtOAc. The reaction mixture was heated to 65° C. and was held for 200 minutes. The reaction mixture was cooled to room temperature and was extracted 3× with 3.5 L aliquots of 1N HCl. The combined aqueous extracts were filtered to give a white solid. The recovered white solid was added back to the organic layer. The 20 L reactor was fitted with a distillation head and the organic layer was distilled to remove in succession: 13.5 L of EtOAc, after which 5 L of heptane was added to the reactor; 5 L of EtOAc/heptane, after which 5 L of heptane was added to the reactor; and 2.7 L of EtOAc/heptane, after which 2.7L of heptane was added to the reactor. The contents of the reactor were cooled to 25° C. and the resulting mixture was filtered under 5 psig nitrogen while washing with 4 L of heptane. The wet cake was dried under nitrogen pressure overnight to give 1521 g of the titled compound: $^1$H NMR (DMSO) 7.12-6.94 (m, 8H), 6.834 (dd, 2H, J=7.813, 1.709), 6.060 (d, 1H, J=8.057), 6.050 (td, 1H, J=7.447, 1.221), 5.795 (d, 1H, J=8.057), 2.119-2.064 (m, 2H), 1.778 (d, 3H, J=0.997), 1.394 (m, 2H), 0.874 (t, 3H, J=7.324); Anal Calc'd for $C_{22}H_{23}N_1O_3$: C, 75.62; H, 6.63; N, 4.01. Found: C, 75.26; H, 6.72; N, 3.95.

(4S,5R)-3-(2-(E)-Methyl-hex-2-enoyl)-4,5-diphenyl-oxazolidin-2-one (Alternative B)

To a solution of (E)-2-methyl-2-hexenoic acid (6.0 g, 47 mmol) in 250 mL of THF at 0° C. was added 16.3 mL (117 mmol) of triethylamine, then 5.8 mL (47 mmol) of pivaloyl chloride resulting in a thick suspension. The mixture was stirred for 1 hour at 0° C. at which time 2.0 g (47 mmol) of lithium chloride was added in one portion, followed by 10.0 g (42 mmol) of (4S,5R)-4,5-diphenyl-2-oxazolidinone in four batches. Stirring was maintained throughout the solid additions. The resulting mixture was stirred for 1 hour at 0° C., then for 1 hour at ambient temperature, and was vacuum filtered through a coarse frit and concentrated. The residue was partitioned between EtOAc/water, and the organics were dried over $MgSO_4$ and concentrated. To the residue was added 100 mL of MTBE and the mixture warmed cautiously with swirling. The warm slurry was filtered to provide 10.5 g (64% yield) of the titled compound as a colorless solid: $^1$H NMR (CDCl$_3$) δ 7.12 (m, 3H), 7.07 (m, 3H), 6.94 (m, 2H), 6.84 (m, 2H), 6.17 (m, 1H), 5.89 (d, J=7.8 Hz, 1H), 5.68 (d, J=7.8 Hz, 1H), 2.18 (m, 2H), 1.92 (s, 3H), 1.50 (m, 2H), 0.96 (t, J=7.6 Hz, 3H).

(4S,5R)-3-((2R,3R)-2,3-Dimethyl-hexanoyl)-4,5-diphenyl-oxazolidin-2-one

A 22 L 4-neck round bottom flask was equipped with an addition funnel, mechanical stirrer, and nitrogen inlet. The system was purged with nitrogen for 1 hour. THF (6 L) were charged to the flask followed by 1236 g (6.01 mol) of CuBr.S(CH$_3$)$_2$ and 364 g (8.59 mol) of LiCl. The reaction was stirred for 15 minutes at ambient temperature. The solution was cooled to −35° C. and 3.96 L (11.88 mol) of a 3M solution of CH$_3$MgCl in THF was charged at a rate as to keep the internal temperature of the reaction mixture below −25° C. The reaction was stirred for 1 hour after the addition of CH$_3$MgCl was complete. (4S,5R)-3-((E)-2-Methyl-hex-2-enoyl)-4,5-diphenyl-oxazolidin-2-one (1.00 Kg, 2.86 mol) was added as a solid in one portion and the reaction was stirred at −30° C. for 4 hours. The reaction mixture was transferred over a 2 hour period into another 22 L flask equipped with a mechanical stirrer, transfer line, vacuum line, and containing 4 L of 1:1 acetic acid:THF solution cooled in an ice-water bath. The quenched solution was stirred for 30 minutes and then diluted with 4 L of 2M NH$_4$OH in saturated aqueous NH$_4$Cl and 2 L of water. The biphasic mixture was stirred for 15 minutes and the phases separated. The organic phase was washed 4× with 4 L aliquots of the 2M NH$_4$OH solution. No more blue color was observed in the washes or the organic phase so the organic phase was diluted with 8 L of water and the THF was distilled off until the internal temperature of the distillation pot reached 95° C. The suspension was cooled to ambient temperature and filtered. The solids were washed with 4 L of water and suction dried to give 868.2 g of an off white solid. This material was recrystallized from 2 L of 95:5 heptane: toluene with a cooling rate of 5° C. per hour to provide 317.25 g of the titled compound as a white solid: $^1$H NMR (CDCl$_3$) 7.12-6.85 (m, 10H), 5.90 (d, 1H, J=8.06 Hz), 5.72 (d, 1H, J=7.81), 3.83-3.76 (m, 1H), 1.95-1.89 (m, 1H), 1.35-1.31 (m, 1H), 1.11 (d, 3H, J=6.84), 1.10-0.95 (m, 3H), 0.92 (d, 3H, J=6.59), 0.76 (t, 3H, J=7.20) MS (APCI) M+1=366.2.

(2R,3R)-2,3-Dimethyl-hexanoic acid

A 12 L, 4-necked round bottom flask, equipped with a mechanical stirrer, 500 mL addition funnel, nitrogen inlet, and thermometer, was charged with 4515 mL of THF and 330.0 g of (4S,5R)-3-((2R,3R)-2,3-dimethyl-hexanoyl)-4,5-diphenyl-oxazolidin-2-one. The resulting liquid mixture (all solids dissolved) was cooled to −5° C. to 0° C. using an acetone/ice bath. A solution of 60.6 g of LiOH—H₂O in 1800 mL of deionized water was cooled to 0° C. to 5° C. and was combined with 512 g of cold 30% (wt/wt) hydrogen peroxide in a 2 L Erlenmeyer flask. The solution was kept cold using an ice/water bath. After the oxazolidinone/THF solution in the 12 L reaction flask reached −5° C. to 0° C., the addition funnel was charged with approximately one quarter of the cold LiOH/water/H₂O₂ solution. While maintaining a nitrogen sweep to minimize oxygen concentration in the reactor headspace, the LiOH/water/H₂O₂ solution was added dropwise to the vigorously stirred oxazolidinone/THF solution at such a rate as to maintain the reaction temp at 0° C. to 5° C. The addition funnel was recharged with approximately one quarter of the cold LiOH/water/H₂O₂ solution as required until all of the solution had been added to the reaction mixture (about 40 minutes for 0.45 mol scale). After the addition was completed, the mixture was stirred at 0° C. to 5° C. for 5 hours, during which the reaction mixture changed from a homogeneous solution to white slurry. A solution of 341 g of Na₂SO₃ and 188 g of NaHSO₃ in 2998 mL of deionized water (15 wt %) was added dropwise to the reaction mixture over about a 1.5 hour period (reaction was exothermic) via the addition funnel, while maintaining the reaction temperature at 0° C. to 10° C. Following the addition, the reaction mixture was stirred at 0° C. to 10° C. for 1 hour. The reaction mixture was tested with potassium iodide-starch test paper to ensure the absence of peroxides. The reaction mixture was charged with 2000 mL of EtOAc and was stirred 5 minutes. The phases were separated and the aqueous phase was extracted with 2000 mL of EtOAc. The combined organic extract was washed with brine (2×1500 mL). The colorless organic solution was concentrated under vacuum (35° C.-40° C.) to a "wet," white solid. Heptane (1000 mL) was added and the slurry was concentrated under vacuum (35° C.-40° C.) to a wet, white solid. Heptane (5000 mL) was added and the slurry was maintained at 0° C. to 5° C. for 16 hours and then at −10° C. to −5° C. for 1 hour. The cold slurry was filtered through a thin pad of celite, and the filter cake was washed with 100 mL of −10° C. to −5° C. heptane. The colorless filtrate was concentrated under vacuum (40° C.-45° C.) to give 130 g of the titled compound as a pale yellow oil: ¹H NMR (400 MHz, CHLOROFORM-D) 0.89 (t, J=7.00 Hz, 3H), 0.94 (d, J=6.8 Hz, 3H), 1.13 (d, J=7.0 Hz, 3H), 1.75-1.82 (m, 1H), 2.34-2.41 (m, 1H); GC Chiral purity: 99.18% (with 0.82% diastereomer) (direct acid method). Chemical purity: 100%. Anal. Calc'd for $C_8H_{16}O_2$: C, 66.63; H, 11.18. Found: C, 66.15; H, 11.41.

(4R,5R)-4,5-Dimethyl-3-oxo-octanoic acid ethyl ester (Alternative A)

A 5 L 3-neck round bottom flask, equipped with a reflux condenser, mechanical stirrer, nitrogen inlet, and thermometer, was charged with 1390 mL of dry THF and 389.3 g of potassium ethyl malonate. MgCl₂ (217.8 g) was added in three equal portions so that the internal temperature was less than 50° C. The resulting grey slurry was heated to 55° C. to 60° C. using a temperature controlled heating mantle. The mixture was stirred at 55° C. to 60° C. for 5 hours. A 2 L 3-neck round bottom flask, equipped with a 500 mL addition funnel, mechanical stirrer, nitrogen inlet, and thermometer, was charged with 680 mL of dry THF and 286.8 g of 1,1'-carbonyldiimidazole (CDI). The addition funnel was charged portion-wise with a solution of 219.9 g of (2R,3R)-2,3-dimethyl-hexanoic acid in 350 mL of dry THF. The entire dimethyl-hexanoic acid acid/THF solution was added dropwise to the stirred CDI/THF suspension at such a rate so as to control the evolution of CO₂ and to maintain the reaction at a temperature of 20° C. to 25° C. Following the addition, the reaction mixture was stirred at 20° C. to 25° C. for 1 hour, during which the slurry became a pale yellow solution. After the 5-hour reaction time, the malonate/MgCl₂ reaction mixture was cooled to 20° C. to 25° C. and the condenser was replaced with a 1 L addition funnel. The addition funnel was charged portion-wise with the dimethylhexanoic acid/CDI/THF reaction mixture. This entire reaction mixture was added dropwise to the stirred malonate/MgCl₂/THF reaction mixture over about 10 minutes. After the addition was completed, the reaction mixture was heated to 35° C. to 40° C. Some effervescence was noted. The reaction mixture was stirred at 35° C. to 40° C. for 16 hour. The reaction mixture was cooled to 20° C. to 25° C. A 12 L 3-neck round bottom flask, equipped with a mechanical stirrer and thermometer, was charged with 3060 mL of 2N aq. HCl. The reaction mixture (a grey suspension) was added portion-wise to the aq. HCl solution while maintaining an internal temperature of 20° C.-25° C. The reaction temperature was moderated with an ice/water bath; the reaction mixture pH was about 1. Following the addition, the reaction mixture was stirred at 20° C. to 25° C. for 2 hours. The reaction mixture was subsequently charged with 4000 mL of EtOAc and was stirred for 5 minutes. The phases were separated and the aqueous phase was extracted with 2000 mL of EtOAc. The combined organic extract was washed sequentially with: 1N aq. HCl (2×1500 mL); 1000 mL of water (incomplete phase separation); half saturated aq. Na₂CO₃ (2×1500 mL); 1000 mL water; and brine (2×1000 mL). (The aqueous base wash removed unreacted malonate ester-acid.) The straw colored organic solution was concentrated under vacuum (35° C.-40° C.) to give a cloudy, pale yellow oil with some white solid present. The oil was redissolved in 1500 mL of n-heptane and was filtered. The filtrate was concentrated under vacuum (40° C.-45° C.) to give 327 g of the titled compound as a pale yellow oil: ¹H NMR (400 MHz, CHLOROFORM-D) d ppm 0.82 (t, J=7.1 Hz, 3H), 0.85 (d, J=6.8 Hz, 3H), 0.99 (d, J=7.1 Hz, 3H), 1.20 (t, J=7.3 Hz, 3H), 2.42-2.49 (m, 1H), 3.39 (s, 2H) 4.12 (q, J=7.16 Hz, 3H). GC Chemical purity: 96.24%.

(4R,5R)-4,5-Dimethyl-3-oxo-octanoic acid ethyl ester (Alternative B)

To a solution containing 2.0 g (13.9 mmol) of (2R,3R)-2,3-dimethyl-hexanoic acid in 20 mL of dichloromethane was added 2.1 g (16.6 mmol) of chloromethylene dimethylammonium chloride. After stirring the resulting solution under nitrogen for 1.5 hours, the solvent was evaporated to give (2R,3R)-2,3-dimethyl-hexanoyl chloride. Butyl lithium (32.7 ml, 52.4 mmol) was added to a solution of diisopropylamine (4.9 g, 48.5 mmol) in dry THF (20 mL) under nitrogen at 0° C. and stirred for 20 minutes. The solution was cooled to −78° C. and 4.3 g (48.5 mmol) of ethyl acetate was added. The solution was stirred at that temperature for 45 minutes. (2R,3R)-2,3-Dimethyl-hexanoyl chloride in dry THF (20 mL) was slowly added to the ethyl acetate enolate at −78° C. and the resulting reaction mixture was allowed to warm to room temperature. The reaction mixture was stirred at room temperature for 2.5 hours and was cooled to 0° C. The reaction was quenched with a saturated solution of ammonium chloride and extracted into ethyl acetate. The solution was washed with brine, dried over MgSO₄ and concentrated. The resulting residue was filtered through a silica plug, eluting with 60/40 solution of hexane/ethyl acetate to afford 2.7 g (89.2% yield) of the titled compound as an oil.

(4R,5R)-4,5-Dimethyl-3-oxo-octanoic acid ethyl ester (Alternative C)

To a solution containing 1.0 g (6.9 mmol) of (2R,3R)-2,3-dimethyl-hexanoic acid in 10 mL of dichloromethane was added 1.1 g of chloromethylene dimethyl-ammonium chloride (8.3 mmol). The resulting solution was stirred under nitrogen for 1.5 hours. The solvent was subsequently evaporated to give (2R,3R)-2,3-dimethyl-hexanoyl chloride. To a solution containing 2.5 g (14.6 mmol) of potassium monoethyl malonate in 50 mL of acetonitrile was added 1.7 g (17.3 mmol) of magnesium chloride and 1.2 g (11.4 mmol) of triethylamine. The resulting mixture was stirred at room temperature for 2.5 hours. The reaction was cooled to 0° C. and a solution of the (2R,3R)-2,3-dimethyl-hexanoyl chloride in acetonitrile (20 mL) was slowly added followed by the addition of triethylamine (0.4 g, 0.4 mmol). The reaction was heated to 40° C. and stirred at that temperature for 6 hours. The reaction mixture was cooled to 25° C., quenched with a saturated solution of ammonium chloride and extracted into ethyl acetate. The solution was washed with brine, dried over MgSO$_4$ and concentrated. The resulting residue was filtered through a silica plug, eluting with 60/40 solution of hexane/ethyl acetate to afford 1.3 g (87.8% yield) of the titled compound as an oil.

(4R,5R)-3-Methoxyamino-4,5-dimethyl-(Z)-oct-2-enoic acid ethyl ester

A 2 L 3-necked round bottom flask, equipped with magnetic stirring and nitrogen inlet, was charged with 153 g (0.71 mol) of (4R,5R)-4,5-dimethyl-3-oxo-octanoic acid ethyl ester and 600 mL of anhydrous EtOH. The solution was cooled to 0° C.-5° C. with an ice bath and 65.6 g (0.79 mol) of methoxyamine hydrochloride was added, followed by 58.6 g (0.71 mol) of sodium acetate. This flask contents were slowly warmed to room temperature (about 2 hours) and the reaction mixture was stirred at room temperature for another 24 hours. The solvent (EtOH) was removed under reduced pressure and the mixture was charged with CH$_2$Cl$_2$ (2×300 mL), which was subsequently removed. The mixture was cooled to RT, diluted with CH$_2$Cl$_2$ (300 mL), stirred at room temperature for 0.5 hours, and filtered under 5 psig of nitrogen. The filter cake was washed with CH$_2$Cl$_2$ (150 mL). The filtrate was concentrated under vacuum (50° C.) to give 172 g (99% yield) of the titled compound as a light yellow oil: $^1$H NMR (400 MHz, CHLOROFORM-D) 0.87 (t, J=3.5 Hz, 5H), 0.89 (d, J=7.2 Hz, 3H), 1.08 (d, J=7.0 Hz, 3H), 1.24 (t, J=7.2 Hz, 4H), 1.3-1.55 (m, 2H), 2.25 (m, 1H), 3.15 (q, J=19.5 Hz, 2H) 3.81 (s, 3H), 4.14 (q, J=7.0 Hz, 2H).

(4R,5R)-3-Amino-4,5-dimethyl-(Z)-oct-2-enoic acid ethyl ester

A reactor vessel charged with 171 g of (4R,5R)-3-methoxyamino-4,5-dimethyl-(Z)-oct-2-enoic acid ethyl ester, 1600 mL of MeOH, and 65 g of Raney nickel (Ra—Ni) catalyst. The methoxyamino ester was reacted with hydrogen at 50 psig to 55 psig. During the hydrogenation, additional Ra—Ni was added at reaction times of 8 hours (20 g), 21 hours (20 g), and 37 hours (8 g). After the reaction was completed (51 hours), the Ra—Ni was filtered off and the filtrate was concentrated under reduced pressure to give 150 g (>99% yield) of the titled compound as an oil: $^1$H NMR (400 MHz, CHLOROFORM-D): 0.86 (t, J=4.5 Hz, 3H), 0.88 (d, J=4.9 Hz, 3H), 1.05-1.50 (m, 6H), 1.10 (d, J=7.0 Hz, 3H), 1.24 (t, J=7.2 Hz, 3H), 1.87 (m, 1H), 3.45 (s, 2H) 4.08 (q, J=7.0 Hz, 2H).

(4R,5R)-3-Acetylamino-4,5-dimethyl-(Z)-oct-2-enoic acid ethyl ester

To a 1 L 3-necked round bottom flask equipped with an overhead stirrer, thermocouple, addition funnel, and nitrogen inlet, was charged 150 g (0.70 mol) of (4R,5R)-3-amino-4,5-dimethyl-(Z)-oct-2-enoic acid ethyl ester and 50 mL of dry CH$_2$Cl$_2$. The reaction mixture was cooled to −20° C. To the mixture was added, successively, acetyl chloride (60 mL, 0.84 mol) and pyridine (66.8 g, 0.84 mol) over 0.5-hour time intervals. After the additions, the mixture was stirred at −20° C. to 0° C. for 2 hours and then filtered to remove the pyridine.HCl salt. The filtrate was diluted with 200 mL of CH$_2$Cl$_2$ and washed 2× with aliquots of aq NH$_4$Cl. The organic solution was treated with silica gel (50 g), MgSO$_4$ (20 g) and charcoal (20 g), and stirred at room temperature for 0.5 hours. The solids were filtered off and the filtrate was concentrated under reduced pressure to give 166.5 g (93% yield) of the titled compound as an oil: $^1$H NMR (400 MHz, CHLOROFORM-D) 0.85 (t, J=7.4 Hz, 3H), 0.95 (d, J=6.8 Hz, 3H), 1.00 (d, J=7.0 Hz, 3H), 1.11 (m, 1H) 1.29 (t, J=5.8 Hz, 3H), 1.40-1.25 (m, 2H), 1.65 (m, 1H) 2.13 (s, 3H), 3.80 (m, 1H) 4.2-4.14 (m, 3H), 5.01 (s, 1H), 11.28 (s, 1H).

(3R,4R,5R)-3-Acetylamino-4,5-dimethyl-octanoic acid ethyl ester

A reactor was charged with 166 g of (4R,5R)-3-acetylamino-4,5-dimethyl-(Z)-oct-2-enoic acid ethyl ester (substrate), 2650 mL of MeOH, and 36 g of Pd/SrCO$_3$ (lot#D25N17) catalyst. The substrate was reacted with H$_2$ at a pressure of 50 psig to 51 psig of. During hydrogenation, additional catalyst was added at a reaction time of 67 hours (10 g). After the reaction was completed (90 hours), Pd/SrCO$_3$ was filtered off and the filtrate was concentrated under reduced pressure to give 167 g (>99% yield) of the titled compound as an oil: $^1$H NMR (400 MHz, CHLOROFORM-D): 0.82 (d, J=6.8 Hz, 3H), 0.88 (t, J=7.2 Hz, 3H), 0.90 (d, J=6.6 Hz, 3H), 1.25 (t, J=7.3 Hz, 3H), 1.00-1.58 (m, 6H), 1.96 (s, 3H), 2.52 (q, J=5.2 Hz, 2H), 3.47 (s, 1H), 4.10-4.30 (m, 2H), 4.12 (t, J=7.1 Hz, 1H), 5.9 (d, 1H).

(3R,4R,5R)-3-Amino-4,5-dimethyl-octanoic acid hydrochloride

Under nitrogen, 167 g of crude (3R,4R,5R)-3-acetylamino-4,5-dimethyl-octanoic acid ethyl ester was diluted 1100 mL of 6N HCl, stirred at room temperature for 16 hours, and then heated to reflux for another 24 hours. The reaction mixture was concentrated and recharged with 500 mL of isopropyl alcohol (IPA), which was subsequently removed. Acetonitrile (500 mL) was added to the crude white HCl salt and the mixture stirred at 20° C. to 25° C. for 1 hour. The resulting slurry was filtered, and the solids isolated to give 97 g of the titled compound (67% yield, 89.7% chemical purity; 90.7% chiral purity with two major diastereomers, 6.8% and 1.5%): $^1$H NMR (CD$_3$OD): δ 0.89t J=7.0 Hz, 3H), 0.94t, J=6.9 Hz, 6H), 1.65-1.0 (m, 4H), 2.61 (dd, J=7.6 Hz, 1H), 2.73 (dd, J=4.6 HZ, 1H), 3.27 (m, J=1.6 Hz, 2H), 3.56 (m, 1H), 4.82 (s, 3H).

(3R,4R,5R)-3-Amino-4,5-dimethyl-octanoic acid (3R,4R,5R)-3-Amino-4,5-dimethyl-octanoic acid hydrochloride (92 g, 0.41 mol) was dissolved in 250 mL to 260 mL of dry MeOH in a 2 L 3-necked round bottom flask. To this solution was added $Et_3N$ (0.45 mol, 45.8 g) dropwise, which formed a white precipitate. The resulting slurry was stirred at room temperature for 15 minutes. The solvent was removed to dryness. The white solid was dispersed in 1 L of $CH_2Cl_2$ (1 L) and stirred for 1 hour. $CH_3CN$ (0.6 L) was added, and the slurry was stirred for another 0.5 hours. The slurry was filtered and the solids were washed 2× with 50 mL aliquots of $CH_3CN$, giving 71 g of the titled compound as a white solid (92% yield; 98.8% chiral purity; 99.7% chemical purity): $^1H$ NMR (400 MHz, $CD_3OD$): 0.89 (t, J=7.2 Hz, 3H), 0.91 (d, J=5.1 Hz, 3H), 0.93 (d, J=6.6 Hz, 3H), 1.02-1.65 (m, 4H), 2.26 (dd, J=10.2 Hz, 1H), 2.50 (dd, J=3.7 Hz, 1H), 3.27 (m, J=1.6 Hz, 2H) 3.33-3.28 (m, 1H), 4.82 (s, 3H).

EXAMPLE 9

(3R,4R,5R)-3-Acetylamino-4,5-dimethyl-octanoic acid ethyl ester (Catalyst Screening)

Ten mL ampoules were each charged with 20 mg of (4R,5R)-3-acetylamino-4,5-dimethyl-(Z)-oct-2-enoic acid ethyl ester (substrate), 2 mL of MeOH, and approximately 10 mg of catalyst. The ampoules were placed in a multi-reactor, purged with hydrogen, then pressurized to 20 psig with hydrogen and shaken at room temperature for 18 hours. For each ampoule following reaction, the solids were removed by filtration and the filtrate was analyzed by chiral GC (CHIRASIL-DEX CB, 140° C. isothermal). The table below provides conversion and ratio of (3R,4R,5R)-3-acetylamino-4,5-dimethyl-octanoic acid ethyl ester (desired diastereoisomer) to (3S,4R,5R)-3-acetylamino-4,5-dimethyl-octanoic acid ethyl ester (undesired diastereoisomer) for various hydrogenation catalysts.

| Entry | Catalyst | Source | Conv. % | RRR/SRR |
|---|---|---|---|---|
| 1 | 5% Pd/BaSO$_4$ | JM/B21H25 | 100 | 17.9:1 |
| 2 | 5% Rh/Al$_2$O$_3$ | Engelhard/SOC99179 | 100 | 9.1:1 |
| 3 | 1.5% Pt/C | Engelhard/CH02216 | 59 | 7.5:1 |
| 4 | 3% Pd/C | EngelhardSoc02089 | 100 | 7.2:1 |
| 5 | 5% Rh/C | Engelhard/JJH429 | 100 | 6.8:1 |
| 6 | Raney Nickel | AMC/A7000 | 24 | 5.6:1 |
| 7 | Raney Nickel | Grace/2800 | 0 | N/A |
| 8 | Raney Cobalt | AMC/A8B46 | 0 | N/A |
| 9 | 5% Pd/BaSO$_4$ (THF) | JM/B21H25 | 9 | 25.0:1 |
| 10 | 5% Pd/BaSO$_4$ | Degussa/CCI-1660 | 100 | 16.4:1 |
| 11 | 5% Pd/BaSO$_4$ (MeOH) | JM/B21H25 | 97 | 10.8:1 |
| 12 | Pd black | Am Plat/no# | 100 | 5.7:1 |
| 13 | Lindlar's catalyst | JM | 0 | N/A |
| 14 | 5% Pd/SrCO$_3$ | JM/D25N17 | 66 | 52:1 |
| 15 | 5% Pd/Al$_2$O$_3$ | JM/L02M05 | 100 | 49:1 |
| 16 | 1% Pd/Al$_2$O$_3$ | JM/K13M02 | 72 | 42:1 |
| 17 | 5% Pd/MgO | PMC/12221 | 93 | 38:1 |
| 18 | 5% Pd/CaCO$_3$ | PMC/13159 | >99 | 34:1 |
| 19 | 5% Pd/CaCO$_3$ | PMC/13261 | 89 | 33:1 |
| 20 | 5% Pd/BaSO$_4$ | PMC/13257 | 100 | 31:1 |
| 21 | 5% Pd/Al$_2$O$_3$ | PMC/13449 | 100 | 28:1 |
| 22 | 5% Pd/BaSO$_4$ | JM/B21H25 | 100 | 20:1 |
| 23 | 3% Pd/BaCO$_3$ | PMC/10313 | 100 | 17:1 |
| 24 | 5% Pd/CaCO$_3$ | PMC/12263 | 100 | 14:1 |
| 25 | 5% Pd/Al$_2$O$_3$ | PMC/1205 | 100 | 12:1 |
| 26 | 5% Pd/MgO | PMC/12243 | 100 | 13:1 |
| 27 | 5% Pd/Al$_2$O$_3$ | PMC/13079 | 100 | 12:1 |
| 28 | PtO$_2$ (Adam's Cat.) | PMC/12585 | 8 | 5:1 |
| 29 | 5% Pd/CaSO$_4$ | JM/K06M18 | 0 | N/A |
| 30 | 5% Pd/MgO | PMC/1221 | 94 | 47:1 |
| 31 | 5% Pd/SrCO$_3$ | JM/D25N17 | 100 | 43:1 |
| 32 | PdO$_2$ | Am Plat | 100 | 10:1 |
| 33 | 6% Pd/Deloxan | DEG/Pd369 | 100 | 10:1 |
| 34 | 20% Pd/C | PMC/20770 | 100 | 9:1 |
| 35 | 5% Rh/SiO$_2$ | ENG/JJH100 | 100 | 7:1 |
| 36 | 3% Pd/Deloxan | DEG/RG607 | 100 | 6:1 |
| 37 | 1% Pt on Polyethyleneimine/SiO$_2$ | JMJ27N37 | 0 | N/A |

EXAMPLE 10

(3R,4R,5R)-3-Acetylamino-4,5-dimethyl-heptanoic acid ethyl ester (Catalyst Screening)

Ten mL ampoules were each charged with 20 mg of (4R,5R)-3-acetylamino-4,5-dimethyl-(Z)-hept-2-enoic acid ethyl ester (substrate), 2 mL of MeOH, and approximately 10 mg of catalyst. The ampoules were placed in a multi-reactor, purged with hydrogen, then pressurized to 20 psig with hydrogen and shaken at room temperature for 18 hours. For each ampoule following reaction, the solids were removed by filtration and the filtrate was analyzed by chiral GC (CHIRASIL-DEX CB, 140° C. isothermal). The table below provides conversion and ratio of (3R,4R,5R)-3-acetylamino-4,5-dimethyl-heptanoic acid ethyl ester (desired diastereoisomer) to (3S,4R,5R)-3-acetylamino-4,5-dimethyl-heptanoic acid ethyl ester (undesired diastereoisomer) for various hydrogenation catalysts.

| Entry | Catalyst | Source | Conv. % | RRR/SRR |
|---|---|---|---|---|
| 1 | 5% Pd/SrCO$_3$ | JM/D25N17 | 100 | 41:1 |
| 2 | 3% Pd/BaCO$_3$ | PMC/10313 | 76 | 44:1 |
| 3 | 5% Pd/BaSO$_4$ | | 100 | 13:1 |
| 4 | 5% Pd/BaSO$_4$ | | >99 | 66:1 |
| 5 | 1% Pt on Polyethyleneimine/SiO$_2$ | JMJ27N37 | 0 | N/A |

It should be noted that, as used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled.

What is claimed is:

1. A method of making a compound of formula IV,

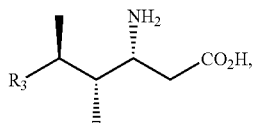

or a pharmaceutically acceptable salt thereof, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms, the method comprising:

treating a compound of formula 39,

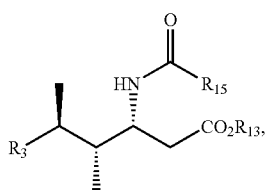

with an acid to give a hydrolysis product; and
optionally treating the hydrolysis product with an acid or base to give the compound of formula IV or a pharmaceutically acceptable salt thereof,
wherein $R_3$ in formula 39 is as defined for formula IV, and $R_{13}$ and $R_{15}$ in formula 39 are each independently selected from $(C_1-C_6)$alkyl, $(C_3-C_6)$cycloalkyl, and $(C_3-C_6)$cycloalkyl-$(C_1-C_3)$alkyl.

2. The method of claim 1, further comprising:
reacting a compound of formula 38,

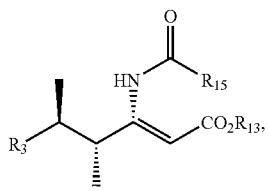

with $H_2$ in the presence of a catalyst to give the compound of formula 39, wherein $R_3$, $R_{13}$, and $R_{15}$ in formula 38 are as defined in claim 1.

3. The method of claim 2, further comprising:
reacting a compound of formula 36,

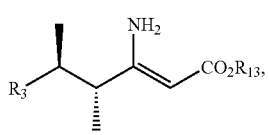

with an acylating agent to give the compound of formula 38, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with front one to five fluorine atoms, an the phonyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms, wherein $R_{13}$ is selected from $(C_1-C_6)$alkyl, $(C_3-C_6)$cycloalkyl, and $(C_3-C_6)$cycloalky-$(C_1-C_3)$alkyl.

4. The method of claim 3, wherein the acylating agent is a compound of formula 37,

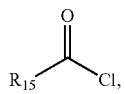

or a compound of formula 42,

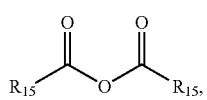

wherein $R_{15}$ is selected from $(C_1-C_6)$alkyl, $(C_3-C_6)$cycloalkyl, and $(C_3-C_6)$cycloalky-$(C_1-C_3)$alkyl.

5. The method of claim 3, further comprising:
reacting a compound of formula 33,

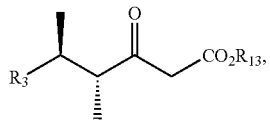

with ammonium acetate and acetic anhydride in the presence of a solvent to give the compound of formula 36, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms, and wherein $R_{13}$ is selected from $(C_1-C_6)$alkyl, $(C_3-C_6)$cycloalkyl, and $(C_3-C_6)$cycloalky-$(C_1-C_3)$alkyl.

6. The method of claim 5, further comprising: reacting a compound of formula 30,

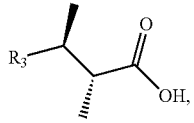

30 with a compound of formula 31,

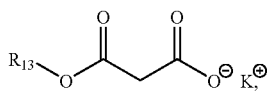

31 or with a compound of formula 32

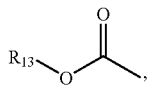

32 to give the compound of formula 33, wherein R$_3$ is a hydrogen atom, (C$_1$-C$_6$)alkyl, (C$_3$-C$_6$)alkyl, (C$_3$-C$_6$)cycloalkyl-(C$_1$-C$_3$)alkyl, phenyl, phenyl-(C$_1$-C$_3$)alkyl, pyridyl, or pyridyl-(C$_1$-C$_3$)alkyl, wherein the alkyl and cycloalkyl moieties or substituents are optionally substituted with from one to five fluorine atoms, and the phenyl and pyridyl substituents and the phenyl and pyridyl moieties of the phenyl-(C$_1$-C$_3$)alkyl and the pyridyl-(C$_1$-C$_3$)alkyl substituents are optionally substituted with from one to five substituents independently selected from chloro, fluoro, amino, nitro, cyano, hydroxy, (C$_1$-C$_3$)alkylamino, (C$_1$-C$_3$)alkyl optionally substituted with from one to three fluorine atoms, and (C$_1$-C$_3$)alkoxy optionally substituted with from one to three fluorine atoms, and wherein R$_{13}$ is selected from (C$_1$-C$_6$)alkyl, (C$_3$-C$_6$)cycloalkyl, and (C$_3$-C$_6$)cycloalky-(C$_1$-C$_3$)alkyl.

7. The method of claim 6, further comprising hydrolyzing a compound of formula 29,

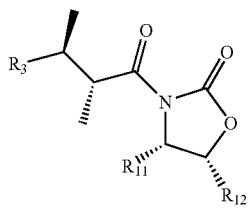

29 to give the compound of formula 30, wherein R$_3$ is a hydrogen atom, (C$_1$-C$_6$)alkyl, (C$_3$-C$_6$)cycloalkyl, (C$_3$-C$_6$)cycloalkyl-(C$_1$-C$_3$)alkyl, phenyl, phenyl-(C$_1$-C$_3$)alkyl, pyridyl, or pyridyl-(C$_1$-C$_3$)alkyl, wherein the alkyl and cycloalkyl moieties or substituents are optionally substituted with from one to five fluorine atoms, and phenyl and pyridyl substituents and the phenyl and pyridyl moieties of the phenyl-(C$_1$-C$_3$)alkyl and the pyridyl-(C$_1$-C$_3$)alkyl substituents are optionally substituted with from one to five substituents independently selected from chloro, fluoro, amino, nitro, cyano, hydroxy, (C$_1$-C$_3$)alkylamino, (C$_1$-C$_3$)alkyl optionally substituted with from one to three fluorine atoms, and (C$_1$C$_3$)alkoxy optionally substituted with from one to three fluorine atoms, and R$_{11}$ and R$_{12}$ in formula 29 are independently hydrogen, (C$_1$-C$_3$)alkyl, phenyl, or benzyl, provided that R$_{11}$ and R$_{12}$ are not both hydrogen.

8. The method of claim 7, further comprising reacting a compound of formula 28,

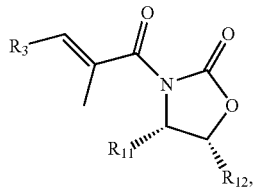

28 with CH$_3$Li or CH$_3$MgX, in the presence of a copper salt and a lithium salt, to give the compound of formula 29, wherein R$_3$ is a hydrogen atom, (C$_1$-C$_6$)alkyl, (C$_3$-C$_6$)alkyl, (C$_3$-C$_6$)cycloalkyl-(C$_1$-C$_3$)alkyl, phenyl, phenyl-(C$_1$-C$_3$)alkyl, pyridyl, or pyridyl-(C$_1$-C$_3$)alkyl, wherein the alkyl and cycloalkyl moieties or substituents are optionally substituted with from one to five fluorine atoms, and the phenyl and pyridyl substituents and the phenyl and pyridyl moieties of the phenyl-(C$_1$-C$_3$)alkyl and the pyridyl-(C$_1$-C$_3$)alkyl substituents are optionally substituted with from one to five substituents independently selected from chloro, fluoro, amino, nitro, cyano, hydroxy, (C$_1$-C$_3$)alkylamino, (C$_1$-C$_3$) alkyl optionally substituted with from one to three fluorine atoms, and (C$_1$-C$_3$)alkoxy optionally substituted with from one to three fluorine atoms, R$_{11}$ and R$_{12}$ in formula 28 are as defined in claim 7, and X is Cl, Br, or I.

9. The method of claim 8, further comprising reacting a compound of formula 26,

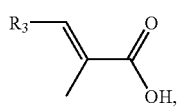

26 with a compound of formula 27,

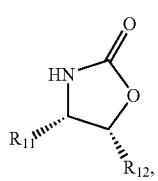

27 to give the compound of formula 28, wherein R$_3$ is a hydrogen atom, (C$_1$-C$_6$)alkyl, (C$_3$-C$_6$)cycloalkyl, (C$_3$-C$_6$)cycloalkyl-(C$_1$-C$_3$)alkyl, phenyl, phenyl-(C$_1$-C$_3$)alkyl, pyridyl, or pyridyl-(C$_1$-C$_3$)alkyl, wherein the alkyl and cycloalkyl moieties or substituents are optionally substituted with from one to five fluorine atoms, and the phenyl and pyridyl substituents and the phenyl and pyridyl moieties of the phenyl-(C$_1$-C$_3$)alkyl and the pyridyl-(C$_1$-C$_3$)alkyl substituents are optionally substituted with from one to five substituents independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms, and
wherein $R_{11}$ and $R_{12}$ are independently hydrogen $(C_1-C_3)$alkyl, phenyl, or benzyl, provided that both $R_{11}$ and $R_{12}$ are not both hydrogen.

10. The method of claim 3, further comprising: reacting a compound of formula 33,

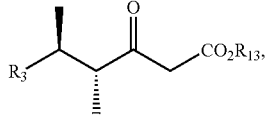

33 with a compound of formula 43,

   43, $R_{14}ONH_2$ in the presence of an acid, and in the absence of water, to give a compound of formula 35,

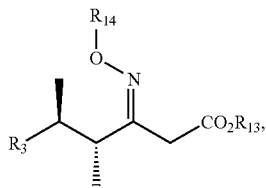

35 reacting the compound of formula 35 with $H_2$ in the presence of a catalyst to give the compound of formula 36;
wherein $R_3$ is a hydrogen atoms, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independent selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms,
wherein $R_{13}$ is selected from $(C_1-C_6)$alkyl, $(C_3-C_6)$cycloalkyl, and $(C_3-C_6)$cycloalky-$(C_1-C_3)$alkyl, and $R_{14}$ in formula 43 and in formula 35 is $(C_1-C_6)$alkyl, $(C_3-C_6)$cycloalkyl, $(C_3-C_6)$cycloalkyl-$(C_1-C_3)$alkyl, or silyl.

11. The method of claim 10, further comprising: reacting a compound of formula 30,

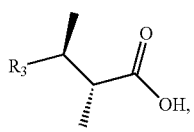

30 with a compound of formula 31,

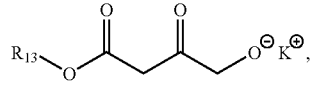

31 or with a compound of formula 32,

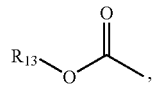

32 to give the compound of formula 33, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms, and
wherein $R_{13}$ is selected from $(C_1-C_6)$alkyl, $(C_3-C_6)$cycloalkyl, and $(C_3-C_6)$cycloalky-$(C_1C_3)$alkyl.

12. The method of claim 11, further comprising hydrolyzing a compound of formula 29,

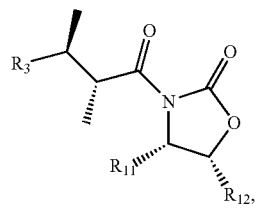

29 to give the compound of formula 30, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$alkyl optionally substituted with from one to three fluorine atoms, and $(C_1-C_3)$alkoxy optionally substituted with from one to three fluorine atoms, and $R_{11}$ and $R_{12}$ in formula 29 are each independently selected from hydrogen, $(C_1-C_3)$alkyl, phenyl, and benzyl, provided that $R_{11}$ and $R_{12}$ are not both hydrogen.

13. The method of claim 12, further comprising reacting a compound of formula 28,

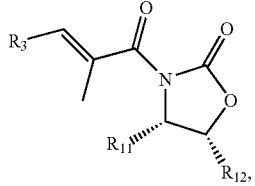

with CH₃Li or CH₃MgX, in the presence of a copper salt and a lithium salt to give the compound of formula 29, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$ alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$ alkyl optionally substituted with from one to three fluorine atoms, and $(C_1-C_3)$alkoxy optionally substituted with from one to three fluorine atoms, $R_{11}$ and $R_{12}$ in formula 28 are as defined in claim 12, and X is Cl, Br, or I.

14. The method of claim 13, further comprising reacting a compound of formula 26,

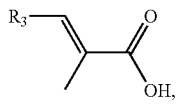

with a compound of formula 27,

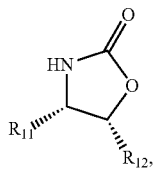

to give the compound of formula 28, wherein $R_3$ is a hydrogen atom, $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$ alkyl optionally substituted with from one to three fluorine atoms, and $(C_1-C_3)$alkoxy optionally substituted with from one to three fluorine atoms, $R_{11}$ and $R_{12}$ are each independently selected from hydrogen, $(C_1-C_3)$alkyl, phenyl, and benzyl, provided that $R_{11}$ and $R_{12}$ are not both hydrogen.

15. A method of making a compound of formula IV,

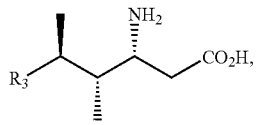

or a pharmaceutically acceptable salt thereof, wherein $R_3$ is a hydrogen atom, $(C_1-C_6)$alkyl, $(C_3-C_6)$cycloalkyl, $(C_3-C_6)$ cycloalkyl-$(C_1-C_3)$alkyl, phenyl, phenyl-$(C_1-C_3)$alkyl, pyridyl, or pyridyl-$(C_1-C_3)$alkyl, wherein the alkyl and cycloalkyl moieties or substituents are optionally substituted with from one to five fluorine atoms, and the phenyl and pyridyl substituents and the phenyl and pyridyl moieties of the phenyl-$(C_1-C_3)$alkyl and the pyridyl-$(C_1-C_3)$alkyl substituents are optionally substituted with from one to five substituents independently selected from chloro, fluoro, amino, nitro, cyano, hydroxy, $(C_1-C_3)$alkylamino, $(C_1-C_3)$ alkyl optionally substituted with from one to three fluorine atoms, and $(C_1-C_3)$alkoxy optionally substituted with from one to three fluorine atoms, the method comprising:

reacting a compound of formula 36,

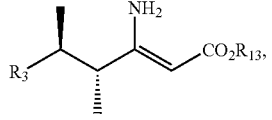

with H₂ in the presence of a catalyst to give the compound of formula 41,

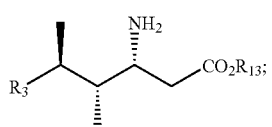

treating the compound of formula 41 with a first acid or base to give a hydrolysis product; and treating the hydrolysis product with a second base or acid to give the compound of formula IV or a pharmaceutically acceptable salt thereof;

wherein $R_3$ in formula 36 and in formula 41 is as defined above in formula IV, and $R_{13}$ in formula 36 and in formula 41 is $(C_1-C_6)$alkyl, $(C_3-C_6)$cycloalkyl, or $(C_3-C_6)$cycloalkyl-$(C_1-C_3)$alkyl.

16. A compound or salts thereof according to formula 35,

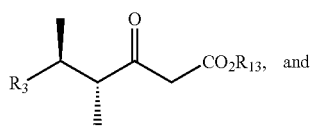

-continued

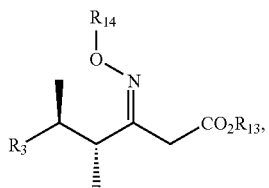

wherein

R$_3$ is a hydrogen atom, (C$_1$-C$_6$)alkyl, (C$_3$-C$_6$)cycloalkyl, (C$_3$-C$_6$)cycloalkyl-(C$_1$-C$_3$)alkyl, phenyl, phenyl-(C$_1$-C$_3$)alkyl, pyridyl, or pyridyl-(C$_1$-C$_3$)alkyl, wherein the alkyl and cycloalkyl moieties or substituents are optionally substituted with from one to five fluorine atoms, and the phenyl and pyridyl substituents and the phenyl and pyridyl moieties of the phenyl-(C$_1$-C$_3$)alkyl and the pyridyl-(C$_1$-C$_3$)alkyl substituents are optionally substituted with from one to five substituents independently selected from chloro, fluoro, amino, nitro, cyano, hydroxy, (C$_1$-C$_3$)alkylamino, (C$_1$-C$_3$)alkyl optionally substituted with from one to three fluorine atoms, and (C$_1$-C$_3$)alkoxy optionally substituted with from one to three fluorine atoms;

R$_{13}$ is (C$_1$-C$_6$)alkyl, (C$_3$-C$_6$)cycloalkyl, or (C$_3$-C$_6$)cycloalkyl-(C$_1$-C$_3$)alkyl; and R$_{14}$ is (C$_1$-C$_6$)alkyl, (C$_3$-C$_6$)cycloalkyl, (C$_3$-C$_6$)cycloalkyl-(C$_1$-C$_3$)alkyl, or silyl.

* * * * *